(12) United States Patent
Eberle et al.

(10) Patent No.: US 8,486,996 B2
(45) Date of Patent: Jul. 16, 2013

(54) AROYLFURANES AND AROYLTHIOPHENES

(75) Inventors: Martin Eberle, Bottmingen (CH); Felix Bachmann, Basel (CH); Alessandro Strebel, Oberwil (CH); Subho Roy, West Bengal (IN); Goutam Saha, West Bengal (IN); Subir Kumar Sadhukhan, West Bengal (IN); Rohit Saxena, Uttar Pradesh (IN); Sudhir Srivastava, Uttar Pradesh (IN)

(73) Assignee: Basilea Pharmaceutica AG, Basel (CH)

( * ) Notice: Subject to any disclaimer, the term of this patent is extended or adjusted under 35 U.S.C. 154(b) by 1822 days.

(21) Appl. No.: 11/433,511

(22) Filed: May 12, 2006

(65) Prior Publication Data

US 2006/0205739 A1    Sep. 14, 2006

(51) Int. Cl.
*A61K 31/34*    (2006.01)
*C07D 307/87*    (2006.01)

(52) U.S. Cl.
USPC .......................................... 514/470; 549/467

(58) Field of Classification Search
USPC .......................................... 549/467; 514/470
See application file for complete search history.

(56) References Cited

U.S. PATENT DOCUMENTS

| 7,144,885 B2 | 12/2006 | Zhang et al. |
| 7,351,735 B2 | 4/2008 | Zhang et al. |
| 7,384,947 B2 | 6/2008 | Zhang et al. |
| 7,585,888 B2 | 9/2009 | Zhang et al. |

FOREIGN PATENT DOCUMENTS

| EP | 1380576 | 1/2004 |
| WO | 0069842 | 11/2000 |
| WO | WO 01/07031 | 2/2001 |
| WO | 0117982 | 3/2001 |
| WO | 0125210 | 4/2001 |
| WO | WO 03/072561 A1 * | 9/2003 |
| WO | 2004007502 | 1/2004 |

OTHER PUBLICATIONS

Holmberg et al., Acta Academiae Aboensis, Series B: Mathematica et Physica (1968), 28(3), abstract only.*
Database WPI; Section Ch, Week 200117; Derwent Publications Ltd., London, GB; AN 2001-168497; XP002276317.
The International Search Report and Written Opinion by the International Searching Authority, mailed on Jul. 18, 2005, in the PCT application No. PCT/EP2004/053622.
D1: Mahboobi et al., "Synthetic 2-aroylindole derivatives as a new class of potent tubulin-inhibitory, antimitotic agents," J. Med. Chem. Dec. 20, 2001;44(26):4535-53.
D2. Beckers et al., "2-aroylindoles, a novel class of potent, orally active small molecule tubulin inhibitors," Cancer Res. Jun. 1, 2002;62(11):3113-9.
D3. Maziere et al, "No. 178-Fluoroaryl derivatives of some heterocyclic compounds," Bulletin De La Societe Chimique Francaise, 1963, pp. 1000-1003. (An English translation of D3 is enclosed.).
The European Examination Report by European Patent Office, issued on Mar. 29, 2004, in the European Application No. 03405911.3.
The European Examination Report by European Patent Office, issued on Jan. 24, 2008, in the European Application No. 07118973.2.
The Canadian Office Action, issued on Sep. 28, 2009, in the Canadian Application No. 2,545,821.

* cited by examiner

*Primary Examiner* — Rebecca Anderson

(57) ABSTRACT

The invention relates to novel substituted 2-(phenyl-, pyridyl- or pyrimidyl-carbonyl)-furanes and -thiophenes and related phenoxy/phenylthio-acetophenones and corresponding heterocyclic compounds, processes for the preparation thereof, pharmaceutical compositions containing same, the use thereof optionally in combination with one or more other pharmaceutically active compounds for the therapy of neoplastic diseases and autoimmune diseases, and a method for the treatment of such a diseases.

27 Claims, No Drawings

AROYLFURANES AND AROYLTHIOPHENES

CROSS-REFERENCE TO RELATED APPLICATIONS

This application claims priority from PCT/EP2004/053622, filed Dec. 21, 2004, which claims priority of European Application Number 03405911.3, filed Dec. 22, 2003, European Application Number 03405912.1, filed Dec. 22, 2003 and European Application Number 04405517.6, filed Aug. 19, 2004.

BACKGROUND OF THE INVENTION

Cancer is one of the leading causes of death in humans. Although a variety of drugs against neoplastic diseases have been developed and techniques are available such as surgery and radiation therapy, there is still a need for alternative and improved methods of treatment of neoplastic diseases.

Autoimmune diseases are associated with abnormal lymphoproliferation as a result of defects in the termination of lymphocyte activation and growth. Often, such diseases are associated with inflammation like rheumatoid arthritis, insulin dependent diabetes mellitus, multiple sclerosis, systemic lupus erythematosus and the like. The treatment of such diseases is focused on anti-inflammatory and immunosuppressive drugs which in numerous cases show severe side effects. Hence, there is a need for alternative drugs with a new mode of action showing less side effects.

Apoptosis is a term used to describe a series of cellular events which occur to bring about programmed cell death. There are various apoptotic pathways, some of which have been characterized, whereas others remain to be elucidated. If the balance between cell division and apoptosis is disturbed, life-threatening diseases including cancer, autoimmune disorders, neurodegenerative and cardiovascular diseases may occur.

In recent years it has become evident that programmed cell death (apoptosis) is as important to the health of a multicellular organism as cell division. By repeated cell division and differentiation throughout development or tissue repair, surplus or even harmful cells are generated. In order to maintain tissue homeostasis these cells have to be removed or killed. The delicate interplay between cell growth and apoptosis in an organism is mirrored in the complex molecular balance that determines whether an individual cell undergoes division, arrests in the cell cycle or commits to programmed cell death.

Dysregulation of cell proliferation, or lack of appropriate cell death, has wide ranging clinical implications. A number of diseases associated with such dysregulation involve hyperproliferation, inflammation, tissue remodeling and repair. Familiar indications in this category include cancers, restenosis, neointimal hyperplasia, angiogenesis, endometriosis, lymphoproliferative disorders, transplantation related pathologies (graft rejection), polyposis, loss of neural function in the case of tissue remodeling and the like. Such cells may lose the normal regulatory control of cell division, and may also fail to undergo appropriate cell death.

As apoptosis is inhibited or delayed in most types of proliferative, neoplastic diseases, induction of apoptosis is an option for treatment of cancer, especially in cancer types which show resistance to classic chemotherapy, radiation and immunotherapy (Apoptosis and Cancer Chemotherapy, Hickman and Dive, eds., Blackwell Publishing, 1999). Also in autoimmune and transplantation related diseases and pathologies compounds inducing apoptosis may be used to restore normal cell death processes and therefore can eradicate the symptoms and might cure the diseases. Further applications of compounds inducing apoptosis may be in restenosis, i.e. accumulation of vascular smooth muscle cells in the walls of arteries, and in persistent infections caused by a failure to eradicate bacteria- and virus-infected cells. Furthermore, apoptosis can be induced or re-established in epithelial cells, in endothelial cells, in muscle cells, and in others which have lost contact with extracellular matrix. These cells are potentially able to colonize other organs and therefore can develop into pathologies like neoplasias, endometriosis and the like.

SUMMARY OF THE INVENTION

Substituted 2-(phenyl-, pyridyl- or pyrimidyl-carbonyl)-furanes and -thiophenes of formula (I) and related phenoxy/phenylthio-acetophenones and corresponding heterocyclic compounds of formula (II) are selectively inducing apoptosis in cancer cells, and can be used for the treatment of neoplastic and autoimmune diseases. The invention relates to compounds of formula (I) and of formula (II) for use as medicaments as defined hereinafter, to novel compounds of formula (I) and of formula (II), to methods of synthesis of such compounds, to pharmaceutical compositions containing compounds of formula (I) and of formula (II), to the use of a compounds of formula (I) and of formula (II) for the preparation of a pharmaceutical composition for the treatment of neoplastic and autoimmune diseases, and to methods of treatment of neoplastic and autoimmune diseases using such compounds of formula (I) and of formula (II) or of pharmaceutical compositions containing same.

DETAILED DESCRIPTION OF THE INVENTION

The invention relates to compounds of formula (I)

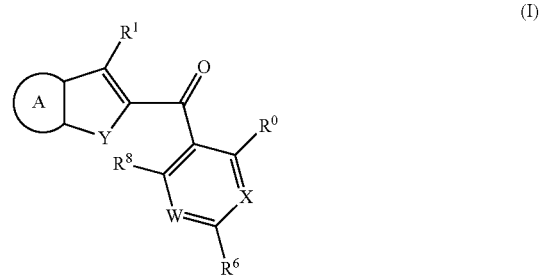

and of formula (II)

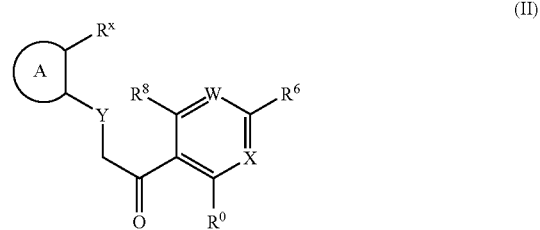

wherein ring A is selected from rings of formula (A¹), (A²), (A³), (A⁴), (A⁵), (A⁶) and (A⁷)

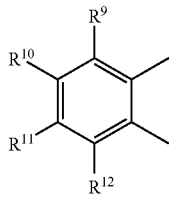
(A¹)

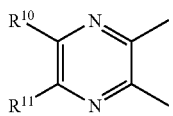
(A²)

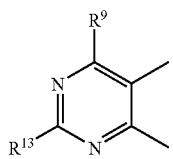
(A³)

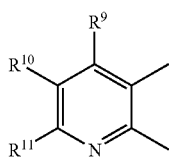
(A⁴)

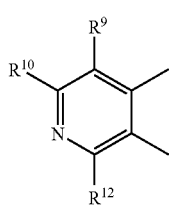
(A⁵)

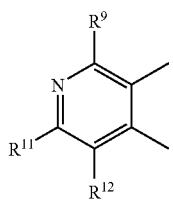
(A⁶)

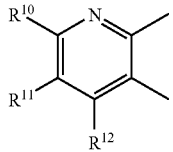
(A⁷)

W represents $CR^7$, N, or N→O;
X represents $CR^5$, N, or N→O;
Y represents O or S;
$R^0$ is $OCR^2R^3R^4$, $NR^{16}R^{17}$, lower alkoxymethyl, optionally substituted cyclohexyl, optionally substituted cyclohexenyl, optionally substituted phenyl, optionally substituted pyridyl, optionally substituted dihydropyridyl, optionally substituted tetrahydropyridinyl, optionally substituted pyrimidinyl, optionally substituted tetrahydropyranyl, or optionally substituted dihydropyranyl, and wherein the optional substituents are lower alkyl or lower alkoxy;
$R^x$ is —(C═O)$R^1$ or cyano;

$R^1$ is hydrogen, $OR^{14}$ or $NHR^{15}$;
$R^2$ is alkyl, halo-lower alkyl, hydroxy-lower alkyl, lower alkoxy-lower alkyl, lower alkoxy-lower alkoxy-lower alkyl, halo-lower alkoxy-lower alkyl, acyloxy-lower alkyl; cycloalkyl-lower alkyl, heterocyclyl-lower alkyl, optionally substituted phenyl-lower alkyl, optionally substituted heteroaryl-lower alkyl, optionally substituted alkenyl, optionally substituted alkinyl, cycloalkyl, optionally substituted phenyl, optionally substituted heteroaryl, halogen, cyano, carboxy, lower alkoxycarbonyl, lower alkoxy-lower alkoxycarbonyl;
$R^3$ and $R^4$, independently of each other, are hydrogen, fluorine or lower alkyl;
$R^5$ and $R^6$ independently of each other, represent hydrogen, lower alkyl, halo-lower alkyl, lower alkoxy-lower alkyl, lower alkoxy-lower alkoxy-lower alkyl, halo-lower alkoxy-lower alkyl, optionally substituted alkenyl, optionally substituted alkinyl, aryl, heteroaryl, lower alkoxy, halo-lower alkoxy, lower alkoxy-lower alkoxy, alkenyloxy, alkinyloxy, lower alkylcarbonyl, optionally substituted phenylcarbonyl, carboxy, lower alkoxycarbonyl, lower alkoxy-lower alkoxycarbonyl; aminocarbonyl wherein amino is unsubstituted or substituted by one or two substitutents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; cyano, halogen, or nitro;
or $R^5$ and $R^6$ together with the atoms of the phenyl or pyridine ring form a 5 or 6 membered carbocyclic or heterocyclic aromatic or aliphatic ring;
$R^7$ represents hydrogen, lower alkyl, halo-lower alkyl, hydroxy-lower alkyl, lower alkoxy-lower alkyl, aryloxy-lower alkyl, heteroaryloxy-lower alkyl, lower alkoxy-lower alkoxy-lower alkyl; aminoalkyl wherein amino is unsubstituted or substituted by one or two substituents selected from lower alkyl, hydroxy-lower alkyl, alkoxy-lower alkyl, amino-lower alkyl, alkylcarbonyl, alkoxycarbonyl, aminoalkoxycarbonyl, alkoxyalkoxycarbonyl and aminocarbonyl; optionally substituted alkenyl, optionally substituted alkinyl, cycloalkyl, cycloalkyl-lower alkyl; aryl, heteroaryl, arylalkyl or heteroarylalkyl, wherein aryl or heteroaryl are unsubstituted or substituted by up to three substituents selected from lower alkyl, halo-lower alkyl, lower alkoxy, halogen, amino, cyano and nitro; hydroxy, lower alkoxy, halo-lower alkoxy, lower alkoxy-lower alkoxy, cycloalkyloxy, cycloalkyl-lower alkoxy, aryloxy, aryl-lower alkoxy, heteroaryloxy, heteroaryl-lower alkoxy, alkenyloxy, alkinyloxy, alkylmercapto, alkylsulfinyl, halo-lower alkylsulfinyl, alkylsulfonyl, arylsulfonyl, heteroarylsulfonyl, aminosulfonyl wherein amino is unsubstituted or substituted by one or two substitutents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; amino optionally substituted by one or two substitutents selected from lower alkyl, cycloalkyl, cycloalkyl-lower alkyl, hydroxy-lower alkyl, lower alkoxy-lower alkyl, di-lower alkylamino-lower alkyl, optionally substituted phenyl, optionally substituted phenyl-lower alkyl, optionally substituted heteroaryl, optionally substituted heteroaryl-lower alkyl, alkylcarbonyl, alkoxycarbonyl or aminocarbonyl, and wherein alkyl or lower alkyl in each case may be substituted by halogen, lower alkoxy, aryl, heteroaryl or optionally substituted amino, or wherein the two substituents on nitrogen form together with the nitrogen heterocyclyl; lower alkylcarbonyl, halo-lower alkylcarbonyl, optionally substituted phenylcarbonyl, carboxy, lower alkoxycarbonyl, lower alkoxy-lower alkoxycarbonyl; aminocarbonyl wherein amino is unsubstituted or substituted by one or two substituents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; cyano, halogen, or nitro;

or $R^6$ and $R^7$ together with the atoms of the phenyl or pyridine ring form a 5 or 6 membered carbocyclic or heterocyclic aromatic or aliphatic ring;

$R^8$ represents hydrogen, lower alkyl, lower alkoxy or halogen; with the proviso that, if $R^5$ is bromo, $R^8$ cannot be fluoro;

or $R^7$ and $R^8$ together with the atoms of the phenyl or pyridine ring form a 5 or 6 membered carbocyclic or heterocyclic aromatic or aliphatic ring;

$R^9$, $R^{11}$ and $R^{12}$, independently of each other, represent hydrogen, lower alkyl, halo-lower alkyl, lower alkoxy-lower alkyl, lower alkoxy-lower alkoxy-lower alkyl, halo-lower alkoxy-lower alkyl, optionally substituted alkenyl, optionally substituted alkinyl, optionally substituted aryl, optionally substituted heteroaryl, lower alkoxy, halo-lower alkoxy, lower alkoxy-lower alkoxy, alkenyloxy, aryloxy, heteroaryloxy, alkylmercapto, alkylsulfinyl, halo-lower alkylsulfinyl, alkylsulfonyl, arylsulfonyl, heteroarylsulfonyl, lower alkylamino, lower alkylcarbonyl, optionally substituted phenylcarbonyl, carboxy, lower alkoxycarbonyl, lower alkoxy-lower alkoxycarbonyl; aminocarbonyl wherein amino is unsubstituted or substituted by one or two substituents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; cyano, halogen, or nitro;

$R^{10}$ represents hydrogen, lower alkyl, halo-lower alkyl, hydroxy-lower alkyl, lower alkoxy-lower alkyl, aryloxy-lower alkyl, heteroaryloxy-lower alkyl, lower alkoxy-lower alkoxy-lower alkyl; aminoalkyl wherein amino is unsubstituted or substituted by one or two substituents selected from lower alkyl, hydroxy-lower alkyl, alkoxy-lower alkyl, amino-lower alkyl, alkylcarbonyl, alkoxycarbonyl, aminoalkoxycarbonyl, alkoxyalkoxycarbonyl and aminocarbonyl, or wherein the two substituents on nitrogen form together with the nitrogen heterocyclyl; optionally substituted alkenyl, optionally substituted alkinyl, cycloalkyl, cycloalkyl-lower alkyl, aryl, heteroaryl; arylalkyl or heteroarylalkyl, wherein aryl or heteroaryl are unsubstituted or substituted by up to three substituents selected from lower alkyl, halo-lower alkyl, lower alkoxy, halogen, amino, cyano and nitro; hydroxy, lower alkoxy, halo-lower alkoxy, lower alkoxy-lower alkoxy, cycloalkyloxy, cycloalkyl-lower alkoxy, aryloxy, aryl-lower alkoxy, heteroaryloxy, heteroaryl-lower alkoxy, alkenyloxy, alkinyloxy, formyloxy, lower alkylcarbonyloxy, lower alkoxy-lower alkylcarbonyloxy, aryl-lower alkylcarbonyloxy; $OPO(OR)_2$ wherein the substituents R, independently of each other, represents hydrogen, lower alkyl, lower alkoxy-lower alkyl or aryl-lower alkyl; alkylmercapto, alkylsulfinyl, halo-lower alkylsulfinyl, alkylsulfonyl, arylsulfonyl, heteroarylsulfonyl; aminosulfonyl wherein amino is unsubstituted or substituted by one or two substitutents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; amino optionally substituted by one or two substitutents selected from lower alkyl, cycloalkyl, cycloalkyl-lower alkyl, hydroxy-lower alkyl, lower alkoxy-lower alkyl, di-lower alkylamino-lower alkyl, optionally substituted phenyl, optionally substituted phenyl-lower alkyl, optionally substituted heteroaryl, optionally substituted heteroaryl-lower alkyl, alkylcarbonyl, alkoxycarbonyl or aminocarbonyl, and wherein alkyl or lower alkyl in each case may be substituted by halogen, lower alkoxy, aryl, heteroaryl or optionally substituted amino, or wherein the two substituents on nitrogen form together with the nitrogen heterocyclyl; formyl, lower alkylcarbonyl, halo-lower alkylcarbonyl, alkoxy-lower alkylcarbonyl, aryl-lower alkylcarbonyl, optionally substituted phenylcarbonyl, carboxy, lower alkoxycarbonyl, lower alkoxy-lower alkoxycarbonyl; aminocarbonyl wherein amino is unsubstituted or substituted by one or two substitutents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; cyano, halogen, or nitro;

or adjacent substitutents $R^9$ and $R^{10}$, or $R^{10}$ and $R^{11}$, or $R^{11}$ and $R^{12}$ together with the atoms of the phenyl, pyridine or pyridazine ring form a 5 or 6 membered carbocyclic or heterocyclic aromatic or aliphatic ring;

$R^{13}$ represents hydrogen, lower alkyl, halogen, aryl, optionally substituted alkylthio, or amino, unsubstituted or substituted by one or two substitutents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl;

$R^{14}$ represents hydrogen, lower alkylcarbonyl, lower alkoxy-lower alkylcarbonyl, optionally substituted phenyl-lower alkylcarbonyl, optionally substituted heteroaryl-lower alkylcarbonyl, optionally substituted phenylcarbonyl, optionally substituted heteroarylcarbonyl, lower alkoxycarbonyl, lower alkoxy-lower alkoxycarbonyl, optionally substituted phenyl-lower alkoxycarbonyl; or aminocarbonyl, amino-lower alkylcarbonyl or amino-lower alkoxycarbonyl, wherein amino may be substituted by one or two substituents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl;

$R^{15}$ represents hydrogen, lower alkyl, lower alkylcarbonyl or lower alkylsulfonyl wherein lower alkyl may be substituted by hydroxy, lower alkoxy or halogen; lower alkoxycarbonyl or aminocarbonyl;

$R^{16}$ and $R^{17}$, independently of each other, represent lower alkyl, lower alkenyl or halo-lower alkyl, or $R^{16}$ and $R^{17}$ together with the nitrogen atom they are bound to form heterocyclyl;

and salts thereof.

The general terms used hereinbefore and hereinafter preferably have within the context of this disclosure the following meanings, unless otherwise indicated:

The prefix "lower" denotes a radical having up to and including a maximum of 7, especially up to and including a maximum of 4 carbon atoms, the radicals in question being either linear or branched with single or multiple branching.

Where the plural form is used for compounds, salts, and the like, this is taken to mean also a single compound, salt, or the like.

Double bonds in principle can have E- or Z-configuration. The compounds of this invention may therefore exist as isomeric mixtures or single isomers. If not specified both isomeric forms are intended.

Any asymmetric carbon atoms may be present in the (R)-, (S)- or (R,S)-configuration, preferably in the (R)- or (S)-configuration. The compounds may thus be present as mixtures of isomers or as pure isomers, preferably as enantiomerpure diastereomers.

The invention relates also to possible tautomers of the compounds of formula (I) or formula (II).

Alkyl has from 1 to 12, preferably from 1 to 7 carbon atoms, and is linear or branched. Alkyl is preferably lower alkyl.

Lower alkyl has 1 to 4 carbon atoms and is butyl, such as n-butyl, sec-butyl, isobutyl, tert-butyl, propyl, such as n-propyl or isopropyl, ethyl or methyl. Preferably lower alkyl is methyl or ethyl.

Cycloalkyl has preferably 3 to 7 ring carbon atoms, and may be unsubstitued or substituted, e.g. by lower alkyl or lower alkoxy. Cycloalkyl is, for example, cyclohexyl, cyclopentyl, methylcyclopentyl, or cyclopropyl.

Aryl stands for a mono- or bicyclic fused ring aromatic group with 5 to 10 carbon atoms, such as phenyl, 1-naphthyl or 2-naphthyl, or also a partially saturated bicyclic fused ring comprising a phenyl group, such as indanyl, dihydro- or tetrahydronaphthyl.

In optionally substituted phenyl or aryl, substituents are preferably lower alkyl, lower alkoxy, lower alkoxy-lower alkoxy, methylenedioxy, halo-lower alkyl, lower alkoxy-lower alkyl, halo, or nitro.

Heteroaryl represents an aromatic group containing at least one heteroatom selected from nitrogen, oxygen and sulfur, and is mono- or bicyclic. Monocyclic heteroaryl includes 5 or 6 membered heteroaryl groups containing 1, 2, 3 or 4 heteroatoms selected from nitrogen, sulfur and oxygen. Bicyclic heteroaryl includes 9 or 10 membered fused-ring heteroaryl groups. Examples of heteroaryl include pyrrolyl, thienyl, furyl, pyrazolyl, imidazolyl, triazolyl, oxazolyl, isoxazolyl, oxadiazolyl, thiazolyl, isothiazolyl, thiadiazolyl, pyridyl, pyridazinyl, pyrimidinyl, pyrazinyl, and benzo fused derivatives of such monocyclic heteroaryl groups, such as indolyl, benzimidazolyl or benzofuryl, quinolinyl, isoquinolinyl, quinazolinyl, or purinyl.

In optionally substituted heteroaryl, substituents are preferably lower alkyl, lower alkoxy, lower alkoxy-lower alkoxy, amino, optionally substituted by one or two substituents selected from lower alkyl, lower alkenyl and alkylcarbonyl, halo-lower alkyl, lower alkoxy-lower alkyl, halo, or nitro.

Alkenyl contains one or more, e.g. two or three, double bonds, and is preferably lower alkenyl, such as 1- or 2-butenyl, 1-propenyl, allyl or vinyl.

Alkinyl is preferably lower alkinyl, such as propargyl or acetylenyl.

In optionally substituted alkenyl or alkinyl, substituents are preferably lower alkyl, lower alkoxy, halo, di(lower alkyl) amino or acylamino, and are connected with a saturated carbon atom of alkenyl or alkinyl or with an unsaturated carbon atom of alkenyl.

Heterocyclyl designates preferably a saturated, partially saturated or unsaturated, mono- or bicyclic ring containg 4-10 atoms comprising one, two or three heteroatoms selected from nitrogen, oxygen and sulfur, which may, unless otherwise specified, be carbon or nitrogen linked, wherein a ring nitrogen atom may optionally be substituted by a group selected from lower alkyl, amino-lower alkyl, aryl, aryl-lower alkyl and acyl, and a ring carbon atom may be substituted by lower alkyl, amino-lower alkyl, aryl, aryl-lower alkyl, heteroaryl, lower alkoxy, hydroxy or oxo. Examples of heterocyclyl are pyrrolidinyl, oxazolidinyl, thiazolidinyl, piperidinyl, 3,4-dehydropiperidinyl, morpholinyl, piperazinyl, dioxolanyl and tetrahydropyranyl.

Acyl designates, for example, alkylcarbonyl, cycloalkylcarbonyl, arylcarbonyl, aryl-lower alkylcarbonyl, or heteroarylcarbonyl. Lower acyl is preferably lower alkylcarbonyl, in particular propionyl or acetyl.

Hydroxyalkyl is especially hydroxy-lower alkyl, preferably hydroxymethyl, 2-hydroxyethyl or 2-hydroxy-2-propyl.

Cyanoalkyl designates preferably cyanomethyl and cyanoethyl.

Haloalkyl is preferably fluoroalkyl, especially trifluoromethyl, 3,3,3-trifluoroethyl or pentafluoroethyl.

Halogen is fluorine, chlorine, bromine, or iodine.

Lower alkoxy is especially methoxy, ethoxy, isopropyloxy, or tert-butyloxy.

Arylalkyl includes aryl and alkyl as defined hereinbefore, and is e.g. benzyl, 1-phenethyl or 2-phenethyl.

Heteroarylalkyl includes heteroaryl and alkyl as defined hereinbefore, and is e.g. 2-, 3- or 4-pyridylmethyl, 1- or 2-pyrrolylmethyl, 1-pyrazolylmethyl, 1-imidazolylmethyl, 2-(1-imidazolyl)ethyl or 3-(1-imidazolyl)propyl.

Two adjacent substituents which together with the atoms of aryl or heteroaryl may form a 5 or 6 membered carbocyclic or heterocyclic ring are, for example, propylene, 1- or 2-oxopropylene, 1- or 2-oxapropylene, 1-oxapropylidene, methylenedioxy, difluoro-methylenedioxy, 1- or 2-azapropylene, 1- or 2-azapropylidene, 1,2- or 1,3-diaza-propylidene, 1,3-diaza-2-oxopropylene, butylene, 1- or 2-oxabutylene, ethylenedioxy, 1- or 2-azabutylene, or 1- or 2-azabutadienylidene, or such groups carrying further substituents as defined hereinbefore.

A 5 or 6 membered carbocyclic or heterocyclic aliphatic ring formed by two adjacent substituents on an aryl or heteroaryl ring together with the carbon atom they are bound to is e.g. cyclopentane, cyclohexane, such rings wherein one or preferably two carbon atoms are replaced by oxygen, or such rings wherein one carbon atom is replaced by oxygen and another one by nitrogen, and is optionally further substituted by lower alkyl, lower alkoxy or lower alkoxy-lower alkyl. Preferred examples are cyclic acetals formed from a carbonyl group with ethylene glycol or monoalkylated glycerin, i.e. rings wherein the substituents together represent 1,2-ethylenedioxy or 3-alkoxypropylene-1,2-dioxy.

A 5 or 6 membered carbocyclic or heterocyclic aromatic ring formed by two adjacent substituents on an aryl or heteroaryl ring together with the carbon atom they are bound to is e.g. phenyl or pyridyl, pyrrolyl, furanyl, thienyl, pyrimidinyl or pyrazinyl.

In substituted amino, the substituents are preferably those mentioned as substituents hereinbefore. In particular, substituted amino is alkylamino, dialkylamino, optionally substituted arylamino, optionally substituted arylalkylamino, lower alkylcarbonylamino, lower alkoxycarbonylamino or optionally substituted aminocarbonylamino.

Salts are especially the pharmaceutically acceptable salts of compounds of formula (I) and of formula (II).

Such salts are formed, for example, as acid addition salts, preferably with organic or inorganic acids, from compounds of formula (I) or of formula (II) with a basic nitrogen atom, especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, octanoic acid, decanoic acid, dodecanoic acid, glycolic acid, lactic acid, fumaric acid, succinic acid, adipic acid, pimelic acid, suberic acid, azelaic acid, malic acid, tartaric acid, citric acid, amino acids, such as glutamic acid or aspartic acid, maleic acid, hydroxymaleic acid, methylmaleic acid, cyclohexanecarboxylic acid, adamantanecarboxylic acid, benzoic acid, salicylic acid, 4-aminosalicylic acid, phthalic acid, phenylacetic acid, mandelic acid, cinnamic acid, methane- or ethane-sulfonic acid, 2-hydroxyethanesulfonic acid, ethane-1,2-disulfonic acid, benzenesulfonic acid, 2-naphthalenesulfonic acid, 1,5-naphthalene-disulfonic acid, 2-, 3- or 4-methylbenzenesulfonic acid, methylsulfuric acid, ethylsulfuric acid, dodecylsulfuric acid, N-cyclohexylsulfamic acid, N-methyl-, N-ethyl- or N-propyl-sulfamic acid, or other organic protonic acids, such as ascorbic acid.

For isolation or purification purposes it is also possible to use pharmaceutically unacceptable salts, for example picrates or perchlorates. For therapeutic use, only pharmaceutically acceptable salts or free compounds are employed (where applicable in the form of pharmaceutical preparations), and these are therefore preferred.

In view of the close relationship between the novel compounds in free form and those in the form of their salts, including those salts that can be used as intermediates, for example in the purification or identification of the novel compounds, any reference to the free compounds hereinbefore and hereinafter is to be understood as referring also to the corresponding salts, as appropriate and expedient.

The compound of formula (I) or formula (II) may be administered in the form of a pro-drug which is broken down in the human or animal body to give a compound of formula (I) or formula (II). Examples of pro-drugs include in vivo hydrolysable esters of a compound of formula (I) or formula (II).

Compounds of formula (II) and compounds of formula (I) may be regarded as intermediate and final products, or likewise as pro-drugs and final products, respectively. Conversions of compounds of formula (II) into corresponding compounds of formula (I) readily occur under in vitro and in vivo conditions, in particular in aqueous solution of pH 7 or higher. Both the compounds of formula (I) and of formula (II) have valuable pharmacological properties. The invention also relates to compounds of formula (I) and of formula (II) as defined hereinbefore for use as medicaments.

The efficacy of the compounds of the invention in inducing apoptosis in tumor cells can be demonstrated as follows:

Relative fluorescent activities of suitable tumor cell lines transfected with green fluorescent protein (GFP) are measured in the presence of compounds of the invention and of standard tumor drugs, using the method described in WO 99/35493. Suitable tumor cell lines are A20.2J, a BALB/c B cell lymphoma, PB-3c, an IL-3 dependent, non tumorigenic mastocyte line isolated from the bone marrow of a DBA/2 mouse, Jurkat, a human acute T cell leukemia cell line, K562, a human chronic myelogenous leukemia cell line, HL60, a human acute promyelocytic leukemia cell line, Ramos and Raji, human B-cell lymphoma cell lines, Hg and Hut78, human T-cell lymphoma cell lines, HeLa and KB, human squamous cell carcinoma cell lines, MCF7, SK-BR-3, PC3, HBL-100, SW480, H460 and H1792, human adenocarcinoma cell lines and HT-1080, a human fibrosarcoma cell line.

Preferred standard drugs as compounds for comparisons are: a) antimetabolites such as 5-fluorouracil (ICN), gemcitabine HCl (Gemzar™, Eli Lilly), b) alkylating agents such as oxaliplatin (Eloxantin™, Sanofi-Synthélabo), dacarbazin (Detimedac™, Medac), cyclo-phosphamide (Endoxan™, Asta) and carboplatin (Paraplatin™, Bristol-Meyers Squibb), c) cell-cycle inhibitor such as vinorelbine (Navelbine™, Robapharm), vinblastine (Velbe™, Eli Lilly), docetaxel (Taxotere™, Aventis), d) DNA breaker (topo-isomerase inhibitor, intercalator, strand breaker) such as doxorubicin HCl (Adriblastin™, Pharmacia-Upjohn), bleomycin (Asta-Medica), irinotecan (Campto™, Aventis), etoposide phosphate (Etopophos™, Bristol-Meyers Squibb), topotecan HCl, (Hycamtin™, GlaxoSmithKline), e) mixtures thereof, f) compounds interfering with the signal transduction pathway, such as caspase activity modifiers, agonists and antagonists of cell death receptors, modifiers of nucleases, phosphatases and kinases such as imatinib mesylate (Gleevec™, Novartis), dexamethasone, phorbol myristate acetate, cyclosporin A, quercetin, tamoxifen (Alexis Corporation, Switzerland).

Apoptosis is determined in a primary screen using a fluorescence plate reader and then in a secondary screen using FACS (fluorescence activated cell scanning). Compounds causing apoptosis without substantial cytotoxic side effects are chosen for further testing and characterization by using a combination of the following well established assays:

A) Nuclear staining with Hoechst 33342 dye providing information about nuclear morphology and DNA fragmentation which are hallmarks of apoptosis. B) MTS proliferation assay measuring the metabolic activity of cells. Viable cells are metabolically active whereas cells with compromised respiratory chain show a reduced activity in this test. C) AnnexinV binding assay which reflects the phosphatidylserine content of the outer lipid bilayer of the plasma membrane. This event is considered an early hallmark of apoptosis. D) PI staining for cell cycle distribution which shows any alterations in the distribution among the different phases of the cell cycle. Cell cycle arresting points can be determined. E) Proliferation assay monitoring DNA synthesis by incorporating bromodeoxyuridine (BrdU). Inhibitory effects on growth/proliferation can be directly determined. F) Cystein proteinase dependency, respectively caspase dependency are determined by using specific inhibitors. This provides information about possible involvement of specific proteases in the mechanisms.

On the basis of these studies, a compound of formula (I) and of formula (II) according to the invention shows therapeutic efficacy especially against neoplastic diseases and autoimmune diseases. In particular, the compounds of the invention are active against malignancies, e.g. epithelial neoplasms, squamous cell neoplasms, basal cell neoplasms, transitional cell papillomas and carcinomas, adenomas und adenocarcinomas, adnexal and skin appendage neoplasms, mucoepidermoid neoplasms, cystic neoplasms, mucinous and serous neoplasms, ductal-, lobular and medullary neoplasms, acinar cell neoplasms, complex epithelial neoplasms, specialized gonadal neoplasms, paragangliomas and glomus tumors, naevi and melanomas, soft tissue tumors and sarcomas, fibromatous neoplasms, myxomatous neoplasms, lipomatous neoplasms, myomatous neoplasms, complex mixed and stromal neoplasms, fibroepithelial neoplasms, synovial like neoplasms, mesothelial neoplasms, germ cell neoplasms, trophoblastic neoplasms, mesonephromas, blood vessel tumors, lymphatic vessel tumors, osseous and chondromatous neoplasms, giant cell tumors, miscellaneous bone tumors, odontogenic tumors, gliomas, neuroepitheliomatous neoplasms, meningiomas, nerve sheath tumors, granular cell tumors and alveolar soft part sarcomas, Hodgkin's and non Hodgkin's lymphomas, other lymphoreticular neoplasms, plasma cell tumors, mast cell tumors, immunoproliferative diseases, leukemias, miscellaneous myeloproliferative disorders, lymphoproliferative disorders and myelodysplastic syndromes.

The compounds of the invention are likewise active against autoimmune diseases, e.g. against systemic, discoid or subacute cutaneous lupus erythematosus, rheumatoid arthritis, antiphospholipid syndrome, CREST, progressive systemic sclerosis, mixed connective tissue disease (Sharp syndrome), Reiter's syndrome, juvenile arthritis, cold agglutinin disease, essential mixed cryoglobulinemia, rheumatic fever, ankylosing spondylitis, chronic polyarthritis, myasthenia gravis, multiple sclerosis, chronic inflammatory demyelinating polyneuropathy, Guillan-Barré syndrome, dermatomyositis/polymyositis, autoimmune hemolytic anemia, thrombocytopenic purpura, neutropenia, type I diabetes mellitus, thyroiditis (including Hashimoto's and Grave' disease), Addison's disease, polyglandular syndrome, pemphigus (vulgaris, foliaceus, sebaceous and vegetans), bullous and cicatricial pemphigoid, pemphigoid gestationis, epidermolysis bullosa acquisita, linear IgA disease, lichen sclerosus et atrophicus, morbus Duhring, psoriasis vulgaris, guttate, generalized pustular and localized pustular psoriasis, vitiligo, alopecia greata, primary biliary cirrhosis, autoimmune hepatitis, all forms of glomerulonephritis, pulmonal hemorrhage (goodpasture syndrome), IgA nephropathy, pernicious anemia and autoimmune gastritis, inflammatory bowel diseases (including colitis ulcerosa and morbus Crohn), Behcet's disease, Celic-Sprue disease, autoimmune uveitis, autoimmune myocarditis, granulomatous orchitis, aspermatogenesis without orchitis, idiopathic and secondary pulmonary fibrosis, inflammatory diesases with a possibility of autoimmune pathogensesis, such as pyoderma gangrensosum, lichen ruber, sarcoidosis (including Löfgren and cutaneous/subcutaneous type), granuloma anulare, allergic type I and type IV immunolgical reaction, asthma bronchiale, pollinosis, atopic, contact and airborne dermatitis, large vessel vasculitis (giant cell and Takayasu's arteritis), medium sized vessel vasculitis (polyarteritis nodosa, Kawasaki disease), small vessel vasculitis (Wegener's granulomatosis, Churg Strauss syndrome, microscopic polangiitis, Henoch-Schoenlein purpura, essential cryoglobulinemic vasculitis, cutaneous leukoklastic angiitis), hypersensitivity syndromes, toxic epidermal necrolysis (Stevens-Johnson syndrome, erythema multiforme), diseases due to drug side effects, all forms of cutaneous, organ-specific and systemic effects due to type I-VI (Coombs classification) immunologic forms of reaction, transplantation related pathologies, such as acute and chronic graft versus host and host versus graft disease, involving all organs (skin, heart, kidney, bone marrow, eye, liver, spleen, lung, muscle, central and peripheral nerve system, connective tissue, bone, blood and lymphatic vessel, genito-urinary system, ear, cartilage, primary and secondary lymphatic system including bone marrow, lymph node, thymus, gastrointestinal tract, including oro-pharynx, esophageus, stomach, small intestine, colon, and rectum, including parts of above mentioned organs down to single cell level and substructures, e.g. stem cells).

A compound of formula (I) and of formula (II) can be administered alone or in combination with one or more other therapeutic agents, possible combination therapy taking the form of fixed combinations, or the administration of a compound of the invention and one or more other therapeutic agents being staggered or given independently of one another, or the combined administration of fixed combinations and one or more other therapeutic agents. A compound of formula (I) and of formula (II) can, besides or in addition, be administered especially for tumor therapy in combination with chemotherapy, radiotherapy, immunotherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk. Particularly preferred is the use of compounds of formula (I) and of formula (II) in combination with radiotherapy. Therapeutic agents for possible combination are especially one or more cytostatic or cytotoxic compounds, for example a chemotherapeutic agent or several selected from the group comprising indarubicin, cytarabine, interferon, hydroxyurea, bisulfan, or an inhibitor of polyamine biosynthesis, an inhibitor of protein kinase, especially of serine/threonine protein kinase, such as protein kinase C, or of tyrosine protein kinase, such as epidermal growth factor receptor tyrosine kinase, a cytokine, a negative growth regulator, such as TGF-β or IFN-β, an aromatase inhibitor, a classical cytostatic, an inhibitor of the interaction of an SH2 domain with a phosphorylated protein, an inhibitor of Bcl-2 and modulators of the Bcl-2 family members such as Bax, Bid, Bad, Bim, Nip3 and BH3-only proteins.

A compound according to the invention is not only for the (prophylactic and preferably therapeutic) management of humans, but also for the treatment of other warm-blooded animals, for example of commercially useful animals, for example rodents, such as mice, rabbits or rats, or guinea-pigs. Such a compound may also be used as a reference standard in the test systems described above to permit a comparison with other compounds.

With the groups of preferred compounds of formula (I) and of formula (II) mentioned hereinafter, definitions of substituents from the general definitions mentioned hereinbefore may reasonably be used, for example, to replace more general definitions with more specific definitions or especially with definitions characterized as being preferred.

In particular, the invention refers to compounds of formula (I) as described hereinbefore.

More particularly, the invention refers to compounds of formula (I) wherein

A is selected from rings of formula ($A^1$), ($A^2$), ($A^3$), ($A^4$), ($A^5$), ($A^6$) and ($A^7$);

W represents $CR^7$ or N, and X represents $CR^5$ or N;

Y represents O or S;

$R^0$ is $OCR^2R^3R^4$;

$R^1$ is hydrogen, $OR^{14}$ or $NHR^{15}$;

$R^2$ is alkyl, halo-lower alkyl, hydroxy-lower alkyl, lower alkoxy-lower alkyl, lower alkoxy-lower alkoxy-lower alkyl, halo-lower alkoxy-lower alkyl, acyloxy-lower alkyl, optionally substituted alkenyl, optionally substituted alkinyl, cycloalkyl, optionally substituted phenyl, optionally substituted heteroaryl, halogen, or cyano;

$R^3$ and $R^4$, independently of each other, are hydrogen, fluorine or lower alkyl;

$R^5$ and $R^6$ independently of each other, represent hydrogen, lower alkyl, halo-lower alkyl, lower alkoxy-lower alkyl, lower alkoxy-lower alkoxy-lower alkyl, halo-lower alkoxy-lower alkyl, optionally substituted alkenyl, optionally substituted alkinyl, aryl, heteroaryl, lower alkoxy, halo-lower alkoxy, lower alkoxy-lower alkoxy, alkenyloxy, alkinyloxy, lower alkylcarbonyl, optionally substituted phenylcarbonyl, carboxy, lower alkoxycarbonyl, lower alkoxy-lower alkoxycarbonyl; aminocarbonyl wherein amino is unsubstituted or substituted by one or two substitutents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; cyano, halogen, or nitro;

or $R^5$ and $R^6$ together with the atoms of the phenyl or pyridine ring form a 5 or 6 membered carbocyclic or heterocyclic aromatic or aliphatic ring;

$R^7$ represents hydrogen, lower alkyl, halo-lower alkyl, hydroxy-lower alkyl, lower alkoxy-lower alkyl, aryloxy-lower alkyl, heteroaryloxy-lower alkyl, lower alkoxy-lower alkoxy-lower alkyl; aminoalkyl wherein amino is unsubstituted or substituted by one or two substituents selected from lower alkyl, hydroxy-lower alkyl, alkoxy-lower alkyl, amino-lower alkyl, alkylcarbonyl, alkoxycarbonyl, aminoalkoxycarbonyl, alkoxyalkoxycarbonyl and aminocarbonyl; optionally substituted alkenyl, optionally substituted alkinyl, cycloalkyl, cycloalkyl-lower alkyl; aryl, heteroaryl, arylalkyl or heteroarylalkyl, wherein aryl or heteroaryl are unsubstituted or substituted by up to three substituents selected from lower alkyl, halo-lower alkyl, lower alkoxy, halogen, amino, cyano and nitro; lower alkoxy, halo-lower alkoxy, lower alkoxy-lower alkoxy, cycloalkyloxy, cycloalkyl-lower alkoxy, aryloxy, aryl-lower alkoxy, heteroaryloxy, heteroaryl-lower alkoxy, alkenyloxy, alkinyloxy, alkylmercapto, alkylsulfinyl, halo-lower alkylsulfinyl, alkylsulfonyl, arylsulfonyl, heteroarylsulfonyl, aminosulfonyl wherein amino is unsubstituted or substituted by one or two substitutents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; amino optionally substituted by one or two substitutents selected from lower alkyl, cycloalkyl, cycloalkyl-lower alkyl, hydroxy-lower alkyl, lower alkoxy-lower alkyl, di-lower alkylamino-lower alkyl, optionally substituted phenyl, optionally substituted phenyl-lower alkyl, optionally substituted heteroaryl, optionally substituted heteroaryl-lower alkyl, alkylcarbonyl, alkoxycarbonyl or aminocarbonyl, and wherein alkyl or lower alkyl in each case may be substituted by halogen, lower alkoxy, aryl, heteroaryl or optionally substituted amino, or wherein the two substituents on nitrogen form together with the nitrogen heterocyclyl; lower alkylcarbonyl, halo-lower alkylcarbonyl, optionally substituted phenylcarbonyl, carboxy, lower alkoxycarbonyl, lower alkoxy-lower alkoxycarbonyl; aminocarbonyl wherein amino is unsubstituted or substituted by one or two substitutents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; cyano, halogen, or nitro;

or $R^6$ and $R^7$ together with the atoms of the phenyl or pyridine ring form a 5 or 6 membered carbocyclic or heterocyclic aromatic or aliphatic ring;

$R^8$ represents hydrogen, lower alkyl, lower alkoxy or halogen; with the proviso that, if $R^5$ is bromo, $R^8$ cannot be fluoro;

or $R^7$ and $R^8$ together with the atoms of the phenyl or pyridine ring form a 5 or 6 membered carbocyclic or heterocyclic aromatic or aliphatic ring;

$R^9$, $R^{11}$ and $R^{12}$, independently of each other, represent hydrogen, lower alkyl, halo-lower alkyl, lower alkoxy-lower alkyl, lower alkoxy-lower alkoxy-lower alkyl, halo-lower alkoxy-lower alkyl, optionally substituted alkenyl, optionally substituted alkinyl, optionally substituted aryl, optionally substituted heteroaryl, lower alkoxy, halo-lower alkoxy, lower alkoxy-lower alkoxy, alkenyloxy, aryloxy, heteroaryloxy, alkylmercapto, alkylsulfinyl, halo-lower alkylsulfinyl, alkylsulfonyl, arylsulfonyl, heteroarylsulfonyl, lower alkylcarbonyl, optionally substituted phenylcarbonyl, carboxy, lower alkoxycarbonyl, lower alkoxy-lower alkoxycarbonyl; aminocarbonyl wherein amino is unsubstituted or substituted by one or two substitutents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; cyano, halogen, or nitro;

$R^{10}$ represents hydrogen, lower alkyl, halo-lower alkyl, hydroxy-lower alkyl, lower alkoxy-lower alkyl, aryloxy-lower alkyl, heteroaryloxy-lower alkyl, lower alkoxy-lower alkoxy-lower alkyl; aminoalkyl wherein amino is unsubstituted or substituted by one or two substituents selected from lower alkyl, hydroxy-lower alkyl, alkoxy-lower alkyl, amino-lower alkyl, alkylcarbonyl, alkoxycarbonyl, aminoalkoxycarbonyl, alkoxyalkoxycarbonyl or aminocarbonyl; optionally substituted alkenyl, optionally substituted alkinyl, cycloalkyl, cycloalkyl-lower alkyl, aryl, heteroaryl; arylalkyl or heteroarylalkyl, wherein aryl or heteroaryl are unsubstituted or substituted by up to three substituents selected from lower alkyl, halo-lower alkyl, lower alkoxy, halogen, amino, cyano and nitro; lower alkoxy, halo-lower alkoxy, lower alkoxy-lower alkoxy, cycloalkyloxy, cycloalkyl-lower alkoxy, aryloxy, aryl-lower alkoxy, heteroaryloxy, heteroaryl-lower alkoxy, alkenyloxy, alkinyloxy, alkylmercapto, alkylsulfinyl, halo-lower alkylsulfinyl, alkylsulfonyl, arylsulfonyl, heteroarylsulfonyl; aminosulfonyl wherein amino is unsubstituted or substituted by one or two substitutents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; amino optionally substituted by one or two substitutents selected from lower alkyl, cycloalkyl, cycloalkyl-lower alkyl, hydroxy-lower alkyl, lower alkoxy-lower alkyl, di-lower alkylamino-lower alkyl, optionally substituted phenyl, optionally substituted phenyl-lower alkyl, optionally substituted heteroaryl, optionally substituted heteroaryl-lower alkyl, alkylcarbonyl, alkoxycarbonyl or aminocarbonyl, and wherein alkyl or lower alkyl in each case may be substituted by halogen, lower alkoxy, aryl, heteroaryl or optionally substituted amino, or wherein the two substituents on nitrogen form together with the nitrogen heterocyclyl; lower alkylcarbonyl, halo-lower alkylcarbonyl, optionally substituted phenylcarbonyl, carboxy, lower alkoxycarbonyl, lower alkoxycarbonyl; aminocarbonyl wherein amino is unsubstituted or substituted by one or two substitutents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; cyano, halogen, or nitro;

or adjacent substitutents $R^9$ and $R^{10}$, or $R^{10}$ and $R^{11}$, or $R^{11}$ and $R^{12}$ together with the atoms of the phenyl, pyridine or pyridazine ring form a 5 or 6 membered carbocyclic or heterocyclic aromatic or aliphatic ring;

$R^{13}$ represents hydrogen, lower alkyl, halogen, aryl, optionally substituted alkylthio, or amino, unsubstituted or substituted by one or two substituents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl;

$R^{14}$ represents hydrogen, lower alkylcarbonyl, lower alkoxy-lower alkylcarbonyl, optionally substituted phenyl-lower alkylcarbonyl, optionally substituted heteroaryl-lower alkylcarbonyl, optionally substituted phenylcarbonyl, optionally substituted heteroarylcarbonyl, lower alkoxycarbonyl, lower alkoxy-lower alkoxycarbonyl, optionally substituted phenyl-lower alkoxycarbonyl; or aminocarbonyl, amino-lower alkylcarbonyl or amino-lower alkoxycarbonyl, wherein amino may be substituted by one or two substituents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl;

$R^{15}$ represents hydrogen, lower alkyl, lower alkylcarbonyl wherein lower alkyl may be substituted by hydroxy, lower alkoxy or halogen, lower alkoxycarbonyl or aminocarbonyl;

and salts thereof.

Preferred are compounds of formula (I) wherein
A is selected from rings of formula ($A^1$), ($A^2$), ($A^3$), ($A^4$), ($A^5$), ($A^6$) and ($A^7$);
W represents $CR^7$ or N, and X represents $CR^5$ or N;
Y represents O or S;
$R^0$ is $OCR^2R^3R^4$;
$R^1$ is hydrogen, $OR^{14}$ or $NHR^{15}$;
$R^2$ is lower alkyl, halo-lower alkyl, optionally substituted alkenyl, optionally substituted alkinyl, cycloalkyl, halogen, or cyano;
$R^3$ and $R^4$, independently of each other, are hydrogen, fluorine or lower alkyl;
$R^5$ and $R^6$ independently of each other, represent hydrogen, lower alkyl, halo-lower alkyl, lower alkoxy-lower alkyl, lower alkoxy-lower alkoxy-lower alkyl, halo-lower alkoxy-lower alkyl, optionally substituted alkenyl, optionally substituted alkinyl, aryl, heteroaryl, lower alkoxy, halo-lower alkoxy, lower alkoxy-lower alkoxy, alkenyloxy, alkinyloxy, lower alkylcarbonyl, optionally substituted phenylcarbonyl, carboxy, lower alkoxycarbonyl, lower alkoxy-lower alkoxycarbonyl; aminocarbonyl wherein amino is unsubstituted or substituted by one or two substitutents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; cyano, halogen, or nitro;

or $R^5$ and $R^6$ together with the atoms of the phenyl or pyridine ring form a 5 or 6 membered carbocyclic or heterocyclic aromatic or aliphatic ring;

$R^7$ represents hydrogen, lower alkyl, halo-lower alkyl, hydroxy-lower alkyl, lower alkoxy-lower alkyl, aryloxy-lower alkyl, heteroaryloxy-lower alkyl, lower alkoxy-lower alkoxy-lower alkyl; aminoalkyl wherein amino is unsubstituted or substituted by one or two substituents selected from lower alkyl, hydroxy-lower alkyl, alkoxy-lower alkyl, amino-lower alkyl, alkylcarbonyl, alkoxycarbonyl, aminoalkoxycarbonyl, alkoxyalkoxycarbonyl and aminocarbonyl; optionally substituted alkenyl, optionally substituted alkinyl, cycloalkyl, cycloalkyl-lower alkyl; aryl, heteroaryl, arylalkyl or heteroarylalkyl, wherein aryl or heteroaryl are unsubstituted or substituted by up to three substituents selected from lower alkyl, halo-lower alkyl, lower alkoxy, halogen, amino, cyano and nitro; lower alkoxy, halo-lower alkoxy, lower alkoxy-lower alkoxy, cycloalkyloxy, cycloalkyl-lower alkoxy, aryloxy, aryl-lower alkoxy, heteroaryloxy, heteroaryl-lower alkoxy, alkenyloxy, alkinyloxy, alkylmercapto, alkylsulfinyl, halo-lower alkylsulfinyl, alkylsulfonyl, arylsulfonyl, heteroarylsulfonyl, aminosulfonyl wherein amino is unsubstituted or substituted by one or two substitutents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; amino optionally substituted by one or two substitutents selected from lower alkyl, cycloalkyl, cycloalkyl-lower alkyl, hydroxy-lower alkyl, lower alkoxy-lower alkyl, di-lower alkylamino-lower alkyl, optionally substituted phenyl, optionally substituted phenyl-lower alkyl, optionally substituted heteroaryl, optionally substituted heteroaryl-lower alkyl, alkylcarbonyl, alkoxycarbonyl or aminocarbonyl, and wherein alkyl or lower alkyl in each case may be substituted by halogen, lower alkoxy, aryl, heteroaryl or optionally substituted amino, or wherein the two substituents on nitrogen form together with the nitrogen heterocyclyl; lower alkylcarbonyl, halo-lower alkylcarbonyl, optionally substituted phenylcarbonyl, carboxy, lower alkoxycarbonyl, lower alkoxy-lower alkoxycarbonyl; aminocarbonyl wherein amino is unsubstituted or substituted by one or two substitutents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; cyano, halogen, or nitro;

or $R^6$ and $R^7$ together with the atoms of the phenyl or pyridine ring form a 5 or 6 membered carbocyclic or heterocyclic aromatic or aliphatic ring;

$R^8$ represents hydrogen, lower alkyl, lower alkoxy or halogen; with the proviso that, if $R^5$ is bromo, $R^8$ cannot be fluoro;

or $R^7$ and $R^8$ together with the atoms of the phenyl or pyridine ring form a 5 or 6 membered carbocyclic or heterocyclic aromatic or aliphatic ring;

$R^9$, $R^{11}$ and $R^{12}$, independently of each other, represent hydrogen, lower alkyl, halo-lower alkyl, lower alkoxy-lower alkyl, lower alkoxy-lower alkoxy-lower alkyl, halo-lower alkoxy-lower alkyl, optionally substituted alkenyl, optionally substituted alkinyl, optionally substituted aryl, optionally substituted heteroaryl, lower alkoxy, halo-lower alkoxy, lower alkoxy-lower alkoxy, alkenyloxy, aryloxy, heteroaryloxy, alkylmercapto, alkylsulfinyl, halo-lower alkylsulfinyl, alkylsulfonyl, arylsulfonyl, heteroarylsulfonyl, lower alkylcarbonyl, optionally substituted phenylcarbonyl, carboxy, lower alkoxycarbonyl, lower alkoxy-lower alkoxycarbonyl; aminocarbonyl wherein amino is unsubstituted or substituted by one or two substituents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; cyano, halogen, or nitro;

$R^{10}$ represents hydrogen, lower alkyl, halo-lower alkyl, hydroxy-lower alkyl, lower alkoxy-lower alkyl, aryloxy-lower alkyl, heteroaryloxy-lower alkyl, lower alkoxy-lower alkoxy-lower alkyl; aminoalkyl wherein amino is unsubstituted or substituted by one or two substituents selected from lower alkyl, hydroxy-lower alkyl, alkoxy-lower alkyl, amino-lower alkyl, alkylcarbonyl, alkoxycarbonyl, aminoalkoxycarbonyl, alkoxyalkoxycarbonyl or aminocarbonyl; optionally substituted alkenyl, optionally substituted alkinyl, cycloalkyl, cycloalkyl-lower alkyl, aryl, heteroaryl; arylalkyl or heteroarylalkyl, wherein aryl or heteroaryl are unsubstituted or substituted by up to three substituents selected from lower alkyl, halo-lower alkyl, lower alkoxy, halogen, amino, cyano and nitro; lower alkoxy, halo-lower alkoxy, lower alkoxy-lower alkoxy, cycloalkyloxy, cycloalkyl-lower alkoxy, aryloxy, aryl-lower alkoxy, heteroaryloxy, heteroaryl-lower alkoxy, alkenyloxy, alkinyloxy, alkylmercapto, alkylsulfinyl, halo-lower alkylsulfinyl, alkylsulfonyl, arylsulfonyl, heteroarylsulfonyl; aminosulfonyl wherein amino is unsubstituted or substituted by one or two substituents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; amino optionally substituted by one or two substituents selected from lower alkyl, cycloalkyl, cycloalkyl-lower alkyl, hydroxy-lower alkyl, lower alkoxy-lower alkyl, di-lower alkylamino-lower alkyl, optionally substituted phenyl, optionally substituted phenyl-lower alkyl, optionally substituted heteroaryl, optionally substituted heteroaryl-lower alkyl, alkylcarbonyl, alkoxycarbonyl or aminocarbonyl, and wherein alkyl or lower alkyl in each case may be substituted by halogen, lower alkoxy, aryl, heteroaryl or optionally substituted amino, or wherein the two substituents on nitrogen form together with the nitrogen heterocyclyl; lower alkylcarbonyl, halo-lower alkylcarbonyl, optionally substituted phenylcarbonyl, carboxy, lower alkoxycarbonyl, lower alkoxy-lower alkoxycarbonyl; aminocarbonyl wherein amino is unsubstituted or substituted by one or two substituents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; cyano, halogen, or nitro;

or adjacent substituents $R^9$ and $R^{10}$, or $R^{10}$ and $R^{11}$, or $R^{11}$ and $R^{12}$ together with the atoms of the phenyl, pyridine or pyridazine ring form a 5 or 6 membered carbocyclic or heterocyclic aromatic or aliphatic ring;

$R^{13}$ represents hydrogen, lower alkyl, halogen, aryl, optionally substituted alkylthio, or amino, unsubstituted or substituted by one or two substituents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl;

$R^{14}$ represents hydrogen, lower alkylcarbonyl, lower alkoxy-lower alkylcarbonyl, optionally substituted phenyl-lower alkylcarbonyl, optionally substituted heteroaryl-lower alkylcarbonyl, optionally substituted phenylcarbonyl, optionally substituted heteroarylcarbonyl, lower alkoxycarbonyl, lower alkoxy-lower alkoxycarbonyl, optionally substituted phenyl-lower alkoxycarbonyl; or aminocarbonyl, amino-lower alkylcarbonyl or amino-lower alkoxycarbonyl, wherein amino may be substituted by one or two substituents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl;

$R^{15}$ represents hydrogen, lower alkyl, lower alkylcarbonyl wherein lower alkyl may be substituted by hydroxy, lower alkoxy or halogen, lower alkoxycarbonyl or aminocarbonyl; and salts thereof.

More preferred are compounds of formula (I) wherein
A is selected from rings of formula ($A^1$), ($A^3$) and ($A^4$);
W represents $CR^7$ or N, and X represents $CR^5$ or N;
Y represents O;
$R^0$ is $OCR^2R^3R^4$;
$R^1$ is hydrogen, $OR^{14}$ or $NHR^{15}$;
$R^2$ is lower alkyl, halo-lower alkyl, optionally substituted alkenyl, optionally substituted alkinyl, cycloalkyl, halogen, or cyano;
$R^3$ and $R^4$, independently of each other, are hydrogen, fluorine or lower alkyl;
$R^5$ and $R^6$ independently of each other, represent hydrogen, lower alkyl, halo-lower alkyl, lower alkoxy-lower alkyl, lower alkoxy-lower alkoxy-lower alkyl, halo-lower alkoxy-lower alkyl, optionally substituted alkenyl, optionally substituted alkinyl, aryl, heteroaryl, lower alkoxy, halo-lower alkoxy, lower alkoxy-lower alkoxy, alkenyloxy, alkinyloxy, lower alkylcarbonyl, optionally substituted phenylcarbonyl, carboxy, lower alkoxycarbonyl, lower alkoxy-lower alkoxycarbonyl; aminocarbonyl wherein amino is unsubstituted or substituted by one or two substituents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; cyano, halogen, or nitro;

or $R^5$ and $R^6$ together with the atoms of the phenyl or pyridine ring form a 5 or 6 membered carbocyclic or heterocyclic aromatic or aliphatic ring;

$R^7$ represents hydrogen, lower alkyl, halo-lower alkyl, hydroxy-lower alkyl, lower alkoxy-lower alkyl, aryloxy-lower alkyl, heteroaryloxy-lower alkyl, lower alkoxy-lower alkoxy-lower alkyl; aminoalkyl wherein amino is unsubstituted or substituted by one or two substituents selected from lower alkyl, hydroxy-lower alkyl, alkoxy-lower alkyl, amino-lower alkyl, alkylcarbonyl, alkoxycarbonyl, aminoalkoxycarbonyl, alkoxyalkoxycarbonyl and aminocarbonyl; optionally substituted alkenyl, optionally substituted alkinyl, cycloalkyl, cycloalkyl-lower alkyl; aryl, heteroaryl, arylalkyl or heteroarylalkyl, wherein aryl or heteroaryl are unsubstituted or substituted by up to three substituents selected from lower alkyl, halo-lower alkyl, lower alkoxy, halogen, amino, cyano and nitro; lower alkoxy, halo-lower alkoxy, lower alkoxy-lower alkoxy, cycloalkyloxy, cycloalkyl-lower alkoxy, aryloxy, aryl-lower alkoxy, heteroaryloxy, heteroaryl-lower alkoxy, alkenyloxy, alkinyloxy, alkylmercapto, alkylsulfinyl, halo-lower alkylsulfinyl, alkylsulfonyl, arylsulfonyl, heteroarylsulfonyl, aminosulfonyl wherein amino is unsubstituted or substituted by one or two substitutents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; amino optionally substituted by one or two substitutents selected from lower alkyl, cycloalkyl, cycloalkyl-lower alkyl, hydroxy-lower alkyl, lower alkoxy-lower alkyl, di-lower alkylamino-lower alkyl, optionally substituted phenyl, optionally substituted phenyl-lower alkyl, optionally substituted heteroaryl, optionally substituted heteroaryl-lower alkyl, alkylcarbonyl, alkoxycarbonyl or aminocarbonyl, and wherein alkyl or lower alkyl in each case may be substituted by halogen, lower alkoxy, aryl, heteroaryl or optionally substituted amino, or wherein the two substituents on nitrogen form together with the nitrogen heterocyclyl; lower alkylcarbonyl, halo-lower alkylcarbonyl, optionally substituted phenylcarbonyl, carboxy, lower alkoxycarbonyl, lower alkoxy-lower alkoxycarbonyl; aminocarbonyl wherein amino is unsubstituted or substituted by one or two substitutents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; cyano, halogen, or nitro;

or $R^6$ and $R^7$ together with the atoms of the phenyl or pyridine ring form a 5 or 6 membered carbocyclic or heterocyclic aromatic or aliphatic ring;

$R^8$ represents hydrogen, lower alkyl, lower alkoxy or halogen; with the proviso that, if $R^5$ is bromo, $R^8$ cannot be fluoro;

or $R^7$ and $R^8$ together with the atoms of the phenyl or pyridine ring form a 5 or 6 membered carbocyclic or heterocyclic aromatic or aliphatic ring;

$R^9$, $R^{11}$ and $R^{12}$, independently of each other, represent hydrogen, lower alkyl, halo-lower alkyl, lower alkoxy-lower alkyl, lower alkoxy-lower alkoxy-lower alkyl, halo-lower alkoxy-lower alkyl, optionally substituted alkenyl, optionally substituted alkinyl, optionally substituted aryl, optionally substituted heteroaryl, lower alkoxy, halo-lower alkoxy, lower alkoxy-lower alkoxy, alkenyloxy, aryloxy, heteroaryloxy, alkylmercapto, alkylsulfinyl, halo-lower alkylsulfinyl, alkylsulfonyl, arylsulfonyl, heteroarylsulfonyl, lower alkylcarbonyl, optionally substituted phenylcarbonyl, carboxy, lower alkoxycarbonyl, lower alkoxy-lower alkoxycarbonyl; aminocarbonyl wherein amino is unsubstituted or substituted by one or two substitutents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; cyano, halogen, or nitro;

$R^{10}$ represents hydrogen, lower alkyl, halo-lower alkyl, hydroxy-lower alkyl, lower alkoxy-lower alkyl, aryloxy-lower alkyl, heteroaryloxy-lower alkyl, lower alkoxy-lower alkoxy-lower alkyl; aminoalkyl wherein amino is unsubstituted or substituted by one or two substituents selected from lower alkyl, hydroxy-lower alkyl, alkoxy-lower alkyl, amino-lower alkyl, alkylcarbonyl, alkoxycarbonyl, aminoalkoxycarbonyl, alkoxyalkoxycarbonyl or aminocarbonyl; optionally substituted alkenyl, optionally substituted alkinyl, cycloalkyl, cycloalkyl-lower alkyl, aryl, heteroaryl; arylalkyl or heteroarylalkyl, wherein aryl or heteroaryl are unsubstituted or substituted by up to three substituents selected from lower alkyl, halo-lower alkyl, lower alkoxy, halogen, amino, cyano and nitro; lower alkoxy, halo-lower alkoxy, lower alkoxy-lower alkoxy, cycloalkyloxy, cycloalkyl-lower alkoxy, aryloxy, aryl-lower alkoxy, heteroaryloxy, heteroaryl-lower alkoxy, alkenyloxy, alkinyloxy, alkylmercapto, alkylsulfinyl, halo-lower alkylsulfinyl, alkylsulfonyl, arylsulfonyl, heteroarylsulfonyl; aminosulfonyl wherein amino is unsubstituted or substituted by one or two substitutents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; amino optionally substituted by one or two substitutents selected from lower alkyl, cycloalkyl, cycloalkyl-lower alkyl, hydroxy-lower alkyl, lower alkoxy-lower alkyl, di-lower alkylamino-lower alkyl, optionally substituted phenyl, optionally substituted phenyl-lower alkyl, optionally substituted heteroaryl, optionally substituted heteroaryl-lower alkyl, alkylcarbonyl, alkoxycarbonyl or aminocarbonyl, and wherein alkyl or lower alkyl in each case may be substituted by halogen, lower alkoxy, aryl, heteroaryl or optionally substituted amino, or wherein the two substituents on nitrogen form together with the nitrogen heterocyclyl; lower alkylcarbonyl, halo-lower alkylcarbonyl, optionally substituted phenylcarbonyl, carboxy, lower alkoxycarbonyl, lower alkoxy-lower alkoxycarbonyl; aminocarbonyl wherein amino is unsubstituted or substituted by one or two substitutents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; cyano, halogen, or nitro;

or adjacent substitutents $R^9$ and $R^{10}$, or $R^{10}$ and $R^{11}$, or $R^{11}$ and $R^{12}$ together with the atoms of the phenyl, pyridine or pyridazine ring form a 5 or 6 membered carbocyclic or heterocyclic aromatic or aliphatic ring;

$R^{13}$ represents hydrogen, lower alkyl, halogen, aryl, optionally substituted alkylthio, or amino, unsubstituted or substituted by one or two substitutents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl;

$R^{14}$ represents hydrogen, lower alkylcarbonyl, lower alkoxy-lower alkylcarbonyl, optionally substituted phenyl-lower alkylcarbonyl, optionally substituted heteroaryl-lower alkylcarbonyl, optionally substituted phenylcarbonyl, optionally substituted heteroarylcarbonyl, lower alkoxycarbonyl, lower alkoxy-lower alkoxycarbonyl, optionally substituted phenyl-lower alkoxycarbonyl; or aminocarbonyl, amino-lower alkylcarbonyl or amino-lower alkoxycarbonyl, wherein amino may be substituted by one or two substituents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl;

$R^{15}$ represents hydrogen;

and salts thereof.

Particularly preferred are compounds of formula (I) wherein

A is selected from rings of formula $(A^1)$, $(A^3)$ and $(A^4)$;

W represents $CR^7$ or N, and X represents $CR^5$ or N;

Y represents O;

$R^0$ is $OCR^2R^3R^4$;

$R^1$ is $OR^{14}$ or $NHR^{15}$;

$R^2$ is lower alkyl, alkenyl, alkinyl, cycloalkyl, halogen, or cyano;

$R^3$ and $R^4$, independently of each other, are hydrogen, fluorine or lower alkyl;

$R^5$ and $R^6$ independently of each other, represent hydrogen, lower alkyl, halo-lower alkyl, lower alkoxy-lower alkyl, optionally substituted alkenyl, optionally substituted alkinyl, aryl, heteroaryl, lower alkoxy, lower alkoxy-lower alkoxy, alkenyloxy, alkinyloxy, lower alkylcarbonyl, optionally substituted phenylcarbonyl, carboxy, lower alkoxycarbonyl, lower alkoxy-lower alkoxycarbonyl, cyano, halogen, or nitro;

or $R^5$ and $R^6$ together with the atoms of the phenyl or pyridine ring form a 5 or 6 membered carbocyclic or heterocyclic aromatic or aliphatic ring;

$R^7$ represents hydrogen, lower alkyl, halo-lower alkyl, hydroxy-lower alkyl, lower alkoxy-lower alkyl, aryloxy-lower alkyl, heteroaryloxy-lower alkyl, lower alkoxy-lower alkoxy-lower alkyl; aminoalkyl wherein amino is unsubstituted or substituted by one or two substituents selected from lower alkyl, hydroxy-lower alkyl, alkoxy-lower alkyl, amino-lower alkyl, alkylcarbonyl, alkoxycarbonyl, aminoalkoxycarbonyl, alkoxyalkoxycarbonyl and aminocarbonyl; optionally substituted alkenyl, optionally substituted alkinyl, cycloalkyl, cycloalkyl-lower alkyl; aryl, heteroaryl, arylalkyl or heteroarylalkyl, wherein aryl or heteroaryl are unsubstituted or substituted by up to three substituents selected from lower alkyl, halo-lower alkyl, lower alkoxy, halogen, amino, cyano and nitro; lower alkoxy, halo-lower alkoxy, lower alkoxy-lower alkoxy, cycloalkyloxy, cycloalkyl-lower alkoxy, aryloxy, aryl-lower alkoxy, heteroaryloxy, heteroaryl-lower alkoxy, alkenyloxy, alkinyloxy, alkylmercapto, alkylsulfinyl, halo-lower alkylsulfinyl, alkylsulfonyl, arylsulfonyl, heteroarylsulfonyl, aminosulfonyl wherein amino is unsubstituted or substituted by one or two substituents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; amino optionally substituted by one or two substitutents selected from lower alkyl, cycloalkyl, cycloalkyl-lower alkyl, hydroxy-lower alkyl, lower alkoxy-lower alkyl, di-lower alkylamino-lower alkyl, optionally substituted phenyl, optionally substituted phenyl-lower alkyl, optionally substituted heteroaryl, optionally substituted heteroaryl-lower alkyl, alkylcarbonyl, alkoxycarbonyl or aminocarbonyl, and wherein alkyl or lower alkyl in each case may be substituted by halogen, lower alkoxy, aryl, heteroaryl or optionally substituted amino, or wherein the two substituents on nitrogen form together with the nitrogen heterocyclyl; lower alkylcarbonyl, halo-lower alkylcarbonyl, optionally substituted phenylcarbonyl, carboxy, lower alkoxycarbonyl, lower alkoxy-lower alkoxycarbonyl; aminocarbonyl wherein amino is unsubstituted or substituted by one or two substitutents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; cyano, halogen, or nitro;

or $R^6$ and $R^7$ together with the atoms of the phenyl or pyridine ring form a 5 or 6 membered carbocyclic or heterocyclic aromatic or aliphatic ring;

$R^8$ represents hydrogen;

$R^9$, $R^{11}$ and $R^{12}$, independently of each other, represent hydrogen, lower alkyl, halo-lower alkyl, lower alkoxy-lower alkyl, lower alkoxy-lower alkoxy-lower alkyl, halo-lower alkoxy-lower alkyl, optionally substituted alkenyl, optionally substituted alkinyl, optionally substituted aryl, optionally substituted heteroaryl, lower alkoxy, halo-lower alkoxy, lower alkoxy-lower alkoxy, alkenyloxy, aryloxy, heteroaryloxy, alkylmercapto, alkylsulfinyl, halo-lower alkylsulfinyl, alkylsulfonyl, arylsulfonyl, heteroarylsulfonyl, lower alkylcarbonyl, optionally substituted phenylcarbonyl, carboxy, lower alkoxycarbonyl, lower alkoxy-lower alkoxycarbonyl; aminocarbonyl wherein amino is unsubstituted or substituted by one or two substitutents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; cyano, halogen, or nitro;

$R^{10}$ represents hydrogen, lower alkyl, halo-lower alkyl, hydroxy-lower alkyl, lower alkoxy-lower alkyl, lower alkoxy-lower alkoxy-lower alkyl; aminoalkyl wherein amino is unsubstituted or substituted by one or two substituents selected from lower alkyl, hydroxy-lower alkyl, alkoxy-lower alkyl, amino-lower alkyl, alkylcarbonyl, alkoxycarbonyl, aminoalkoxycarbonyl, alkoxyalkoxycarbonyl or aminocarbonyl; optionally substituted alkenyl, optionally substituted alkinyl, cycloalkyl, cycloalkyl-lower alkyl, aryl, heteroaryl; arylalkyl or heteroarylalkyl, wherein aryl or heteroaryl are unsubstituted or substituted by up to three substituents selected from lower alkyl, halo-lower alkyl, lower alkoxy, halogen, amino, cyano and nitro; lower alkoxy, halo-lower alkoxy, lower alkoxy-lower alkoxy, cycloalkyloxy, cycloalkyl-lower alkoxy, aryloxy, aryl-lower alkoxy, heteroaryloxy, heteroaryl-lower alkoxy, alkenyloxy, alkinyloxy; amino optionally substituted by one or two substitutents selected from lower alkyl, cycloalkyl, cycloalkyl-lower alkyl, hydroxy-lower alkyl, lower alkoxy-lower alkyl, di-lower alkylamino-lower alkyl, optionally substituted phenyl, optionally substituted phenyl-lower alkyl, optionally substituted heteroaryl, optionally substituted heteroaryl-lower alkyl, alkylcarbonyl, alkoxycarbonyl or aminocarbonyl, and wherein alkyl or lower alkyl in each case may be substituted by halogen, lower alkoxy, aryl, heteroaryl or optionally substituted amino, or wherein the two substituents on nitrogen form together with the nitrogen heterocyclyl; lower alkylcarbonyl, halo-lower alkylcarbonyl, optionally substituted phenylcarbonyl, carboxy, lower alkoxycarbonyl, lower alkoxycarbonyl; aminocarbonyl wherein amino is unsubstituted or substituted by one or two substitutents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; cyano, halogen, or nitro;

$R^{13}$ represents hydrogen, lower alkyl, halogen, aryl, optionally substituted alkylthio, or amino, unsubstituted or substituted by one or two substituents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl;

$R^{14}$ represents hydrogen, lower alkylcarbonyl, lower alkoxy-lower alkylcarbonyl, optionally substituted phenyl-lower alkylcarbonyl, optionally substituted heteroaryl-lower alkylcarbonyl, optionally substituted phenylcarbonyl, optionally substituted heteroarylcarbonyl, lower alkoxycarbonyl, lower alkoxy-lower alkoxycarbonyl, optionally substituted phenyl-lower alkoxycarbonyl; or aminocarbonyl, amino-lower alkylcarbonyl or amino-lower alkoxycarbonyl, wherein amino may be substituted by one or two substituents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl;

$R^{15}$ represents hydrogen;
and salts thereof.

More preferred are compounds of formula (I) wherein

A is selected from rings of formula formula ($A^1$), ($A^3$) and ($A^4$);

W represents $CR^7$ and X represents $CR^5$;

Y represents O;

$R^0$ is $OCR^2R^3R^4$;

$R^1$ is $OR^{14}$ or $NHR^{15}$;

$R^2$ is lower alkyl;

$R^3$ is hydrogen;

$R^4$ is hydrogen;

$R^5$ and $R^6$ represent hydrogen;

$R^7$ represents hydrogen, lower alkyl, lower alkoxy, amino, optionally substituted by lower alkyl, alkylcarbonyl, alkoxycarbonyl or aminocarbonyl, carboxy, lower alkoxycarbonyl, aminocarbonyl, cyano, halogen, or nitro;

$R^8$ represents hydrogen;

$R^9$ and represent hydrogen;

$R^{10}$ represents hydrogen, alkyl, alkoxy or halogen;

$R^{11}$ represents hydrogen, lower alkyl, lower haloalkyl, lower alkoxyalkyl, hydroxyl, alkoxy, amino optionally substituted by lower alkyl, optionally substituted ary or heteroaryl;

$R^{12}$ represents hydrogen or lower alkyl;

$R^{13}$ represents hydrogen, lower alkyl, aryl, optionally substituted alkylthio, or amino, unsubstituted or substituted by lower alkyl, hydroxy-lower alkyl or lower alkoxy-lower alkyl, or wherein the two substituents on nitrogen form together with the nitrogen heterocyclyl;

$R^{14}$ represents hydrogen, lower alkylcarbonyl, lower alkoxy-lower alkylcarbonyl, lower alkoxycarbonyl, lower alkoxy-lower alkoxycarbonyl, aminocarbonyl or amino-lower alkylcarbonyl;

$R^{15}$ represents hydrogen;
and salts thereof.

Particularly preferred are compounds of formula (I) wherein

A is selected from rings of formula ($A^1$), ($A^3$) and ($A^4$);

W represents $CR^7$ and X represents $CR^5$;

Y represents O;

$R^0$ is $OCR^2R^3R^4$;

$R^1$ is $OR^{14}$;

$R^2$ is lower alkyl;

$R^3$ is hydrogen;

$R^4$ is hydrogen;

$R^5$ and $R^6$ represent hydrogen;

$R^7$ represents hydrogen, lower alkyl, lower alkoxy, amino, optionally substituted by lower alkyl, alkylcarbonyl, alkoxycarbonyl or aminocarbonyl, carboxy, lower alkoxycarbonyl, aminocarbonyl, cyano, halogen, or nitro;

$R^8$ represents hydrogen;

$R^9$ represent hydrogen;

$R^{10}$ represents hydrogen, alkyl, alkoxy or halogen;

$R^{11}$ represents hydrogen, lower alkyl, lower haloalkyl, lower alkoxyalkyl, hydroxyl, alkoxy, amino optionally substituted by lower alkyl, optionally substituted ary or heteroaryl;

$R^{12}$ represents hydrogen or lower alkyl;

$R^{13}$ represents hydrogen, lower alkyl, aryl, optionally substituted alkylthio, or amino, unsubstituted or substituted by lower alkyl, hydroxy-lower alkyl or lower alkoxy-lower alkyl, or wherein the two substituents on nitrogen form together with the nitrogen heterocyclyl;

$R^{14}$ represents hydrogen, lower alkylcarbonyl, lower alkoxy-lower alkylcarbonyl, lower alkoxycarbonyl, aminocarbonlylower alkoxy-lower alkoxycarbonyl, aminocarbonyl or amino-lower alkylcarbonyl;

$R^{15}$ represents hydrogen;
and salts thereof.

The invention likewise relates to compounds of formula (I) wherein ring A is selected from rings of formula ($A^1$), ($A^4$) and ($A^5$), W represents $CR^7$, N, or N→O;

X represents $CR^5$, N, or N→O;

Y represents O or S;

$R^0$ is $NR^{16}R^{17}$, lower alkoxymethyl, optionally substituted cyclohexyl, optionally substituted cyclohexenyl, optionally substituted phenyl, optionally substituted pyridyl, optionally substituted dihydropyridyl, optionally substituted tetrahydropyridinyl, optionally substituted pyrimidinyl, optionally substituted tetrahydropyranyl, or optionally substituted dihydropyranyl, and wherein the optional substituents are lower alkyl or lower alkoxy;

$R^1$ is hydrogen or $NHR^{15}$;

$R^5$ represents hydrogen, lower alkyl, halo-lower alkyl or fluoro;

$R^6$ is hydrogen;

$R^7$ represents hydrogen, lower alkyl, hydroxy, lower alkoxy, lower alkenyloxy, lower alkinyloxy, cyano, halogen, or nitro;

$R^8$ represents hydrogen or fluoro;

$R^9$ represents hydrogen, lower alkyl or halogen;

$R^{10}$ represents hydrogen, lower alkyl, halo-lower alkyl, hydroxy-lower alkyl, lower alkoxy-lower alkyl, cycloalkyl, hydroxy, lower alkoxy, halo-lower alkoxy, lower alkoxy-lower alkoxy, cycloalkyloxy, alkenyloxy, alkinyloxy, alkylmercapto, alkylsulfinyl, halo-lower alkylsulfinyl, alkylsulfonyl; amino optionally substituted by one or two substitutents selected from lower alkyl, cycloalkyl, cycloalkyl-lower alkyl, hydroxy-lower alkyl, lower alkoxy-lower alkyl, di-lower alkylamino-lower alkyl, alkylcarbonyl, alkoxycarbonyl or aminocarbonyl, and wherein alkyl or lower alkyl in each case may be substituted by halogen, lower alkoxy, aryl, heteroaryl or optionally substituted amino, or wherein the two substituents on nitrogen form together with the nitrogen heterocyclyl; lower alkylcarbonyl, halo-lower alkylcarbonyl, optionally substituted phenylcarbonyl, carboxy, lower alkoxycarbonyl, lower alkoxy-lower alkoxycarbonyl; cyano, halogen, or nitro;

$R^{11}$ represents hydrogen, lower alkyl, lower alkoxy, lower alkylamino, or halogen;

$R^{12}$ represents hydrogen, lower alkyl, halo-lower alkyl or fluoro;

$R^{15}$ represents hydrogen, lower alkylcarbonyl or lower alkylsulfonyl wherein lower alkyl may be substituted by hydroxy, lower alkoxy or halogen; or lower alkoxycarbonyl;

$R^{16}$ and $R^{17}$, independently of each other, represent lower alkyl, lower alkenyl or halo-lower alkyl, or $R^{16}$ and $R^{17}$ together with the nitrogen atom they are bound to form heterocyclyl;

and salts thereof.

More particularly the invention relates to compounds of formula (I) wherein ring A is selected from rings of formula ($A^1$), ($A^4$) and ($A^5$);

W represents $CR^7$, N, or N→O;
X represents $CR^5$, N, or N→O;
Y represents O or S;

$R^0$ is $NR^{16}R^{17}$, lower alkoxymethyl, optionally substituted cyclohexyl, optionally substituted cyclohexenyl, optionally substituted phenyl, optionally substituted pyridyl, optionally substituted dihydropyridyl, optionally substituted tetrahydropyridinyl, optionally substituted pyrimidinyl, optionally substituted tetrahydropyranyl, or optionally substituted dihydropyranyl, and wherein the optional substituents are lower alkyl or lower alkoxy;

$R^1$ is hydrogen or $NHR^{15}$;

$R^5$ represents hydrogen, lower alkyl, halo-lower alkyl or fluoro;

$R^6$ is hydrogen;

$R^7$ represents hydrogen, lower alkyl, hydroxy, lower alkoxy, lower alkenyloxy, lower alkinyloxy, cyano, halogen, or nitro;

$R^8$ represents hydrogen or fluoro;

$R^9$ represents hydrogen, lower alkyl or halogen;

$R^{10}$ represents lower alkyl, halo-lower alkyl, hydroxy-lower alkyl, lower alkoxy-lower alkyl, cycloalkyl, hydroxy, lower alkoxy, halo-lower alkoxy, lower alkoxy-lower alkoxy, cycloalkyloxy, alkenyloxy, alkinyloxy, lower alkylcarbonyl, halo-lower alkylcarbonyl, optionally substituted phenylcarbonyl, carboxy, lower alkoxycarbonyl, lower alkoxy-lower alkoxycarbonyl, cyano or halogen;

$R^{11}$ represents hydrogen, lower alkyl, lower alkoxy, lower alkylamino, or halogen;

$R^{12}$ represents hydrogen, lower alkyl, halo-lower alkyl or fluoro;

$R^{15}$ represents hydrogen;

$R^{16}$ and $R^{17}$, independently of each other, represent lower alkyl, lower alkenyl or halo-lower alkyl, or $R^{16}$ and $R^{17}$ together with the nitrogen atom they are bound to form heterocyclyl;

and salts thereof.

More preferably the invention relates to compounds of formula (I) wherein
ring A represents ($A^1$);
W represents $CR^7$, N, or N→O;
X represents $CR^5$, N, or N→O;
Y represents O;
$R^0$ is $NR^{16}R^{17}$, lower alkoxymethyl, optionally substituted cyclohexyl, optionally substituted cyclohexenyl, optionally substituted phenyl, optionally substituted pyridyl, optionally substituted dihydropyridyl, optionally substituted tetrahydropyridinyl, optionally substituted pyrimidinyl, optionally substituted tetrahydropyranyl, or optionally substituted dihydropyranyl, and wherein the optional substituents are lower alkyl or lower alkoxy;

$R^1$ is hydrogen or $NHR^{15}$;

$R^5$ represents hydrogen, lower alkyl, halo-lower alkyl or fluoro;

$R^6$ is hydrogen;

$R^7$ represents hydrogen, lower alkyl, hydroxy, lower alkoxy, lower alkenyloxy, lower alkinyloxy, cyano, halogen, or nitro;

$R^8$ represents hydrogen or fluoro;

$R^9$ represents hydrogen, lower alkyl or halogen;

$R^{10}$ represents lower alkyl, halo-lower alkyl, hydroxy-lower alkyl, lower alkoxy-lower alkyl, cycloalkyl, hydroxy, lower alkoxy, halo-lower alkoxy, lower alkoxy-lower alkoxy, cycloalkyloxy, alkenyloxy, alkinyloxy, lower alkylcarbonyl, halo-lower alkylcarbonyl, optionally substituted phenylcarbonyl, carboxy, lower alkoxycarbonyl, lower alkoxy-lower alkoxycarbonyl, cyano or halogen;

$R^{11}$ represents hydrogen, lower alkyl, lower alkoxy, lower alkylamino, or halogen;

$R^{12}$ represents hydrogen, lower alkyl, halo-lower alkyl or fluoro;

$R^{15}$ represents hydrogen;

$R^{16}$ and $R^{17}$, independently of each other, represent lower alkyl, lower alkenyl or halo-lower alkyl, or $R^{16}$ and $R^{17}$ together with the nitrogen atom they are bound to form heterocyclyl;

and salts thereof.

The invention likewise relates to compounds of formula (I) wherein
ring A represents ($A^4$);
W represents $CR^7$, N, or N→O;
X represents $CR^5$, N, or N→O;
Y represents S;
$R^0$ is $OCR^2R^3R^4$, $NR^{16}R^{17}$, lower alkoxymethyl, optionally substituted cyclohexyl, optionally substituted cyclohexenyl, optionally substituted phenyl, optionally substituted pyridyl, optionally substituted dihydropyridyl, optionally substituted tetrahydropyridinyl, optionally substituted pyrimidinyl, optionally substituted tetrahydropyranyl, or optionally substituted dihydropyranyl, and wherein the optional substituents are lower alkyl or lower alkoxy;

$R^1$ is hydrogen, $OR^{14}$ or $NHR^{15}$;

$R^2$ is lower alkyl, halo-lower alkyl, optionally substituted alkenyl, optionally substituted alkinyl, cycloalkyl, halogen, or cyano;

$R^3$ and $R^4$, independently of each other, are hydrogen, fluorine or lower alkyl;

$R^5$ and $R^6$ independently of each other, represent hydrogen, lower alkyl, halo-lower alkyl, lower alkoxy-lower alkyl, lower alkoxy-lower alkoxy-lower alkyl, halo-lower alkoxy-lower alkyl, optionally substituted alkenyl, optionally substituted alkinyl, aryl, heteroaryl, lower alkoxy, halo-lower alkoxy, lower alkoxy-lower alkoxy, alkenyloxy, alkinyloxy, lower alkylcarbonyl, optionally substituted phenylcarbonyl, carboxy, lower alkoxycarbonyl, lower alkoxy-lower alkoxycarbonyl; aminocarbonyl wherein amino is unsubstituted or substituted by one or two substitutents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; cyano, halogen, or nitro;

or $R^5$ and $R^6$ together with the atoms of the phenyl or pyridine ring form a 5 or 6 membered carbocyclic or heterocyclic aromatic or aliphatic ring;

$R^7$ represents hydrogen, lower alkyl, halo-lower alkyl, hydroxy-lower alkyl, lower alkoxy-lower alkyl, aryloxy-lower alkyl, heteroaryloxy-lower alkyl, lower alkoxy-lower alkoxy-lower alkyl; aminoalkyl wherein amino is unsubstituted or substituted by one or two substituents selected from lower alkyl, hydroxy-lower alkyl, alkoxy-lower alkyl, amino-lower alkyl, alkylcarbonyl, alkoxycarbonyl, aminoalkoxycarbonyl, alkoxyalkoxycarbonyl and aminocarbonyl; optionally substituted alkenyl, optionally substituted alkinyl, cycloalkyl, cycloalkyl-lower alkyl; aryl, heteroaryl, arylalkyl or heteroarylalkyl, wherein aryl or heteroaryl are unsubstituted or substituted by up to three substituents selected from lower alkyl, halo-lower alkyl, lower alkoxy, halogen, amino, cyano and nitro; lower alkoxy, halo-lower alkoxy, lower alkoxy-lower alkoxy, cycloalkyloxy, cycloalkyl-lower alkoxy, aryloxy, aryl-lower alkoxy, heteroaryloxy, heteroaryl-lower alkoxy, alkenyloxy, alkinyloxy, alkylmercapto, alkylsulfinyl, halo-lower alkylsulfinyl, alkylsulfonyl, arylsulfonyl, heteroarylsulfonyl, aminosulfonyl wherein amino is unsubstituted or substituted by one or two substitutents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; amino optionally substituted by one or two substitutents selected from lower alkyl, cycloalkyl, cycloalkyl-lower alkyl, hydroxy-lower alkyl, lower alkoxy-lower alkyl, di-lower alkylamino-lower alkyl, optionally substituted phenyl, optionally substituted phenyl-lower alkyl, optionally substituted heteroaryl, optionally substituted heteroaryl-lower alkyl, alkylcarbonyl, alkoxycarbonyl or aminocarbonyl, and wherein alkyl or lower alkyl in each case may be substituted by halogen, lower alkoxy, aryl, heteroaryl or optionally substituted amino, or wherein the two substituents on nitrogen form together with the nitrogen heterocyclyl; lower alkylcarbonyl, halo-lower alkylcarbonyl, optionally substituted phenylcarbonyl, carboxy, lower alkoxycarbonyl, lower alkoxy-lower alkoxycarbonyl; aminocarbonyl wherein amino is unsubstituted or substituted by one or two substitutents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; cyano, halogen, or nitro;

or $R^6$ and $R^7$ together with the atoms of the phenyl or pyridine ring form a 5 or 6 membered carbocyclic or heterocyclic aromatic or aliphatic ring;

$R^8$ represents hydrogen, lower alkyl, lower alkoxy or halogen;

or $R^7$ and $R^8$ together with the atoms of the phenyl or pyridine ring form a 5 or 6 membered carbocyclic or heterocyclic aromatic or aliphatic ring;

$R^9$, $R^{10}$ and $R^{11}$, independently of each other, represent hydrogen, lower alkyl, halo-lower alkyl, lower alkoxy-lower alkyl, lower alkoxy-lower alkoxy-lower alkyl, halo-lower alkoxy-lower alkyl, optionally substituted alkenyl, optionally substituted alkinyl, optionally substituted aryl, optionally substituted heteroaryl, lower alkoxy, halo-lower alkoxy, lower alkoxy-lower alkoxy, alkenyloxy, aryloxy, heteroaryloxy, alkylmercapto, alkylsulfinyl, halo-lower alkylsulfinyl, alkylsulfonyl, arylsulfonyl, heteroarylsulfonyl, lower alkylcarbonyl, optionally substituted phenylcarbonyl, carboxy, lower alkoxycarbonyl, lower alkoxy-lower alkoxycarbonyl; aminocarbonyl wherein amino is unsubstituted or substituted by one or two substitutents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; cyano, halogen, or nitro;

or adjacent substitutents $R^9$ and $R^{10}$, or $R^{10}$ and $R^{11}$ together with the atoms of the pyridine ring form a 5 or 6 membered carbocyclic or heterocyclic aromatic or aliphatic ring;

$R^{14}$ represents hydrogen, lower alkylcarbonyl, lower alkoxy-lower alkylcarbonyl, optionally substituted phenyl-lower alkylcarbonyl, optionally substituted heteroaryl-lower alkylcarbonyl, optionally substituted phenylcarbonyl, optionally substituted heteroarylcarbonyl, lower alkoxycarbonyl, lower alkoxy-lower alkoxycarbonyl, optionally substituted phenyl-lower alkoxycarbonyl; or aminocarbonyl, amino-lower alkylcarbonyl or amino-lower alkoxycarbonyl, wherein amino may be substituted by one or two substituents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl;

$R^{15}$ represents hydrogen, lower alkylcarbonyl or lower alkylsulfonyl wherein lower alkyl may be substituted by hydroxy, lower alkoxy or halogen; or lower alkoxycarbonyl;

and salts thereof.

Preferably the invention relates to compounds of formula (I) wherein ring A represents ($A^4$);
W represents $CR^7$ or N;
X represents $CR^5$ or N;
Y represents S;
$R^0$ is $OCR^2R^3R^4$ or $NR^{16}R^{17}$;
$R^1$ is hydrogen or $NHR^{15}$;
$R^2$ is lower alkyl, halo-lower alkyl, optionally substituted alkenyl, optionally substituted alkinyl, cycloalkyl, halogen, or cyano;
$R^3$ and $R^4$, independently of each other, are hydrogen, fluorine or lower alkyl;
$R^5$ represents hydrogen, lower alkyl, halo-lower alkyl or fluoro;
$R^6$ is hydrogen;
$R^7$ represents hydrogen, lower alkyl, hydroxy, lower alkoxy, lower alkenyloxy, lower alkinyloxy, cyano, halogen, or nitro;
$R^8$ represents hydrogen or fluoro;
$R^9$ represents hydrogen, lower alkyl or halogen;
$R^{10}$ and $R^{11}$, independenty of each other, represent lower alkyl, halo-lower alkyl, hydroxy-lower alkyl, lower alkoxy-lower alkyl, cycloalkyl, hydroxy, lower alkoxy, halo-lower alkoxy, lower alkoxy-lower alkoxy, cycloalkyloxy, alkenyloxy, alkinyloxy, lower alkylcarbonyl, halo-lower alkylcarbonyl, optionally substituted phenylcarbonyl, carboxy, lower alkoxycarbonyl, lower alkoxy-lower alkoxycarbonyl, cyano or halogen;

$R^{15}$ represents hydrogen;

$R^{16}$ and $R^{17}$, independently of each other, represent lower alkyl, lower alkenyl or halo-lower alkyl, or $R^{16}$ and $R^{17}$ together with the nitrogen atom they are bound to form heterocyclyl;

and salts thereof.

More preferably the invention relates to compounds of formula (I) wherein ring A represents ($A^1$);
W represents $CR^7$;
X represents $CR^5$;
Y represents O;
$R^0$ is $OCR^2R^3R^4$;
$R^1$ is $NHR^{15}$;
$R^2$ is lower alkyl, vinyl or trifluoromethyl;
$R^3$ is hydrogen or methyl;
$R^4$, $R^5$ and $R^6$ represent hydrogen;
$R^7$ represents hydrogen, lower alkyl, lower alkoxy, fluoro, chloro, or nitro;
$R^8$ and $R^9$ represent hydrogen;
$R^{10}$ represents hydrogen, lower alkyl, hydroxy, lower alkoxy or halogen;
$R^{11}$ and $R^{12}$ represents hydrogen;
$R^{15}$ represents hydrogen, methanesulfonyl or methoxyacetyl;
and salts thereof.

Likewise the invention relates to compounds of formula (I) wherein ring A represents ($A^4$);
W represents $CR^7$;
X represents $CR^5$;
Y represents O;
$R^0$ is ethoxy;
$R^1$ is amino;
$R^5$ and $R^6$ represent hydrogen;
$R^7$ represents fluoro or chloro;
$R^8$, $R^9$ and $R^{10}$ represent hydrogen;
$R^{11}$ represents methyl;
and salts thereof.

Likewise the invention relates to the compound of formula (I) wherein ring A represents ($A^5$);
W represents $CR^7$;
X represents $CR^5$;
Y represents O;
$R^0$ is ethoxy;
$R^1$ is amino;
$R^5$ and $R^6$ represent hydrogen;
$R^7$ represents fluoro;
$R^8$ and $R^9$ represent hydrogen;
$R^{10}$ represents methyl;
$R^{12}$ represents hydrogen;
and salts thereof.

Likewise the invention relates to compounds of formula (I) wherein ring A represents ($A^1$);
W represents $CR^7$;
X represents N;
Y represents O;
$R^0$ is ethoxy, 1-morpholinyl or 1-piperidinyl;
$R^1$ is amino;
$R^6$, $R^7$, $R^8$ and $R^9$ represent hydrogen;
$R^{10}$ represents chloro;
$R^{11}$ and $R^{12}$ represent hydrogen;
and salts thereof.

Likewise the invention relates to compounds of formula (I) wherein ring A represents ($A^1$);
W represents $CR^7$;
X represents $CR^5$;
Y represents O;
$R^0$ is ethoxy, 1-morpholinyl, 1-piperidinyl or 3,4-dehydro-1-piperidinyl;
$R^1$ is hydrogen;
$R^5$ and $R^6$ represent hydrogen;
$R^7$ represents hydrogen or fluoro;
$R^8$ and $R^9$ represent hydrogen;
$R^{10}$ represents hydroxy, lower alkoxy, allyloxy, benzyloxy, acetoxy, methoxymethyl or chloro;
$R^{11}$ and $R^{12}$ represent hydrogen;
and salts thereof.

Likewise the invention relates to compounds of formula (I) wherein ring A represents ($A^1$);
W represents $CR^7$;
X represents N;
Y represents O;
$R^0$ is 1-morpholinyl, 1-piperidinyl, 3-methyl-1-piperidinyl or 3,4-dehydro-1-piperidinyl;
$R^1$ is hydrogen;
$R^6$, $R^7$, $R^8$ and $R^9$ represent hydrogen;
$R^{10}$ represents methoxy;
$R^{11}$ and $R^{12}$ represent hydrogen;
and salts thereof.

Likewise the invention relates to compounds of formula (I) wherein ring A represents ($A^1$);
W represents $CR^7$;
X represents $CR^5$;
Y represents O;
$R^0$ is 1-morpholinyl or 3,4-dehydro-1-piperidinyl;
$R^1$ is amino;
$R^5$ and $R^6$ represent hydrogen;
$R^7$ represents fluoro;
$R^8$ and $R^9$ represent hydrogen;
$R^{10}$ represents chloro;
$R^{11}$ and $R^{12}$ represent hydrogen;
and salts thereof.

Likewise the invention relates to compounds of formula (I) wherein ring A represents ($A^4$);
W represents $CR^7$;
X represents $CR^5$;
Y represents S;
$R^0$ is $OCR^2R^3R^4$, 1-morpholinyl or 3,4-dehydro-1-piperidinyl
$R^1$ is amino;
$R^2$ is lower alkyl;
$R^3$, $R^4$, $R^5$ and $R^6$ represent hydrogen;
$R^7$ represents hydrogen or fluoro;
$R^8$ and $R^9$ represent hydrogen;
$R^{10}$ and $R^{11}$ represent methyl;
and salts thereof.

Another preferred group are compounds of formula (II) wherein ring A is selected from rings of formula ($A^1$), ($A^2$), ($A^3$), ($A^4$), ($A^5$), ($A^6$) and ($A^7$)
W represents $CR^7$;
X represents $CR^5$ or N;
Y represents O;
$R^0$ is $OR^2R^3R^4$;
$R^x$ is —(C═O)$R^1$ or cyano;

$R^1$ is hydrogen or $OR^{14}$;

$R^2$ is alkyl, halo-lower alkyl, hydroxy-lower alkyl, lower alkoxy-lower alkyl, lower alkoxy-lower alkoxy-lower alkyl, halo-lower alkoxy-lower alkyl, acyloxy-lower alkyl; amino-lower alkyl, wherein amino is unsubstituted or substituted by one or two substitutents selected from lower alkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl; cycloalkyl-lower alkyl, heterocyclyl-lower alkyl, optionally substituted phenyl-lower alkyl, optionally substituted heteroaryl-lower alkyl, optionally substituted alkenyl, optionally substituted alkinyl, cycloalkyl, optionally substituted phenyl, optionally substituted heteroaryl, halogen, cyano, carboxy, lower alkoxycarbonyl, lower alkoxy-lower alkoxycarbonyl; aminocarbonyl wherein amino is unsubstituted or substituted by one or two substitutents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl;

$R^3$ and $R^4$, independently of each other, are hydrogen, fluorine or lower alkyl;

$R^5$ and $R^6$ independently of each other, represent hydrogen, lower alkyl, halo-lower alkyl, lower alkoxy-lower alkyl, lower alkoxy-lower alkoxy-lower alkyl, halo-lower alkoxy-lower alkyl, optionally substituted alkenyl, optionally substituted alkinyl, aryl, heteroaryl, lower alkoxy, halo-lower alkoxy, lower alkoxy-lower alkoxy, alkenyloxy, alkinyloxy, lower alkylcarbonyl, optionally substituted phenylcarbonyl, carboxy, lower alkoxycarbonyl, lower alkoxy-lower alkoxycarbonyl; aminocarbonyl wherein amino is unsubstituted or substituted by one or two substitutents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; cyano, halogen, or nitro;

or $R^5$ and $R^6$ together with the atoms of the phenyl form a 5 or 6 membered carbocyclic or heterocyclic aromatic or aliphatic ring;

$R^7$ represents hydrogen, lower alkyl, halo-lower alkyl, hydroxy-lower alkyl, lower alkoxy-lower alkyl, aryloxy-lower alkyl, heteroaryloxy-lower alkyl, lower alkoxy-lower alkoxy-lower alkyl; aminoalkyl wherein amino is unsubstituted or substituted by one or two substitutents selected from lower alkyl, hydroxy-lower alkyl, alkoxy-lower alkyl, amino-lower alkyl, alkylcarbonyl, alkoxycarbonyl, aminoalkoxycarbonyl, alkoxyalkoxycarbonyl and aminocarbonyl; optionally substituted alkenyl, optionally substituted alkinyl, cycloalkyl, cycloalkyl-lower alkyl; aryl, heteroaryl, arylalkyl or heteroarylalkyl, wherein aryl or heteroaryl are unsubstituted or substituted by up to three substituents selected from lower alkyl, halo-lower alkyl, lower alkoxy, halogen, amino, cyano and nitro; lower alkoxy, halo-lower alkoxy, lower alkoxy-lower alkoxy, cycloalkyloxy, cycloalkyl-lower alkoxy, aryloxy, aryl-lower alkoxy, heteroaryloxy, heteroaryl-lower alkoxy, alkenyloxy, alkinyloxy, alkylmercapto, alkylsulfinyl, halo-lower alkylsulfinyl, alkylsulfonyl, arylsulfonyl, heteroarylsulfonyl, aminosulfonyl wherein amino is unsubstituted or substituted by one or two substitutents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; amino optionally substituted by one or two substitutents selected from lower alkyl, cycloalkyl, cycloalkyl-lower alkyl, hydroxy-lower alkyl, lower alkoxy-lower alkyl, di-lower alkylamino-lower alkyl, optionally substituted phenyl, optionally substituted phenyl-lower alkyl, optionally substituted heteroaryl, optionally substituted heteroaryl-lower alkyl, alkylcarbonyl, alkoxycarbonyl or aminocarbonyl, and wherein alkyl or lower alkyl in each case may be substituted by halogen, lower alkoxy, aryl, heteroaryl or optionally substituted amino, or wherein the two substituents on nitrogen form together with the nitrogen heterocyclyl; lower alkylcarbonyl, halo-lower alkylcarbonyl, optionally substituted phenylcarbonyl, carboxy, lower alkoxycarbonyl, lower alkoxy-lower alkoxycarbonyl; aminocarbonyl wherein amino is unsubstituted or substituted by one or two substitutents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; cyano, halogen, or nitro;

or $R^6$ and $R^7$ together with the atoms of the phenyl or pyridine ring form a 5 or 6 membered carbocyclic or heterocyclic aromatic or aliphatic ring;

$R^8$ represents hydrogen, lower alkyl, lower alkoxy or halogen;

or $R^7$ and $R^8$ together with the atoms of the phenyl or pyridine ring form a 5 or 6 membered carbocyclic or heterocyclic aromatic or aliphatic ring;

$R^9$, $R^{11}$ and $R^{12}$, independently of each other, represent hydrogen, lower alkyl, halo-lower alkyl, lower alkoxy-lower alkyl, lower alkoxy-lower alkoxy-lower alkyl, halo-lower alkoxy-lower alkyl, optionally substituted alkenyl, optionally substituted alkinyl, optionally substituted aryl, optionally substituted heteroaryl, lower alkoxy, halo-lower alkoxy, lower alkoxy-lower alkoxy, alkenyloxy, aryloxy, heteroaryloxy, alkylmercapto, alkylsulfinyl, halo-lower alkylsulfinyl, alkylsulfonyl, arylsulfonyl, heteroarylsulfonyl, lower alkylcarbonyl, optionally substituted phenylcarbonyl, carboxy, lower alkoxycarbonyl, lower alkoxy-lower alkoxycarbonyl; aminocarbonyl wherein amino is unsubstituted or substituted by one or two substitutents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; cyano, halogen, or nitro;

$R^{10}$ represents hydrogen, lower alkyl, halo-lower alkyl, hydroxy-lower alkyl, lower alkoxy-lower alkyl, aryloxy-lower alkyl, heteroaryloxy-lower alkyl, lower alkoxy-lower alkoxy-lower alkyl; aminoalkyl wherein amino is unsubstituted or substituted by one or two substitutents selected from lower alkyl, hydroxy-lower alkyl, alkoxy-lower alkyl, amino-lower alkyl, alkylcarbonyl, alkoxycarbonyl, aminoalkoxycarbonyl, alkoxyalkoxycarbonyl or aminocarbonyl; optionally substituted alkenyl, optionally substituted alkinyl, cycloalkyl, cycloalkyl-lower alkyl, aryl, heteroaryl; arylalkyl or heteroarylalkyl, wherein aryl or heteroaryl are unsubstituted or substituted by up to three substituents selected from lower alkyl, halo-lower alkyl, lower alkoxy, halogen, amino, cyano and nitro; lower alkoxy, halo-lower alkoxy, lower alkoxy-lower alkoxy, cycloalkyloxy, cycloalkyl-lower alkoxy, aryloxy, aryl-lower alkoxy, heteroaryloxy, heteroaryl-lower alkoxy, alkenyloxy, alkinyloxy, alkylmercapto, alkylsulfinyl, halo-lower alkylsulfinyl, alkylsulfonyl, arylsulfonyl, heteroarylsulfonyl; aminosulfonyl wherein amino is unsubstituted or substituted by one or two substitutents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; amino optionally substituted by one or two substitutents selected from lower alkyl, cycloalkyl, cycloalkyl-lower alkyl, hydroxy-lower alkyl, lower alkoxy-lower alkyl, di-lower alkylamino-lower alkyl, optionally substituted phenyl, optionally substituted phenyl-lower alkyl, optionally substituted heteroaryl, optionally substituted heteroaryl-lower alkyl, alkylcarbonyl, alkoxycarbonyl or aminocarbonyl, and wherein alkyl or lower alkyl in each case may be substituted by halogen, lower alkoxy, aryl, heteroaryl or optionally substituted amino, or wherein the two substituents on nitrogen form together with the nitrogen heterocyclyl; lower alkylcarbonyl, halo-lower alkylcarbonyl, optionally substituted phenylcarbonyl, carboxy, lower alkoxycarbonyl, lower alkoxy-lower alkoxycarbonyl; aminocarbonyl wherein amino is unsubstituted or substituted by one or two substituents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; cyano, halogen, or nitro;

or adjacent substitutents $R^9$ and $R^{10}$, or $R^{10}$ and $R^{11}$, or $R^{11}$ and $R^{12}$ together with the atoms of the phenyl, pyridine or pyridazine ring form a 5 or 6 membered carbocyclic or heterocyclic aromatic or aliphatic ring;

$R^{13}$ represents hydrogen, lower alkyl, halogen, aryl, optionally substituted alkylthio, or amino, unsubstituted or substituted by one or two substitutents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl;

$R^{14}$ represents hydrogen, lower alkyl, lower alkenyl, lower alkinyl, cycloalkyl-lower alkyl, halo-lower alkyl, hydroxy-lower alkyl, lower alkoxy-lower alkyl, acyloxy-lower alkyl, optionally substituted phenyl-lower alkyl, optionally substituted heteroaryl-lower alkyl, heterocyclyl-lower alkyl, optionally substituted phenyl, optionally substituted heteroaryl, or amino-lower alkyl, wherein amino may be substituted by one or two substituents selected from lower alkyl, cycloalkyl, cycloalkyl-lower alkyl, hydroxy-lower alkyl, lower alkoxy-lower alkyl, acyloxy-lower alkyl, acyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl;

and salts thereof.

In particular, the invention refers to compounds of formula (II) wherein
ring A is selected from rings of formula ($A^1$), ($A^2$), ($A^3$), ($A^4$), ($A^5$), ($A^6$) and ($A^7$);
W represents $CR^7$;
X represents $CR^5$ or N;
Y represents O;
$R^0$ is $OR^2R^3R^4$;
$R^x$ is —(C=O)$R^1$ or cyano;
$R^1$ is hydrogen or $OR^{14}$;
$R^2$ is alkyl, halo-lower alkyl, hydroxy-lower alkyl, lower alkoxy-lower alkyl, lower alkoxy-lower alkoxy-lower alkyl, halo-lower alkoxy-lower alkyl, acyloxy-lower alkyl, optionally substituted alkenyl, optionally substituted alkinyl, cycloalkyl, optionally substituted phenyl, optionally substituted heteroaryl, halogen, or cyano;
$R^3$ and $R^4$, independently of each other, are hydrogen, fluorine or lower alkyl;
$R^5$ and $R^6$ independently of each other, represent hydrogen, lower alkyl, halo-lower alkyl, lower alkoxy-lower alkyl, lower alkoxy-lower alkoxy-lower alkyl, halo-lower alkoxy-lower alkyl, optionally substituted alkenyl, optionally substituted alkinyl, aryl, heteroaryl, lower alkoxy, halo-lower alkoxy, lower alkoxy-lower alkoxy, alkenyloxy, alkinyloxy, lower alkylcarbonyl, optionally substituted phenylcarbonyl, carboxy, lower alkoxycarbonyl, lower alkoxy-lower alkoxycarbonyl; aminocarbonyl wherein amino is unsubstituted or substituted by one or two substitutents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; cyano, halogen, or nitro;

or $R^5$ and $R^6$ together with the atoms of the phenyl ring form a 5 or 6 membered carbocyclic or heterocyclic aromatic or aliphatic ring;

$R^7$ represents hydrogen, lower alkyl, halo-lower alkyl, hydroxy-lower alkyl, lower alkoxy-lower alkyl, aryloxy-lower alkyl, heteroaryloxy-lower alkyl, lower alkoxy-lower alkoxy-lower alkyl; aminoalkyl wherein amino is unsubstituted or substituted by one or two substituents selected from lower alkyl, hydroxy-lower alkyl, alkoxy-lower alkyl, amino-lower alkyl, alkylcarbonyl, alkoxycarbonyl, aminoalkoxycarbonyl, alkoxyalkoxycarbonyl and aminocarbonyl; optionally substituted alkenyl, optionally substituted alkinyl, cycloalkyl, cycloalkyl-lower alkyl; aryl, heteroaryl, arylalkyl or heteroarylalkyl, wherein aryl or heteroaryl are unsubstituted or substituted by up to three substituents selected from lower alkyl, halo-lower alkyl, lower alkoxy, halogen, amino, cyano and nitro; lower alkoxy, halo-lower alkoxy, lower alkoxy-lower alkoxy, cycloalkyloxy, cycloalkyl-lower alkoxy, aryloxy, aryl-lower alkoxy, heteroaryloxy, heteroaryl-lower alkoxy, alkenyloxy, alkinyloxy, alkylmercapto, alkylsulfinyl, halo-lower alkylsulfinyl, alkylsulfonyl, arylsulfonyl, heteroarylsulfonyl, aminosulfonyl wherein amino is unsubstituted or substituted by one or two substitutents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; amino optionally substituted by one or two substitutents selected from lower alkyl, cycloalkyl, cycloalkyl-lower alkyl, hydroxy-lower alkyl, lower alkoxy-lower alkyl, di-lower alkylamino-lower alkyl, optionally substituted phenyl, optionally substituted phenyl-lower alkyl, optionally substituted heteroaryl, optionally substituted heteroaryl-lower alkyl, alkylcarbonyl, alkoxycarbonyl or aminocarbonyl, and wherein alkyl or lower alkyl in each case may be substituted by halogen, lower alkoxy, aryl, heteroaryl or optionally substituted amino, or wherein the two substituents on nitrogen form together with the nitrogen heterocyclyl; lower alkylcarbonyl, halo-lower alkylcarbonyl, optionally substituted phenylcarbonyl, carboxy, lower alkoxycarbonyl, lower alkoxy-lower alkoxycarbonyl; aminocarbonyl wherein amino is unsubstituted or substituted by one or two substituents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; cyano, halogen, or nitro;

or $R^6$ and $R^7$ together with the atoms of the phenyl or pyridine ring form a 5 or 6 membered carbocyclic or heterocyclic aromatic or aliphatic ring;

$R^8$ represents hydrogen, lower alkyl, lower alkoxy or halogen;

or $R^7$ and $R^8$ together with the atoms of the phenyl or pyridine ring form a 5 or 6 membered carbocyclic or heterocyclic aromatic or aliphatic ring;

$R^9$, $R^{11}$ and $R^{12}$, independently of each other, represent hydrogen, lower alkyl, halo-lower alkyl, lower alkoxy-lower alkyl, lower alkoxy-lower alkoxy-lower alkyl, halo-lower alkoxy-lower alkyl, optionally substituted alkenyl, optionally substituted alkinyl, optionally substituted aryl, optionally substituted heteroaryl, lower alkoxy, halo-lower alkoxy, lower alkoxy-lower alkoxy, alkenyloxy, aryloxy, heteroaryloxy, alkylmercapto, alkylsulfinyl, halo-lower alkylsulfinyl, alkylsulfonyl, arylsulfonyl, heteroarylsulfonyl, lower alkylcarbonyl, optionally substituted phenylcarbonyl, carboxy, lower alkoxycarbonyl, lower alkoxy-lower alkoxycarbonyl; aminocarbonyl wherein amino is unsubstituted or substituted by one or two substituents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; cyano, halogen, or nitro;

$R^{10}$ represents hydrogen, lower alkyl, halo-lower alkyl, hydroxy-lower alkyl, lower alkoxy-lower alkyl, aryloxy-lower alkyl, heteroaryloxy-lower alkyl, lower alkoxy-lower alkoxy-lower alkyl; aminoalkyl wherein amino is unsubstituted or substituted by one or two substituents selected from lower alkyl, hydroxy-lower alkyl, alkoxy-lower alkyl, amino-lower alkyl, alkylcarbonyl, alkoxycarbonyl, aminoalkoxycarbonyl, alkoxyalkoxycarbonyl or aminocarbonyl; optionally substituted alkenyl, optionally substituted alkinyl, cycloalkyl, cycloalkyl-lower alkyl, aryl, heteroaryl; arylalkyl or heteroarylalkyl, wherein aryl or heteroaryl are unsubstituted or substituted by up to three substituents selected from lower alkyl, halo-lower alkyl, lower alkoxy, halogen, amino, cyano and nitro; lower alkoxy, halo-lower alkoxy, lower alkoxy-lower alkoxy, cycloalkyloxy, cycloalkyl-lower alkoxy, aryloxy, aryl-lower alkoxy, heteroaryloxy, heteroaryl-lower alkoxy, alkenyloxy, alkinyloxy, alkylmercapto, alkylsulfinyl, halo-lower alkylsulfinyl, alkylsulfonyl, arylsulfonyl, heteroarylsulfonyl; aminosulfonyl wherein amino is unsubstituted or substituted by one or two substituents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; amino optionally substituted by one or two substitutents selected from lower alkyl, cycloalkyl, cycloalkyl-lower alkyl, hydroxy-lower alkyl, lower alkoxy-lower alkyl, di-lower alkylamino-lower alkyl, optionally substituted phenyl, optionally substituted phenyl-lower alkyl, optionally substituted heteroaryl, optionally substituted heteroaryl-lower alkyl, alkylcarbonyl, alkoxycarbonyl or aminocarbonyl, and wherein alkyl or lower alkyl in each case may be substituted by halogen, lower alkoxy, aryl, heteroaryl or optionally substituted amino, or wherein the two substituents on nitrogen form together with the nitrogen heterocyclyl; lower alkylcarbonyl, halo-lower alkylcarbonyl, optionally substituted phenylcarbonyl, carboxy, lower alkoxycarbonyl, lower alkoxy-lower alkoxycarbonyl; aminocarbonyl wherein amino is unsubstituted or substituted by one or two substituents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; cyano, halogen, or nitro;

or adjacent substitutents $R^9$ and $R^{10}$, or $R^{10}$ and $R^{11}$, or $R^{11}$ and $R^{12}$ together with the atoms of the phenyl, pyridine or pyridazine ring form a 5 or 6 membered carbocyclic or heterocyclic aromatic or aliphatic ring;

$R^{13}$ represents hydrogen, lower alkyl, halogen, aryl, optionally substituted alkylthio, or amino, unsubstituted or substituted by one or two substituents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl;

$R^{14}$ represents hydrogen, lower alkyl, lower alkenyl, lower alkinyl, cycloalkyl-lower alkyl, halo-lower alkyl, hydroxy-lower alkyl, lower alkoxy-lower alkyl, acyloxy-lower alkyl, optionally substituted phenyl-lower alkyl, optionally substituted heteroaryl-lower alkyl, heterocyclyl-lower alkyl, optionally substituted phenyl, optionally substituted heteroaryl, or amino-lower alkyl, wherein amino may be substituted by one or two substituents selected from lower alkyl, cycloalkyl, cycloalkyl-lower alkyl, hydroxy-lower alkyl, lower alkoxy-lower alkyl, acyloxy-lower alkyl, acyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl;

and salts thereof.

More preferred are compounds of formula (II) wherein
ring A is selected from rings of formula ($A^1$), ($A^2$), ($A^3$), ($A^4$), ($A^5$), ($A^6$) and ($A^7$);
W represents $CR^7$;
X represents $CR^5$ or N;
Y represents O;
$R^0$ is $OR^2R^3R^4$;
$R^x$ is —(C═O)$R^1$ or cyano;
$R^1$ is hydrogen or $OR^{14}$;

$R^2$ is lower alkyl, halo-lower alkyl, optionally substituted alkenyl, optionally substituted alkinyl, cycloalkyl, halogen, or cyano;

$R^3$ and $R^4$, independently of each other, are hydrogen, fluorine or lower alkyl;

$R^5$ and $R^6$ independently of each other, represent hydrogen, lower alkyl, halo-lower alkyl, lower alkoxy-lower alkyl, lower alkoxy-lower alkoxy-lower alkyl, halo-lower alkoxy-lower alkyl, optionally substituted alkenyl, optionally substituted alkinyl, aryl, heteroaryl, lower alkoxy, halo-lower alkoxy, lower alkoxy-lower alkoxy, alkenyloxy, alkinyloxy, lower alkylcarbonyl, optionally substituted phenylcarbonyl, carboxy, lower alkoxycarbonyl, lower alkoxy-lower alkoxycarbonyl; aminocarbonyl wherein amino is unsubstituted or substituted by one or two substitutents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; cyano, halogen, or nitro;

or $R^5$ and $R^6$ together with the atoms of the phenyl ring form a 5 or 6 membered carbocyclic or heterocyclic aromatic or aliphatic ring;

$R^7$ represents hydrogen, lower alkyl, halo-lower alkyl, hydroxy-lower alkyl, lower alkoxy-lower alkyl, aryloxy-lower alkyl, heteroaryloxy-lower alkyl, lower alkoxy-lower alkoxy-lower alkyl; aminoalkyl wherein amino is unsubstituted or substituted by one or two substituents selected from lower alkyl, hydroxy-lower alkyl, alkoxy-lower alkyl, amino-lower alkyl, alkylcarbonyl, alkoxycarbonyl, aminoalkoxycarbonyl, alkoxyalkoxycarbonyl and aminocarbonyl; optionally substituted alkenyl, optionally substituted alkinyl, cycloalkyl, cycloalkyl-lower alkyl; aryl, heteroaryl, arylalkyl or heteroarylalkyl, wherein aryl or heteroaryl are unsubstituted or substituted by up to three substituents selected from lower alkyl, halo-lower alkyl, lower alkoxy, halogen, amino, cyano and nitro; lower alkoxy, halo-lower alkoxy, lower alkoxy-lower alkoxy, cycloalkyloxy, cycloalkyl-lower alkoxy, aryloxy, aryl-lower alkoxy, heteroaryloxy, heteroaryl-lower alkoxy, alkenyloxy, alkinyloxy, alkylmercapto, alkylsulfinyl, halo-lower alkylsulfinyl, alkylsulfonyl, arylsulfonyl, heteroarylsulfonyl, aminosulfonyl wherein amino is unsubstituted or substituted by one or two substituents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; amino optionally substituted by one or two substitutents selected from lower alkyl, cycloalkyl, cycloalkyl-lower alkyl, hydroxy-lower alkyl, lower alkoxy-lower alkyl, di-lower alkylamino-lower alkyl, optionally substituted phenyl, optionally substituted phenyl-lower alkyl, optionally substituted heteroaryl, optionally substituted heteroaryl-lower alkyl, alkylcarbonyl, alkoxycarbonyl or aminocarbonyl, and wherein alkyl or lower alkyl in each case may be substituted by halogen, lower alkoxy, aryl, heteroaryl or optionally substituted amino, or wherein the two substituents on nitrogen form together with the nitrogen heterocyclyl; lower alkylcarbonyl, halo-lower alkylcarbonyl, optionally substituted phenylcarbonyl, carboxy, lower alkoxycarbonyl, lower alkoxy-lower alkoxycarbonyl; aminocarbonyl wherein amino is unsubstituted or substituted by one or two substitutents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; cyano, halogen, or nitro;

or $R^6$ and $R^7$ together with the atoms of the phenyl or pyridine ring form a 5 or 6 membered carbocyclic or heterocyclic aromatic or aliphatic ring;

$R^8$ represents hydrogen, lower alkyl, lower alkoxy or halogen; or $R^7$ and $R^8$ together with the atoms of the phenyl or pyridine ring form a 5 or 6 membered carbocyclic or heterocyclic aromatic or aliphatic ring;

$R^9$, $R^{11}$ and $R^{12}$, independently of each other, represent hydrogen, lower alkyl, halo-lower alkyl, lower alkoxy-lower alkyl, lower alkoxy-lower alkoxy-lower alkyl, halo-lower alkoxy-lower alkyl, optionally substituted alkenyl, optionally substituted alkinyl, optionally substituted aryl, optionally substituted heteroaryl, lower alkoxy, halo-lower alkoxy, lower alkoxy-lower alkoxy, alkenyloxy, aryloxy, heteroaryloxy, alkylmercapto, alkylsulfinyl, halo-lower alkylsulfinyl, alkylsulfonyl, arylsulfonyl, heteroarylsulfonyl, lower alkylcarbonyl, optionally substituted phenylcarbonyl, carboxy, lower alkoxycarbonyl, lower alkoxy-lower alkoxycarbonyl; aminocarbonyl wherein amino is unsubstituted or substituted by one or two substitutents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; cyano, halogen, or nitro;

$R^{10}$ represents hydrogen, lower alkyl, halo-lower alkyl, hydroxy-lower alkyl, lower alkoxy-lower alkyl, aryloxy-lower alkyl, heteroaryloxy-lower alkyl, lower alkoxy-lower alkoxy-lower alkyl; aminoalkyl wherein amino is unsubstituted or substituted by one or two substituents selected from lower alkyl, hydroxy-lower alkyl, alkoxy-lower alkyl, amino-lower alkyl, alkylcarbonyl, alkoxycarbonyl, aminoalkoxycarbonyl, alkoxyalkoxycarbonyl or aminocarbonyl; optionally substituted alkenyl, optionally substituted alkinyl, cycloalkyl, cycloalkyl-lower alkyl, aryl, heteroaryl; arylalkyl or heteroarylalkyl, wherein aryl or heteroaryl are unsubstituted or substituted by up to three substituents selected from lower alkyl, halo-lower alkyl, lower alkoxy, halogen, amino, cyano and nitro; lower alkoxy, halo-lower alkoxy, lower alkoxy-lower alkoxy, cycloalkyloxy, cycloalkyl-lower alkoxy, aryloxy, aryl-lower alkoxy, heteroaryloxy, heteroaryl-lower alkoxy, alkenyloxy, alkinyloxy, alkylmercapto, alkylsulfinyl, halo-lower alkylsulfinyl, alkylsulfonyl, arylsulfonyl, heteroarylsulfonyl; aminosulfonyl wherein amino is unsubstituted or substituted by one or two substitutents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; amino optionally substituted by one or two substitutents selected from lower alkyl, cycloalkyl, cycloalkyl-lower alkyl, hydroxy-lower alkyl, lower alkoxy-lower alkyl, di-lower alkylamino-lower alkyl, optionally substituted phenyl, optionally substituted phenyl-lower alkyl, optionally substituted heteroaryl, optionally substituted heteroaryl-lower alkyl, alkylcarbonyl, alkoxycarbonyl or aminocarbonyl, and wherein alkyl or lower alkyl in each case may be substituted by halogen, lower alkoxy, aryl, heteroaryl or optionally substituted amino, or wherein the two substituents on nitrogen form together with the nitrogen heterocyclyl; lower alkylcarbonyl, halo-lower alkylcarbonyl, optionally substituted phenylcarbonyl, carboxy, lower alkoxycarbonyl, lower alkoxy-lower alkoxycarbonyl; aminocarbonyl wherein amino is unsubstituted or substituted by one or two substitutents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; cyano, halogen, or nitro;

or adjacent substitutents $R^9$ and $R^{10}$, or $R^{10}$ and $R^{11}$, or $R^{11}$ and $R^{12}$ together with the atoms of the phenyl, pyridine or pyridazine ring form a 5 or 6 membered carbocyclic or heterocyclic aromatic or aliphatic ring;

$R^{13}$ represents hydrogen, lower alkyl, halogen, aryl, optionally substituted alkylthio, or amino, unsubstituted or substituted by one or two substitutents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl;

$R^{14}$ represents hydrogen, lower alkyl, halo-lower alkyl, hydroxy-lower alkyl, lower alkoxy-lower alkyl, acyloxy-lower alkyl, optionally substituted phenyl-lower alkyl, optionally substituted heteroaryl-lower alkyl, heterocyclyl-lower alkyl, or amino-lower alkyl, wherein amino may be substituted by one or two substituents selected from lower alkyl, cycloalkyl, cycloalkyl-lower alkyl, hydroxy-lower alkyl, lower alkoxy-lower alkyl, acyloxy-lower alkyl, acyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl;

and salts thereof.

Particularly preferred are compounds of formula (II) wherein ring A is selected from rings of formula $(A^1)$, $(A^3)$ and $(A^4)$;

W represents $CR^7$;
X represents $CR^5$ or N;
Y represents O;
$R^0$ is $OR^2R^3R^4$;
$R^x$ is —(C═O)$R^1$ or cyano;
$R^1$ is $OR^{14}$;
$R^2$ is lower alkyl, halo-lower alkyl, optionally substituted alkenyl, optionally substituted alkinyl, cycloalkyl, halogen, or cyano;

$R^3$ and $R^4$, independently of each other, are hydrogen, fluorine or lower alkyl;

$R^5$ and $R^6$ independently of each other, represent hydrogen, lower alkyl, halo-lower alkyl, lower alkoxy-lower alkyl, lower alkoxy-lower alkoxy-lower alkyl, halo-lower alkoxy-lower alkyl, optionally substituted alkenyl, optionally substituted alkinyl, aryl, heteroaryl, lower alkoxy, halo-lower alkoxy, lower alkoxy-lower alkoxy, alkenyloxy, alkinyloxy, lower alkylcarbonyl, optionally substituted phenylcarbonyl, carboxy, lower alkoxycarbonyl, lower alkoxy-lower alkoxycarbonyl; aminocarbonyl wherein amino is unsubstituted or substituted by one or two substitutents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; cyano, halogen, or nitro;

or $R^5$ and $R^6$ together with the atoms of the phenyl ring form a 5 or 6 membered carbocyclic or heterocyclic aromatic or aliphatic ring;

$R^7$ represents hydrogen, lower alkyl, halo-lower alkyl, hydroxy-lower alkyl, lower alkoxy-lower alkyl, aryloxy-lower alkyl, heteroaryloxy-lower alkyl, lower alkoxy-lower alkoxy-lower alkyl; aminoalkyl wherein amino is unsubstituted or substituted by one or two substituents selected from lower alkyl, hydroxy-lower alkyl, alkoxy-lower alkyl, amino-lower alkyl, alkylcarbonyl, alkoxycarbonyl, aminoalkoxycarbonyl, alkoxyalkoxycarbonyl and aminocarbonyl; optionally substituted alkenyl, optionally substituted alkinyl, cycloalkyl, cycloalkyl-lower alkyl; aryl, heteroaryl, arylalkyl or heteroarylalkyl, wherein aryl or heteroaryl are unsubstituted or substituted by up to three substituents selected from lower alkyl, halo-lower alkyl, lower alkoxy, halogen, amino, cyano and nitro; lower alkoxy, halo-lower alkoxy, lower alkoxy-lower alkoxy, cycloalkyloxy, cycloalkyl-lower alkoxy, aryloxy, aryl-lower alkoxy, heteroaryloxy, heteroaryl-lower alkoxy, alkenyloxy, alkinyloxy, alkylmercapto, alkylsulfinyl, halo-lower alkylsulfinyl, alkylsulfonyl, arylsulfonyl, heteroarylsulfonyl, aminosulfonyl wherein amino is unsubstituted or substituted by one or two substitutents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; amino optionally substituted by one or two substitutents selected from lower alkyl, cycloalkyl, cycloalkyl-lower alkyl, hydroxy-lower alkyl, lower alkoxy-lower alkyl, di-lower alkylamino-lower alkyl, optionally substituted phenyl, optionally substituted phenyl-lower alkyl, optionally substituted heteroaryl, optionally substituted heteroaryl-lower alkyl, alkylcarbonyl, alkoxycarbonyl or aminocarbonyl, and wherein alkyl or lower alkyl in each case may be substituted by halogen, lower alkoxy, aryl, heteroaryl or optionally substituted amino, or wherein the two substituents on nitrogen form together with the nitrogen heterocyclyl; lower alkylcarbonyl, halo-lower alkylcarbonyl, optionally substituted phenylcarbonyl, carboxy, lower alkoxycarbonyl, lower alkoxy-lower alkoxycarbonyl; aminocarbonyl wherein amino is unsubstituted or substituted by one or two substitutents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; cyano, halogen, or nitro;

or $R^6$ and $R^7$ together with the atoms of the phenyl or pyridine ring form a 5 or 6 membered carbocyclic or heterocyclic aromatic or aliphatic ring;

$R^8$ represents hydrogen, lower alkyl, lower alkoxy or halogen;

or $R^7$ and $R^8$ together with the atoms of the phenyl or pyridine ring form a 5 or 6 membered carbocyclic or heterocyclic aromatic or aliphatic ring;

$R^9$, $R^{11}$ and $R^{12}$, independently of each other, represent hydrogen, lower alkyl, halo-lower alkyl, lower alkoxy-lower alkyl, lower alkoxy-lower alkoxy-lower alkyl, halo-lower alkoxy-lower alkyl, optionally substituted alkenyl, optionally substituted alkinyl, optionally substituted aryl, optionally substituted heteroaryl, lower alkoxy, halo-lower alkoxy, lower alkoxy-lower alkoxy, alkenyloxy, aryloxy, heteroaryloxy, alkylmercapto, alkylsulfinyl, halo-lower alkylsulfinyl, alkylsulfonyl, arylsulfonyl, heteroarylsulfonyl, lower alkylcarbonyl, optionally substituted phenylcarbonyl, carboxy, lower alkoxycarbonyl, lower alkoxy-lower alkoxycarbonyl; aminocarbonyl wherein amino is unsubstituted or substituted by one or two substitutents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; cyano, halogen, or nitro;

$R^{10}$ represents hydrogen, lower alkyl, halo-lower alkyl, hydroxy-lower alkyl, lower alkoxy-lower alkyl, aryloxy-lower alkyl, heteroaryloxy-lower alkyl, lower alkoxy-lower alkoxy-lower alkyl; aminoalkyl wherein amino is unsubstituted or substituted by one or two substituents selected from lower alkyl, hydroxy-lower alkyl, alkoxy-lower alkyl, amino-lower alkyl, alkylcarbonyl, alkoxycarbonyl, aminoalkoxycarbonyl, alkoxyalkoxycarbonyl or aminocarbonyl; optionally substituted alkenyl, optionally substituted alkinyl, cycloalkyl, cycloalkyl-lower alkyl, aryl, heteroaryl; arylalkyl or heteroarylalkyl, wherein aryl or heteroaryl are unsubstituted or substituted by up to three substituents selected from lower alkyl, halo-lower alkyl, lower alkoxy, halogen, amino, cyano and nitro; lower alkoxy, halo-lower alkoxy, lower alkoxy-lower alkoxy, cycloalkyloxy, cycloalkyl-lower alkoxy, aryloxy, aryl-lower alkoxy, heteroaryloxy, heteroaryl-lower alkoxy, alkenyloxy, alkinyloxy, alkylmercapto, alkylsulfinyl, halo-lower alkylsulfinyl, alkylsulfonyl, arylsulfonyl, heteroarylsulfonyl; aminosulfonyl wherein amino is unsubstituted or substituted by one or two substitutents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; amino optionally substituted by one or two substitutents selected from lower alkyl, cycloalkyl, cycloalkyl-lower alkyl, hydroxy-lower alkyl, lower alkoxy-lower alkyl, di-lower alkylamino-lower alkyl, optionally substituted phenyl, optionally substituted phenyl-lower alkyl, optionally substituted heteroaryl, optionally substituted heteroaryl-lower alkyl, alkylcarbonyl, alkoxycarbonyl or aminocarbonyl, and wherein alkyl or lower alkyl in each case may be substituted by halogen, lower alkoxy, aryl, heteroaryl or optionally substituted amino, or wherein the two substituents on nitrogen form together with the nitrogen heterocyclyl; lower alkylcarbonyl, halo-lower alkylcarbonyl, optionally substituted phenylcarbonyl, carboxy, lower alkoxycarbonyl, lower alkoxy-lower alkoxycarbonyl; aminocarbonyl wherein amino is unsubstituted or substituted by one or two substitutents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; cyano, halogen, or nitro;

or adjacent substitutents $R^9$ and $R^{10}$, or $R^{10}$ and $R^{11}$, or $R^{11}$ and $R^{12}$ together with the atoms of the phenyl, pyridine or pyridazine ring form a 5 or 6 membered carbocyclic or heterocyclic aromatic or aliphatic ring;

$R^{13}$ represents, hydrogen, lower alkyl, halogen, aryl, optionally substituted alkylthio, or amino, unsubstituted or substituted by one or two substitutents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl;

$R^{14}$ represents lower alkyl, hydroxy-lower alkyl, lower alkoxy-lower alkyl, acyloxy-lower alkyl, optionally substituted phenyl-lower alkyl, optionally substituted heteroaryl-lower alkyl, heterocyclyl-lower alkyl, or amino-lower alkyl, wherein amino may be substituted by lower alkyl, hydroxy-lower alkyl, lower alkoxy-lower alkyl, acyloxy-lower alkyl, acyl, optionally substituted phenyl-lower alkyl, or optionally substituted heteroaryl-lower alkyl, or wherein the two substituents on nitrogen form together with the nitrogen heterocyclyl;

and salts thereof.

More preferred are compounds of formula (II) wherein ring A is selected from rings of formula ($A^1$), ($A^3$) and ($A^4$);

W represents $CR^7$;
X represents $CR^5$ or N;
Y represents O;
$R^0$ is $OR^2R^3R^4$;
$R^x$ is —(C=O)$R^1$ or cyano;
$R^1$ is $OR^{14}$;
$R^2$ is lower alkyl, alkenyl, alkinyl, cycloalkyl, halogen, or cyano;
$R^3$ and $R^4$, independently of each other, are hydrogen, fluorine or lower alkyl;
$R^5$ and $R^6$ independently of each other, represent hydrogen, lower alkyl, halo-lower alkyl, lower alkoxy-lower alkyl, optionally substituted alkenyl, optionally substituted alkinyl, aryl, heteroaryl, lower alkoxy, lower alkoxy-lower alkoxy, alkenyloxy, alkinyloxy, lower alkylcarbonyl, optionally substituted phenylcarbonyl, carboxy, lower alkoxycarbonyl, lower alkoxy-lower alkoxycarbonyl, cyano, halogen, or nitro;
or $R^5$ and $R^6$ together with the atoms of the phenyl form a 5 or 6 membered carbocyclic or heterocyclic aromatic or aliphatic ring;
$R^7$ represents hydrogen, lower alkyl, halo-lower alkyl, hydroxy-lower alkyl, lower alkoxy-lower alkyl, aryloxy-lower alkyl, heteroaryloxy-lower alkyl, lower alkoxy-lower alkoxy-lower alkyl; aminoalkyl wherein amino is unsubstituted or substituted by one or two substituents selected from lower alkyl, hydroxy-lower alkyl, alkoxy-lower alkyl, amino-lower alkyl, alkylcarbonyl, alkoxycarbonyl, aminoalkoxycarbonyl, alkoxyalkoxycarbonyl and aminocarbonyl; optionally substituted alkenyl, optionally substituted alkinyl, cycloalkyl, cycloalkyl-lower alkyl; aryl, heteroaryl, arylalkyl or heteroarylalkyl, wherein aryl or heteroaryl are unsubstituted or substituted by up to three substituents selected from lower alkyl, halo-lower alkyl, lower alkoxy, halogen, amino, cyano and nitro; lower alkoxy, halo-lower alkoxy, lower alkoxy-lower alkoxy, cycloalkyloxy, cycloalkyl-lower alkoxy, aryloxy, aryl-lower alkoxy, heteroaryloxy, heteroaryl-lower alkoxy, alkenyloxy, alkinyloxy, alkylmercapto, alkylsulfinyl, halo-lower alkylsulfinyl, alkylsulfonyl, arylsulfonyl, heteroarylsulfonyl, aminosulfonyl wherein amino is unsubstituted or substituted by one or two substitutents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; amino optionally substituted by one or two substituents selected from lower alkyl, cycloalkyl, cycloalkyl-lower alkyl, hydroxy-lower alkyl, lower alkoxy-lower alkyl, di-lower alkylamino-lower alkyl, optionally substituted phenyl, optionally substituted phenyl-lower alkyl, optionally substituted heteroaryl, optionally substituted heteroaryl-lower alkyl, alkylcarbonyl, alkoxycarbonyl or aminocarbonyl, and wherein alkyl or lower alkyl in each case may be substituted by halogen, lower alkoxy, aryl, heteroaryl or optionally substituted amino, or wherein the two substituents on nitrogen form together with the nitrogen heterocyclyl; lower alkylcarbonyl, halo-lower alkylcarbonyl, optionally substituted phenylcarbonyl, carboxy, lower alkoxycarbonyl, lower alkoxy-lower alkoxycarbonyl; aminocarbonyl wherein amino is unsubstituted or substituted by one or two substituents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; cyano, halogen, or nitro;

or $R^6$ and $R^7$ together with the atoms of the phenyl or pyridine ring form a 5 or 6 membered carbocyclic or heterocyclic aromatic or aliphatic ring;

$R^8$ represents hydrogen;

$R^9$, $R^{11}$ and $R^{12}$, independently of each other, represent hydrogen, lower alkyl, halo-lower alkyl, lower alkoxy-lower alkyl, lower alkoxy-lower alkoxy-lower alkyl, halo-lower alkoxy-lower alkyl, optionally substituted alkenyl, optionally substituted alkinyl, optionally substituted aryl, optionally substituted heteroaryl, lower alkoxy, halo-lower alkoxy, lower alkoxy-lower alkoxy, alkenyloxy, aryloxy, heteroaryloxy, alkylmercapto, alkylsulfinyl, halo-lower alkylsulfinyl, alkylsulfonyl, arylsulfonyl, heteroarylsulfonyl, lower alkylcarbonyl, optionally substituted phenylcarbonyl, carboxy, lower alkoxycarbonyl, lower alkoxy-lower alkoxycarbonyl; aminocarbonyl wherein amino is unsubstituted or substituted by one or two substituents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; cyano, halogen, or nitro;

$R^{10}$ represents hydrogen, lower alkyl, halo-lower alkyl, hydroxy-lower alkyl, lower alkoxy-lower alkyl, lower alkoxy-lower alkoxy-lower alkyl; aminoalkyl wherein amino is unsubstituted or substituted by one or two substituents selected from lower alkyl, hydroxy-lower alkyl, alkoxy-lower alkyl, amino-lower alkyl, alkylcarbonyl, alkoxycarbonyl, aminoalkoxycarbonyl, alkoxyalkoxycarbonyl or aminocarbonyl; optionally substituted alkenyl, optionally substituted alkinyl, cycloalkyl, cycloalkyl-lower alkyl, aryl, heteroaryl; arylalkyl or heteroarylalkyl, wherein aryl or heteroaryl are unsubstituted or substituted by up to three substituents selected from lower alkyl, halo-lower alkyl, lower alkoxy, halogen, amino, cyano and nitro; lower alkoxy, halo-lower alkoxy, lower alkoxy-lower alkoxy, cycloalkyloxy, cycloalkyl-lower alkoxy, aryloxy, aryl-lower alkoxy, heteroaryloxy, heteroaryl-lower alkoxy, alkenyloxy, alkinyloxy; amino optionally substituted by one or two substituents selected from lower alkyl, cycloalkyl, cycloalkyl-lower alkyl, hydroxy-lower alkyl, lower alkoxy-lower alkyl, di-lower alkylamino-lower alkyl, optionally substituted phenyl, optionally substituted phenyl-lower alkyl, optionally substituted heteroaryl, optionally substituted heteroaryl-lower alkyl, alkylcarbonyl, alkoxycarbonyl or aminocarbonyl, and wherein alkyl or lower alkyl in each case may be substituted by halogen, lower alkoxy, aryl, heteroaryl or optionally substituted amino, or wherein the two substituents on nitrogen form together with the nitrogen heterocyclyl; lower alkylcarbonyl, halo-lower alkylcarbonyl, optionally substituted phenylcarbonyl, carboxy, lower alkoxycarbonyl, lower alkoxy-lower alkoxycarbonyl; aminocarbonyl wherein amino is unsubstituted or substituted by one or two substituents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; cyano, halogen, or nitro;

$R^{13}$ represents hydrogen, lower alkyl, halogen, aryl, optionally substituted alkylthio, or amino, unsubstituted or substituted by one or two substituents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl;

$R^{14}$ represents lower alkyl, hydroxy-lower alkyl, lower alkoxy-lower alkyl, acyloxy-lower alkyl, optionally substituted phenyl-lower alkyl, optionally substituted heteroaryl-lower alkyl, heterocyclyl-lower alkyl, or amino-lower alkyl, wherein amino may be substituted by lower alkyl, hydroxy-lower alkyl, lower alkoxy-lower alkyl, acyloxy-lower alkyl, acyl, optionally substituted phenyl-lower alkyl, or optionally substituted heteroaryl-lower alkyl, or wherein the two substituents on nitrogen form together with the nitrogen heterocyclyl;

and salts thereof.

More preferred are compounds of formula (II) wherein
A is selected from rings of formula ($A^1$), ($A^3$) and ($A^4$);
W represents $CR^7$;
X represents $CR^5$;
Y represents O;
$R^0$ is $OR^2R^3R^4$;
$R^x$ is cyano;
$R^2$ is lower alkyl;
$R^3$ is hydrogen;
$R^4$ is hydrogen;
$R^5$ and $R^6$ independently of each other, represent hydrogen, lower alkyl, halo-lower alkyl, lower alkoxy, lower alkoxy-lower alkoxy, cyano, halogen, or nitro;

or $R^5$ and $R^6$ together with the atoms of the phenyl form a 5 or 6 membered carbocyclic or heterocyclic aromatic or aliphatic ring;

$R^7$ represents hydrogen, lower alkyl, lower alkoxy, amino, optionally substituted by lower alkyl, alkylcarbonyl, alkoxycarbonyl or aminocarbonyl, carboxy, lower alkoxycarbonyl, aminocarbonyl, cyano, halogen, or nitro;

$R^8$ represents hydrogen;
$R^9$ represent hydrogen;
$R^{10}$ represents hydrogen or halogen;

$R^{11}$ represents hydrogen, lower alkyl, lower alkoxy, lower alkoxy-lower alkoxy, or halogen;

$R^{12}$ represents hydrogen or lower alkyl;

$R^{13}$ represents hydrogen, lower alkyl, halogen, aryl, optionally substituted alkylthio, or amino, unsubstituted or substituted by one or two substitutents selected from lower alkyl, or wherein the two substituents on nitrogen form together with the nitrogen heterocyclyl;

$R^{14}$ represents lower alkyl;

and salts thereof.

Most preferred are the compounds of the Examples, especially the compounds of Examples 2, 3, 4, 12, 14, 16, 17, 18, 27, 29, 31, 37, 38, 39, 47, 48, 53, 54, 56, 57, 58, 61, 62, 63, 64, 65, 66, 67, 68, 75, 78, 82, 87, 88, 91, 93, 95, 96, 98, 103, 107, 108, 111, 112, 118, 119, 133, 134, and 135.

Likewise preferred are compounds of formula (II), which carry substituents corresponding to the substituents of the most preferred examples listed hereinbefore, and which can be regarded as pro-drugs since they form such compounds of formula (I) through cyclization in vitro or in vivo in a process A), D) or G) explained hereinbelow.

Especially, the invention relates to the use of a compound of formula (I), a compound of formula (II), a pro-drug or a pharmaceutically acceptable salt of such compounds for the preparation of a pharmaceutical composition for the treatment of a neoplastic disease, autoimmune disease, transplantation related pathology and/or degenerative disease.

Furthermore, the invention provides a method for the treatment of a neoplastic disease, autoimmune disease, transplantation related pathology and/or degenerative disease, which comprises administering a compound of formula (I), a compound of formula (II), a pro-drug or a pharmaceutically acceptable salt thereof, wherein the radicals and symbols have the meanings as defined above, in a quantity effective against said disease, to a warm-blooded animal requiring such treatment.

METHOD OF PREPARATION

A compound of the invention may be prepared by processes that, though not applied hitherto for the new compounds of the present invention, are known per se, in particular A) for the preparation of a compound of formula (I) wherein $R^1$ is amino $NHR^{15}$ and $R^{15}$ is hydrogen, a process wherein an ω-(o-cyano)phenoxyacetophenone or corresponding heterocyclic compound of formula (II)

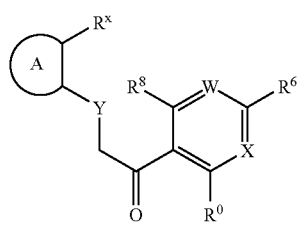
(II)

wherein A, W, X, $R^0$, $R^6$ and $R^8$ have the meaning as defined in formula (I) and $R^x$ is cyano, is cyclised in the presence of a base;

B) for the preparation of a compound of formula (I) wherein $R^0$ is $OCR^2R^3R^4$, a process wherein a phenolic compound of formula (III)

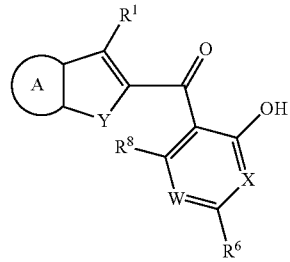
(III)

wherein A, W, X, Y, $R^1$, $R^6$ and $R^8$ have the meaning as defined in formula (I), is treated with an etherifying agent of formula (IV)

$$R^2R^3R^4C\text{—}Z \qquad (IV)$$

wherein $R^2$, $R^3$ and $R^4$ have the meaning as defined in formula (I) and Z is a leaving group;

C) for the preparation of a compound of formula (I), a process wherein a halo compound of formula (V)

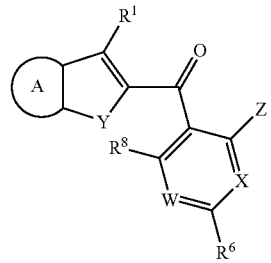
(V)

wherein A, Y, X, W, $R^1$, $R^6$ and $R^8$ have the meaning as defined in formula (I) and Z is halogen or another leaving group, Ca) in case X and/or W is N and Z is bromo, chloro, fluoro or a sulfonate, is treated with an alcohol of formula $R^2R^3R^4C\text{—}OH$ (VIa) in the presence of a strong base to give a compound wherein $R^0$ is $OCR^2R^3R^4$ and $R^2$, $R^3$ and $R^4$ have the meaning as defined in formula (I), Cb) in case Z is fluoro; or Z is bromo or chloro and X and/or W is N; is treated with an amine of formula $R^{16}R^{17}NH$ (VIb) to give a compound wherein $R^0$ is $NR^{16}R^{17}$ and $R^{16}$ and $R^{17}$ have the meaning as defined in formula (I), Cc) in case Z is iodo, bromo, chloro or sulfonate, is treated with an amine of formula $R^{16}R^{17}NH$ (VIb) in the presence of a palladium catalyst to give a compound wherein $R^0$ is $NR^{16}R^{17}$ and $R^{16}$ and $R^{17}$ have the meaning as defined in formula (I), Cd) in case Z is iodo, bromo, chloro or sulfonate, is treated with a compound of formula $R^0$-L (VIc) in the presence of a catalyst, wherein $R^0$ is as defined in formula (I) other than $OCR^2R^3R^4$ and $NR^{16}R^{17}$, and L is a reactive functional group;

D) for the preparation of a compound of formula (I) wherein $R^1$ is $OR^{14}$ and $R^{14}$ is hydrogen, a process wherein an ω-(o-alkoxycarbonyl)phenoxyacetophenone or corresponding heterocyclic compound of formula (II)

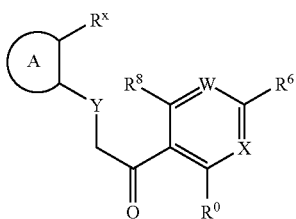

(II)

wherein A, W, X, R⁰, R⁶ and R⁸ have the meaning as defined in formula (I), R^x is —(C=O)OR¹⁴ and R¹⁴ is alkyl or substituted alkyl, is cyclised in the presence of a base; or E) for the preparation of a compound of formula (I) wherein Y is O, R¹ is OR¹⁴ and R¹⁴ is hydrogen, a process wherein an ortho-substituted aryl benzoate or corresponding heterocyclic compound of formula (VIII)

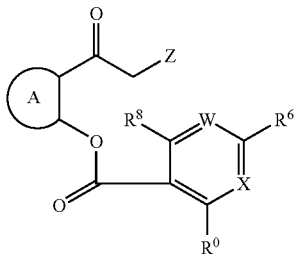

(VIII)

wherein A, W, X, R⁰, R⁶ and R⁸ have the meaning as defined in formula (I) and Z is a leaving group, is cyclised in the presence of a strong base;

F) for the preparation of a compound of formula (I) wherein Y is O, R¹ is OR¹⁴ and R¹⁴ is hydrogen, a process wherein a diketone of formula (IX)

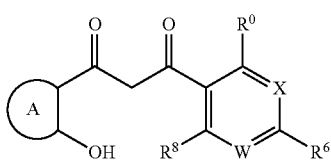

(IX)

wherein A, W, X, R⁰, R⁶ and R⁸ have the meaning as defined in formula (I), is cyclised by halogenation in the presence of a base;

G) for the preparation of a compound of formula (I) wherein R¹ is hydrogen, a process wherein an ω-(o-formyl) phenoxyacetophenone or corresponding heterocyclic compound of formula (II)

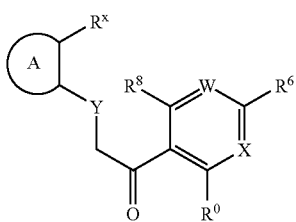

(II)

wherein A, W, X, R⁰, R⁶ and R⁸ have the meaning as defined in formula (I), R^x is —(C=O)R¹ and R¹ is hydrogen, is cyclised in the presence of a base;

H) for the preparation of a compound of formula (II), a process wherein an o-substituted phenol or thiophenol of formula (VII)

(VII)

wherein A, Y and R^x has the meaning as defined in formula (II), is reacted with a compound of formula (X)

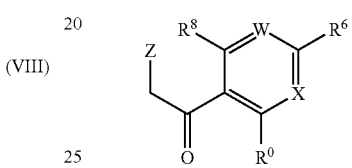

(X)

wherein W, X, R⁰, R⁶ and R⁸ have the meaning as defined in formula (II) and Z is a leaving group, and, if so desired, an obtainable compound of formula (I) or of formula (II) is converted into another compound of formula (I) or of formula (II), a free compound of formula (I) or of formula (II) is converted into a salt, an obtainable salt of a compound of formula (I) or of formula (II) is converted into the free compound or another salt, and/or a mixture of isomeric compounds of formula (I) or of formula (II) is separated into the individual isomers.

A suitable base for the cyclization reaction in methods A), D) and G) is e.g. an aqueous buffer solution of pH 7 and above, a metal carbonate or bicarbonate such as potassium carbonate or cesium carbonate, a metal hydroxide such as lithium hydroxide or sodium hydroxide, a metal alcoholate such as sodium methoxide or potassium tert-butoxide, a tertiary amine such as diisopropylethylamine or pyridine, a metal amide such as lithium diisopropylamide, or a phosphazene base such as tert-butylimino-tris(dimethylamino)-phosphorane.

Method B) is a transformation usually referred to as Williamson ether synthesis and is achieved under reaction conditions typical for this reaction. Leaving groups Z considered are e.g. halogen, such as chloro or bromo, and sulfonates, e.g. p-toluenesulfonate.

Strong bases considered in method Ca) are e.g. metal amides or phosphazene bases, or also alcoholates which convert the alcohol of formula (VIa) to the corresponding anion, but is less reactive than the anion derived from alcohol (VIa). Preferably the alcohol of formula (VIa) is first converted into the corresponding alcoholate, e.g. with sodium hydride, butyllithium or lithium diisopropylamide.

For the introduction of an amino function in method Cb) with an amine of formula (VIb), the reaction is usually performed without base, but can also be reacted in the presence of a suitable tertiary amine, e.g. dimethylaminopyridine, diisopropyl-ethylamine or 1,4-diaza[2.2.2]bicyclooctane. It may be emphasized that in case of R⁷ and Z both representing fluorine, Z can be replaced regioselectively.

The introduction of an amino function in method Cc) is referred to as Buchwald-Hartwig amination. The reaction is preferably carried out in an unpolar aprotic solvent in the presence of a soluble palladium catalyst comprising an appropriate ligand. A particularly useful catalyst is palladium bis-dibenzylideneacetone, Pd(dba)$_2$. The reactivity of the palladium catalyst can be tuned by the choice of the ligand.

For the introduction of a group $R^0$ other than alkoxy or amino in method Cd) transition metal catalyzed carbon-carbon bond forming reactions may be used. Such reactions are known to the expert as Suzuki, Negishi, Kumada and Stille coupling reactions and are performed under typical reaction conditions using the appropriate catalyst.

In method E), preferred leaving groups Z are e.g. halogen, such as chloro or bromo, and also sulfonates, e.g. p-toluenesulfonate. Strong bases considered are metal hydroxides, such as sodium hydroxide, metal alkoxide, e.g. potassium t-butoxide, or metal amides, e.g. lithium diisopropylamide.

In method F), cyclization is performed with a halogenating agent, e.g. elemental halogen such as bromine, complexes of halogen with amines, such as pyridinium-tribromide, and copper halogenides such as copper(II) bromide or copper(II) chloride, in the presence of a base compatible with oxidation reagents, e.g. metal carbonates such as potassium carbonate, or metal hydroxide such as lithium hydroxide. In place of the halogenating it is also possible to use a sulfonyloxy introducing agent, e.g. a iodonium compound such as [hydroxy(tosyloxy)iodo]benzene.

Suitable leaving groups Z in method H) are e.g. halogen, such as chloro or bromo, sulfonates, e.g. p-toluenesulfonate, or another activated hydroxy group.

If one or more other functional groups, for example carboxy, hydroxy or amino, are or need to be protected in a compound of formulas (II) to (X), because they should not take part in the reaction, these are such protecting groups as are usually applied in the synthesis of amides, in particular peptide compounds, cephalosporins, penicillins, nucleic acid derivatives and sugars.

The protecting groups may already be present in precursors and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end products. The specialist knows, or can easily establish, which protecting groups are suitable with the reactions mentioned hereinabove and hereinafter.

The protection of such functional groups by such protecting groups, the protecting groups themselves, and their removal reactions are described for example in standard reference books for peptide synthesis and in special books on protective groups such as J. F. W. McOmie, "Protective Groups in Organic Chemistry", Plenum Press, London and New York 1973, in "Methoden der organischen Chemie" (Methods of organic chemistry), Houben-Weyl, 4th edition, Volume 15/I, Georg Thieme Verlag, Stuttgart 1974, and in T. W. Greene, "Protective Groups in Organic Synthesis", Wiley, New York.

In the additional process steps, carried out as desired, functional groups of the starting compounds which should not take part in the reaction may be present in unprotected form or may be protected for example by one or more of the protecting groups mentioned hereinabove under "protecting groups". The protecting groups are then wholly or partly removed according to one of the methods described there.

In the conversion of an obtainable compound of formula (I) or of formula (II) into another compound of formula (I) or of formula (II), an amino group may be alkylated or acylated to give the correspondingly substituted compounds. Alkylation may be performed with an alkyl halide or an activated alkyl ester. For methylation, diazomethane may be used. Alkylation may also be performed with an aldehyde under reducing conditions. For acylation the corresponding acyl chloride is preferred. Alternatively, an acid anhydride may be used, or acylation may be accomplished with the free acid under conditions used for amide formation known per se in peptide chemistry, e.g. with activating agents for the carboxy group, such as 1-hydroxybenzotriazole, optionally in the presence of suitable catalysts or co-reagents. Furthermore amine may be transformed into heteroaryl and heterocyclyl under reaction conditions typical for such cyclizations.

A hydroxy group, e.g. a hydroxy group $R^1$, a hydroxy group in the ring A or a hydroxy group as the substituent $R^6$, may be alkylated (etherified) or acylated (esterified) to give the correspondingly substituted compounds in a procedure related to the one described for an amino group. Alkylation may be performed with an alkyl halide or an activated alkyl ester. For methylation, diazomethane may be used. For acylation the corresponding acyl chloride or acid anhydride may be used, or acylation may be accomplished with the free acid and a suitable activating agent.

Reduction of a nitro group in a nitro-substituted aryl or heteroaryl group to give the corresponding amino group is done, e.g., with iron powder in alcohol or with other reducing agents.

A carboxy group in a carboxy-substituted aryl or heteroaryl group may be amidated under conditions used for amide formation known per se in peptide chemistry, e.g. with the corresponding amine and an activating agent for the carboxy group, such as 1-hydroxybenzotriazole, optionally in the presence of suitable catalysts or co-reagents.

A chloro, bromo or iodo substitutent in an aryl or heteroaryl group may be replaced by phenyl or a phenyl derivative by reaction with a suitable phenylboronic acid in a Suzuki reaction as described under method Cd).

In the conversion of a compound of formula (II) into another compound of formula (II) using the aforementioned reaction conditions, care must be taken not to submit the compounds to basic conditions, because otherwise the compound of formula (II) will cyclize to give a corresponding compound of formula (I) in a reaction corresponding to process A), D) or G).

Salts of a compound of formula (I) or of formula (II) with a salt-forming group may be prepared in a manner known per se. Acid addition salts of compounds of formula (I) or of formula (II) may thus be obtained by treatment with an acid or with a suitable anion exchange reagent.

Salts can usually be converted to free compounds, e.g. by treating with suitable basic agents, for example with alkali metal carbonates, alkali metal hydrogencarbonates, or alkali metal hydroxides, typically potassium carbonate or sodium hydroxide.

It should be emphasized that reactions analogous to the conversions mentioned in this chapter may also take place at the level of appropriate intermediates.

All process steps described here can be carried out under known reaction conditions, preferably under those specifically mentioned, in the absence of or usually in the presence of solvents or diluents, preferably such as are inert to the reagents used and able to dissolve these, in the absence or presence of catalysts, condensing agents or neutralising agents, for example ion exchangers, typically cation exchangers, for example in the H⁺ form, depending on the type of reaction and/or reactants at reduced, normal, or elevated temperature, for example in the range from −100° C. to about 190° C., preferably from about −80° C. to about 150° C., for example at −80 to +60° C., at −20 to +40° C., at room temperature, or at the boiling point of the solvent used, under atmospheric pressure or in a closed vessel, where appropriate under pressure, and/or in an inert atmosphere, for example under argon or nitrogen.

Salts may be present in all starting compounds and transients, if these contain salt-forming groups. Salts may also be present during the reaction of such compounds, provided the reaction is not thereby disturbed.

At all reaction stages, isomeric mixtures that occur can be separated into their individual isomers, e.g. diastereomers or enantiomers, or into any mixtures of isomers, e.g. racemates or diastereomeric mixtures.

The invention relates also to those forms of the process in which one starts from a compound obtainable at any stage as a transient and carries out the missing steps, or breaks off the process at any stage, or forms a starting material under the reaction conditions, or uses said starting material in the form of a reactive derivative or salt, or produces a compound obtainable by means of the process according to the invention and further processes the said compound in situ. In the preferred embodiment, one starts from those starting materials which lead to the compounds described hereinabove as preferred, particularly as especially preferred, primarily preferred, and/or preferred above all.

In the preferred embodiment, a compound of formula (I) or of formula (II) is prepared according to or in analogy to the processes and process steps defined in the Examples.

The compounds of formula (I) or of formula (II), including their salts, are also obtainable in the form of hydrates, or their crystals can include for example the solvent used for crystallization, i.e. be present as solvates.

New starting materials and/or intermediates, as well as processes for the preparation thereof, are likewise the subject of this invention. In the preferred embodiment, such starting materials are used and reaction conditions so selected as to enable the preferred compounds to be obtained.

Starting materials of formula (III) to (X) are known, commercially available, or can be synthesized in analogy to or according to methods that are known in the art.

For example, a compound of formula (III) is obtained in a cyclization reaction related to process A), but with a starting compound wherein the substituent R⁰ in formula (II) is OH, preferably in protected form, e.g. as a methyl or optionally substituted benzyl ether, or as an ester with an organic acid. A compound of formula (V) is also obtained in a cyclization reaction related to process A), but with a starting compound wherein the substituent R⁰ in formula (II) is a leaving group Z or a suitable precursor thereof.

A compound of formula (V) may also be obtained by reacting a carboxylic acid derivative of fomula (XI)

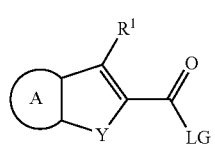

(XI)

wherein LG is a leaving group, e.g. lower alkoxy, acyloxy, N-alkoxyalkylamino or halogen, with a suitable metallated aryl or heteroaryl derivative of formula (XII)

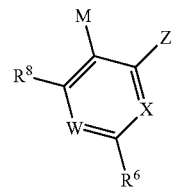

(XII)

wherein M is a metal, preferably lithium.

A compound of formula (VIII) is obtained by reacting the corresponding acetyl compound (Z=H) with a halogenating or a sulfonyloxy-introducing agent as described under method F). The same reagents are also useful to prepare a compound of formula (X) from the corresponding acetyl compound (Z=H).

PHARMACEUTICAL PREPARATIONS, METHODS, AND USES

The present invention relates also to pharmaceutical compositions that comprise a compound of formula (I) or formula (II) as active ingredient and that can be used especially in the treatment of the diseases mentioned at the beginning. Compositions for enteral administration, such as nasal, buccal, rectal or, especially, oral administration, and for parenteral administration, such as intravenous, intramuscular or subcutaneous administration, to warm-blooded animals, especially humans, are especially preferred. The compositions comprise the active ingredient alone or, preferably, together with a pharmaceutically acceptable carrier. The dosage of the active ingredient depends upon the disease to be treated and upon the species, its age, weight, and individual condition, the individual pharmacokinetic data, and the mode of administration.

The present invention relates especially to pharmaceutical compositions that comprise a compound of formula (I), a compound of formula (II), a tautomer, a prodrug or a pharmaceutically acceptable salt, or a hydrate or solvate thereof, and at least one pharmaceutically acceptable carrier.

The invention relates also to pharmaceutical compositions for use in a method for the prophylactic or especially therapeutic management of the human or animal body, in particular in a method of treating neoplastic disease, autoimmune disease, transplantation related pathology and/or degenerative disease, especially those mentioned hereinabove.

The invention relates also to processes and to the use of compounds of formula (I) or formula (II) thereof for the preparation of pharmaceutical preparations which comprise compounds of formula (I) or formula (II) as active component (active ingredient).

A pharmaceutical composition for the prophylactic or especially therapeutic management of a neoplastic disease, autoimmune disease, transplantation related pathology and/or degenerative disease, of a warm-blooded animal, especially a human or a commercially useful mammal requiring such treatment, comprising a novel compound of formula (I) or formula (II) as active ingredient in a quantity that is prophylactically or especially therapeutically active against the said diseases, is likewise preferred.

The pharmaceutical compositions comprise from approximately 1% to approximately 95% active ingredient, single-dose administration forms comprising in the preferred embodiment from approximately 20% to approximately 90% active ingredient and forms that are not of single-dose type comprising in the preferred embodiment from approximately 5% to approximately 20% active ingredient. Unit dose forms are, for example, coated and uncoated tablets, ampoules, vials, suppositories, or capsules. Further dosage forms are, for example, ointments, creams, pastes, foams, tinctures, lipsticks, drops, sprays, dispersions, etc. Examples are capsules containing from about 0.05 g to about 1.0 g active ingredient.

The pharmaceutical compositions of the present invention are prepared in a manner known per se, for example by means of conventional mixing, granulating, coating, dissolving or lyophilizing processes.

Preference is given to the use of solutions of the active ingredient, and also suspensions or dispersions, especially isotonic aqueous solutions, dispersions or suspensions which, for example in the case of lyophilized compositions comprising the active ingredient alone or together with a carrier, for example mannitol, can be made up before use. The pharmaceutical compositions may be sterilized and/or may comprise excipients, for example preservatives, stabilizers, wetting agents and/or emulsifiers, solubilizers, salts for regulating osmotic pressure and/or buffers and are prepared in a manner known per se, for example by means of conventional dissolving and lyophilizing processes. The said solutions or suspensions may comprise viscosity-increasing agents, typically sodium carboxymethylcellulose, carboxymethylcellulose, dextran, polyvinylpyrrolidone, or gelatins, or also solubilizers, e.g. Tween 80® (polyoxyethylene(20)sorbitan mono-oleate).

Suspensions in oil comprise as the oil component the vegetable, synthetic, or semi-synthetic oils customary for injection purposes. In respect of such, special mention may be made of liquid fatty acid esters that contain as the acid component a long-chained fatty acid having from 8 to 22, especially from 12 to 22, carbon atoms. The alcohol component of these fatty acid esters has a maximum of 6 carbon atoms and is a monovalent or polyvalent, for example a mono-, di- or trivalent, alcohol, especially glycol and glycerol. As mixtures of fatty acid esters, vegetable oils such as cottonseed oil, almond oil, olive oil, castor oil, sesame oil, soybean oil and groundnut oil are especially useful.

The manufacture of injectable preparations is usually carried out under sterile conditions, as is the filling, for example, into ampoules or vials, and the sealing of the containers.

Suitable carriers are especially fillers, such as sugars, for example lactose, saccharose, mannitol or sorbitol, cellulose preparations, and/or calcium phosphates, for example tricalcium phosphate or calcium hydrogen phosphate, and also binders, such as starches, for example corn, wheat, rice or potato starch, methylcellulose, hydroxypropyl methylcellulose, sodium carboxymethylcellulose, and/or polyvinylpyrrolidone, and/or, if desired, disintegrators, such as the above-mentioned starches, also carboxymethyl starch, crosslinked polyvinylpyrrolidone, alginic acid or a salt thereof, such as sodium alginate. Additional excipients are especially flow conditioners and lubricants, for example silicic acid, talc, stearic acid or salts thereof, such as magnesium or calcium stearate, and/or polyethylene glycol, or derivatives thereof.

Tablet cores can be provided with suitable, optionally enteric, coatings through the use of, inter alia, concentrated sugar solutions which may comprise gum arabic, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropylmethylcellulose phthalate. Dyes or pigments may be added to the tablets or tablet coatings, for example for identification purposes or to indicate different doses of active ingredient.

Pharmaceutical compositions for oral administration also include hard capsules consisting of gelatin, and also soft, sealed capsules consisting of gelatin and a plasticizer, such as glycerol or sorbitol. The hard capsules may contain the active ingredient in the form of granules, for example in admixture with fillers, such as corn starch, binders, and/or glidants, such as talc or magnesium stearate, and optionally stabilizers. In soft capsules, the active ingredient is preferably dissolved or suspended in suitable liquid excipients, such as fatty oils, paraffin oil or liquid polyethylene glycols or fatty acid esters of ethylene or propylene glycol, to which stabilizers and detergents, for example of the polyoxyethylene sorbitan fatty acid ester type, may also be added.

Pharmaceutical compositions suitable for rectal administration are, for example, suppositories that consist of a combination of the active ingredient and a suppository base. Suitable suppository bases are, for example, natural or synthetic triglycerides, paraffin hydrocarbons, polyethylene glycols or higher alkanols.

For parenteral administration, aqueous solutions of an active ingredient in water-soluble form, for example of a water-soluble salt, or aqueous injection suspensions that contain viscosity-increasing substances, for example sodium carboxymethylcellulose, sorbitol and/or dextran, and, if desired, stabilizers, are especially suitable. The active ingredient, optionally together with excipients, can also be in the form of a lyophilizate and can be made into a solution before parenteral administration by the addition of suitable solvents.

Solutions such as are used, for example, for parenteral administration can also be employed as infusion solutions.

Preferred preservatives are, for example, antioxidants, such as ascorbic acid, or microbicides, such as sorbic acid or benzoic acid.

The present invention relates furthermore to a method for the treatment of a neoplastic disease, autoimmune disease, transplantation related pathology and/or degenerative disease, which comprises administering a compound of formula (I), a compound of formula (II), or a pharmaceutically acceptable salt thereof, wherein the radicals and symbols have the meanings as defined above for formula (I) or formula (II), in a quantity effective against said disease, to a warm-blooded animal requiring such treatment. The compounds of formula (I) or formula (II) can be administered as such or especially in the form of pharmaceutical compositions, prophylactically or therapeutically, preferably in an amount effective against the said diseases, to a warm-blooded animal, for example a human, requiring such treatment. In the case of an individual having a bodyweight of about 70 kg the daily dose administered is from approximately 0.05 g to approximately 5 g, preferably from approximately 0.25 g to approximately 1.5 g, of a compound of the present invention.

The present invention relates especially also to the use of a compound of formula (I), a compound of or formula (II), or a pharmaceutically acceptable salt thereof, especially a compound of formula (I) or formula (II) which is said to be preferred, or a pharmaceutically acceptable salt thereof, as such or in the form of a pharmaceutical formulation with at least one pharmaceutically acceptable carrier for the therapeutic and also prophylactic management of one or more of the diseases mentioned hereinabove, in particular a neoplastic disease, autoimmune disease, transplantation related pathology and/or degenerative disease.

The preferred dose quantity, composition, and preparation of pharmaceutical formulations (medicines) which are to be used in each case are described above.

The following Examples serve to illustrate the invention without limiting the invention in its scope.

EXAMPLES

Abbreviations: DMF=dimethyl formamide; DMSO=dimethyl sulfoxide; eq.=equivalent(s); m.p. melting point; MS=mass spectrum; r.t.=room temperature; RT=retention time in minutes; THF=tetrahydrofuran.

Example 1

3-Amino-5-chloro-2-(2-benzyloxybenzoyl)-benzofuran

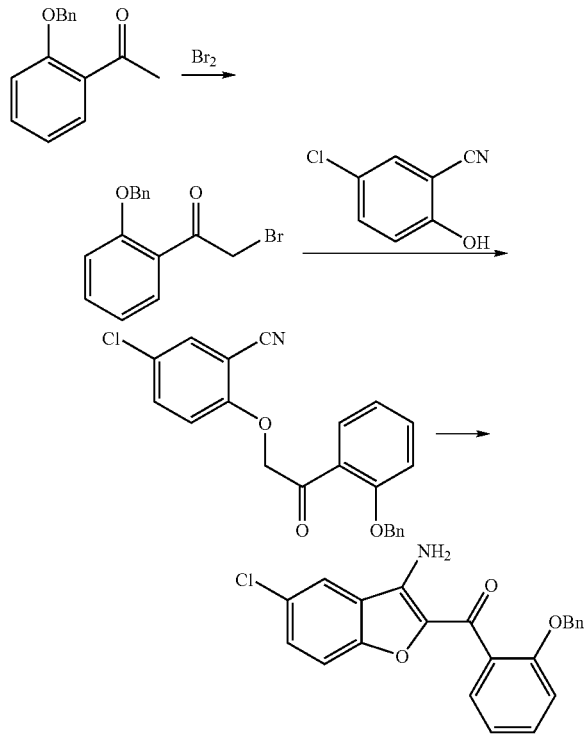

A solution of sodium methanolate (0.07 g, 1.3 mmol) in methanol is added to a solution of ω-(2-cyano-4-chlorophenoxy)-2-benzyloxy-acetophenone (0.5 g, 1.32 mmol) in methanol (30 ml) at 0° C. After 2 h at r.t. the reaction mixture is concentrated under reduced pressure. The residue is diluted with ethyl acetate and washed with water. Drying over sodium sulfate, filtering, evaporating the solvent and purification of the residue by silicagel column chromatography yields the title compound, having a m.p. of 158-160° C.

Example 1a

ω-(2-Cyano-4-chlorophenoxy)-2-benzyloxy-acetophenone

A suspension of potassium carbonate (0.06 g, 4.0 mmol), 4-chloro-2-cyanophenol (0.25 g, 1.6 mmol) and ω-bromo-2-benzyloxy-acetophenone (0.49 g, 1.6 mmol) in dry DMF (10 ml) is stirred at room temperature for 20 h. After evaporating the solvent under reduced pressure the residue is taken up in ethyl acetate. The solution is washed with water, dried over sodium sulfate and evaporated under reduced pressure. The residue is purified by silical gel column chromatography to yield the title compound.

Example 1b

ω-Bromo-2-benzyloxy-acetophenone

Bromine (1.4 g, 8.8 mmol) is added dropwise with stirring to a solution of 2-benzyloxy-acetophenone (2.0 g, 8.8 mmol) in dry ether (30 ml) at room temperature. After stirring for additional 2 h the solution is washed with water and dried over sodium sulfate. Evaporation of the filtered solution yields the title compound. $^1$H-NMR (CDCl$_3$, 400 MHz): 7.83-7.81 (m, 1H); 7.49-7.38 (m, 6H); 7.06-7.00 (m, 2H); 5.18 (s, 2H), 4.52 (s, 3H).

Example 2

3-Amino-5-chloro-2-(2-ethoxybenzoyl)-benzofuran

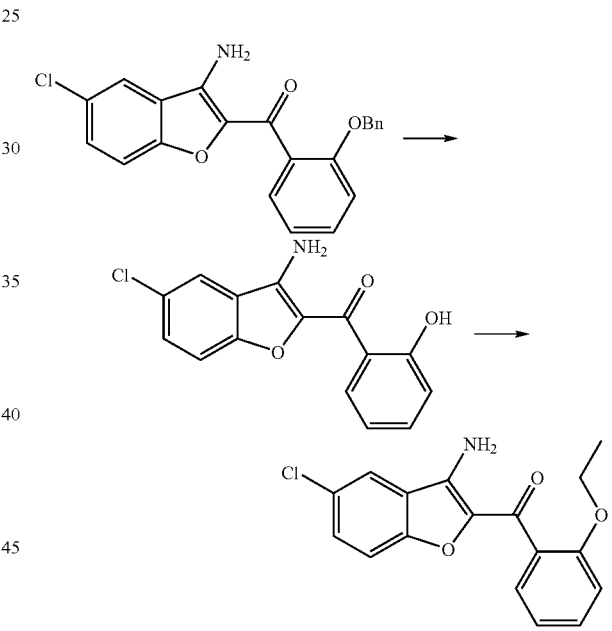

A suspension of potassium carbonate (0.056 g, 0.4 mmol), 3-amino-5-chloro-2-(2-hydroxybenzoyl)-benzofuran (0.05 g, 0.4 mmol) and ethyl iodide (0.05 g, 0.34 mmol) in dry DMF is stirred at 60° C. for 2 h. The resulting mixture is diluted with ethyl acetate and washed with water. Drying over sodium sulfate, filtering, evaporating the solvent and purification of the residue by silicagel column chromatography yields the title compound, having a m.p. of 114-115° C.

Example 2a

3-Amino-5-chloro-2-(2-hydroxybenzoyl)-benzofuran

3-Amino-5-chloro-2-(2-benzyloxybenzoyl)-benzofuran (Example 1, 0.5 g, 1.3 mmol) in ethyl acetate (15 ml) is stirred at room temperature under an atmosphere of hydrogen in the presence of palladium on charcoal (0.025 g). After 3 h the mixture is filtered over Celite® and evaporated to dryness.

Purification of the residue by chromatography yields the title compound, having a m.p. of 208-210° C.

Example 3

3-Amino-5-chloro-2-(2-ethoxy-5-nitrobezoyl)-benzofuran

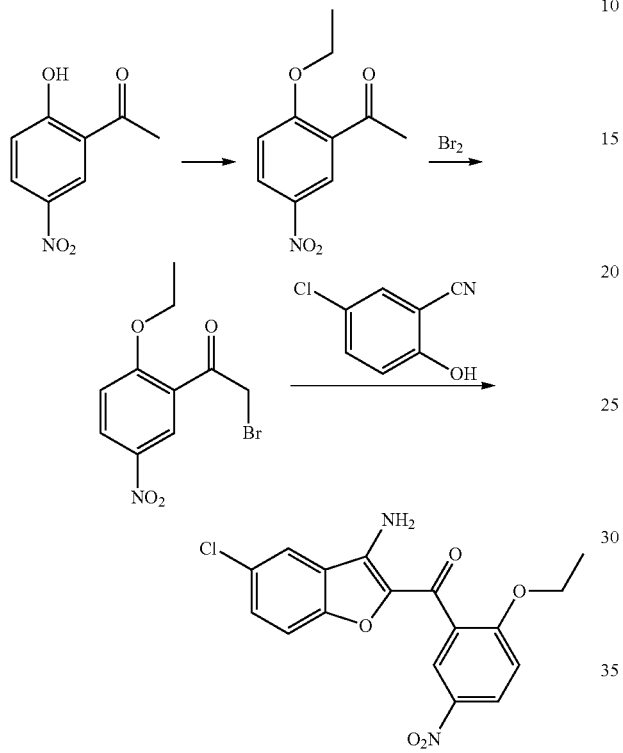

A suspension of potassium carbonate (0.27 g, 1.95 mmol), 4-chloro-2-cyanophenol (0.12 g, 0.78 mmol) and ω-bromo-2-ethoxy-5-nitroacetophenone (0.24 g, 8.5 mmol) in dry DMF (5 ml) is stirred at 80° C. for 5 h. After evaporating the solvent under reduced pressure the residue is taken up in ethyl acetate. The solution is washed with water, dried over sodium sulfate and evaporated under reduced pressure. The residue is purified by silicagel column chromatography to yield the title compound of m.p. 175-176° C.

Example 3a

ω-Bromo-2-ethoxy-5-nitroacetophenone

Bromine (1.4 g, 8.8 mmol) is added dropwise with stirring to a solution of 2-ethoxy-5-nitroacetophenone (2.0 g, 8.8 mmol) in dry ether (30 ml) at room temperature. After stirring for 2 additional hours the solution is washed with water and dried over sodium sulfate. Evaporation of the filtered solution yields the title compound in pure state. 1H-NMR (CDCl$_3$, 400 MHz): 8.68 (d, 1H); 8.35 (dd, 1H); 7.04 (d, 1H); 4.53 (s, 2H); 4.27 (q, 2H); 2.65 (s, 3H); 1.55 (t, 3H).

Example 3b

2-Ethoxy-5-nitroacetophenone

A suspension of potassium carbonate (1.12 g, 8.0 mmol), 2-hydroxy-5-nitroacetophenone (1.0 g, 5.5 mmol) and ethyl iodide (1.28 g, 8.25 mmol) in dry DMF (10 ml) is stirred at room temperature for 24 h. The resulting mixture is diluted with ethyl acetate and washed with water. Drying over sodium sulfate, filtering, evaporating the solvent and purification of the residue by silicagel column chromatography yields the title compound. $^1$H-NMR (CDCl$_3$, 400 MHz): 8.62 (d, 1H); 8.32 (dd, 1H); 7.02 (d, 1H); 4.25 (q, 2H); 2.65 (s, 3H); 1.55 (t, 3H).

Example 4

3-Amino-5-chloro-2-(2-allyloxy-5-methoxybenzoyl)-benzofuran

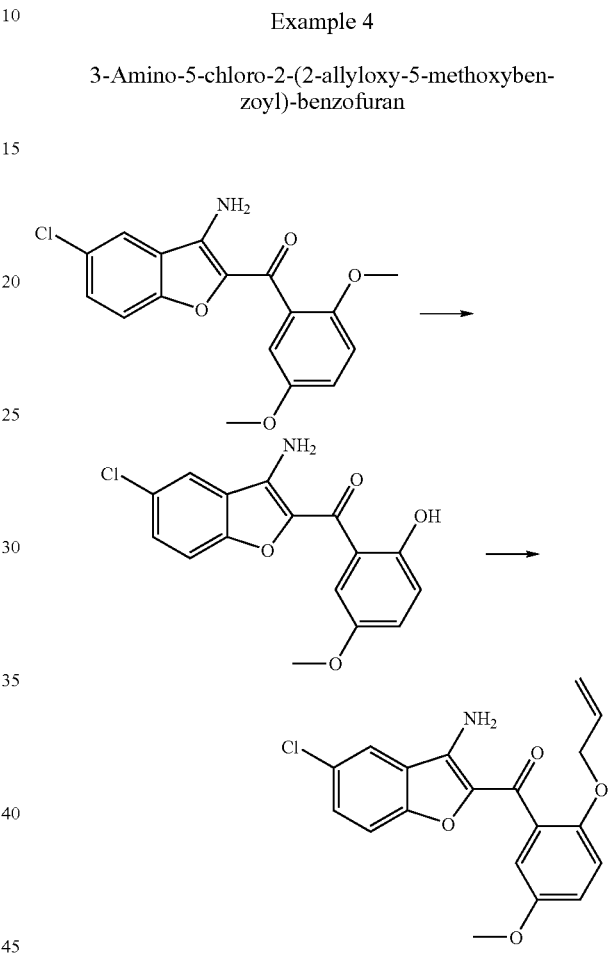

A suspension of 3-amino-5-chloro-2-(2-hydroxy-5-methoxybenzoyl)-benzofuran (0.06 g, 0.19 mmol), potassium carbonate (0.08 g, 0.6 mmol) and allyl bromide (0.1 g, 0.8 mmol) in dry acetone (3 ml) is stirred 55° C. for 48 h. The solids are filtered off and the solution is concentrated under reduced pressure. Purification of the residue by silicagel column chromatography yields the title compound of m.p. 115-116° C.

Example 4a

3-Amino-5-chloro-2-(2-hydroxy-5-methoxybenzoyl)-benzofuran

A solution of 3-amino-5-chloro-2-(2,5-dimethoxybenzoyl)-benzofuran (0.83 g, 2.5 mmol), sodium thiomethoxide (0.44 g, 6.25 mmol) and lithium bromide (0.22 g, 2.5 mmol) in anhydrous DMF (30 ml) is heated at 80° C. for 72 h. The solvent is removed under high vacuum and the residue is dissolved in a mixture of aqueous ammonium chloride and ethyl acetate. The organic phase is washed with brine, dried and evaporated under reduced pressure. Purification of the product on silicagel yields the title compound of m.p. 202-205° C. ¹H-NMR (d⁶-DMSO, 300 MHz): 11.81 (s, 1H); 8.21-8.20 (m, 1H); 7.82-7.80 (m, 1H); 7.66-7.63 (m, 3H); 7.11 (dd, 1H); 6.87 (d, 2H); 3.79 (s, 3H).

Example 5

3-Amino-7-methyl-2-(2-ethoxybenzoyl)-benzofuran

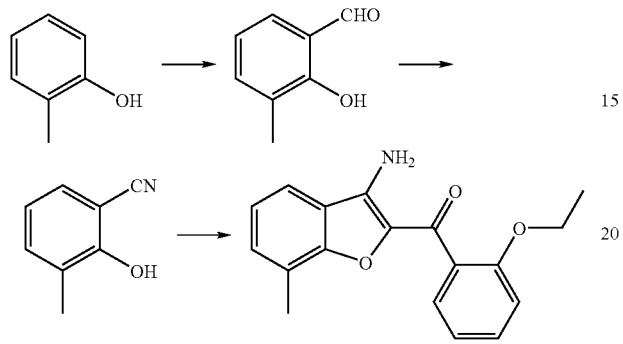

A suspension of potassium carbonate (1.24 g, 8.9 mmol), 2-hydroxy-3-methylbenzonitrile (0.3 g, 2.25 mmol) and ω-bromo-2-ethoxyacetophenone (0.55 g, 2.25 mmol) in dry DMF (10 ml) is stirred at 60° C. for 20 h. The reaction mixture is diluted with ethyl acetate and the resulting solution is washed repeatedly with brine. Drying of the solution over sodium sulfate, filtering and evaporation of the solvent leaves the crude product. Purification on silicagel yields the title compound in pure form. (CDCl₃, 400 MHz): 7.53 (d, 2H); 7.41 (m, 2H); 7.14-6.99 (m, 3H); 5.79 (bs, 2H); 4.09 (q, 2H); 2.36 (s, 3H); 1.17 (t, 3H).

Examples 5a

2-Hydroxy-3-methyl-benzonitrile

A solution of 2-hydroxy-3-methyl-benzaldehyde (1.13 g, 8.29 mmol), hydroxylamine hydrochloride (0.69 g, 9.9 mmol) and sodium acetate (0.8 g, 9.9 mmol) in formic acid (20 ml) is heated at reflux over night. The solvent is evaporated under reduced pressure and the residue is partitioned between water and ethyl acetate. The organic phase is dried and evaporated to dryness. Chromatography yields the title compound. (CDCl₃, 400 MHz): 7.32 (m, 2H); 6.89 (t, 1H); 5.65 (s, 1H); 2.23 (s, 3H).

Example 5b

2-Hydroxy-3-methyl-benzaldehyde

To a stirred solution of o-cresol (4.0 g, 37 mmol) in triethylamine (3.8 ml, 26.6 mmol) and toluene (100 ml) is added dropwise SnCl₄ (0.95 g, 36.5 mmol) under an atmosphere of nitrogen. After the addition of paraformaldehyde the mixture is heated at reflux for 18 h. The reaction mixture is quenched by pouring onto crushed ice and the pH is adjusted to 2 by addition of aqueous HCl. The product is extracted with ether and the resulting organic phase is washed with brine and dried over sodium sulfate. Evaporation of the solvent and purification by chromatography yields the title compound. (CDCl₃, 400 MHz): 11.26 (s, 1H); 9.86 (s, 1H); 7.37 (m, 2H); 6.91 (t, 1H); 2.23 (s, 3H).

The following compounds were prepared according to the method of Example 2, 3 and 4, respectively, or by modification of a substitutent:

TABLE 1

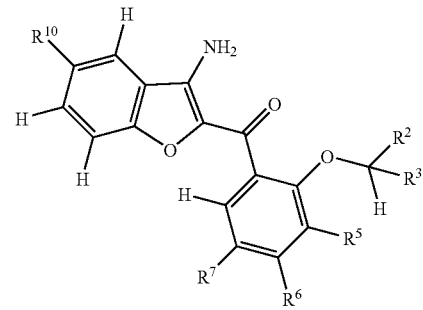

| Ex. | R² | R³ | R⁵ | R⁶ | R⁷ | R¹⁰ | m.p. | From Ex. |
|---|---|---|---|---|---|---|---|---|
| 6 | CH₃OCH₂— | H | H | H | H | Cl | 118-120° C. | |
| 7 | CH₃— | H | H | H | NH₂ | Cl | 144-146° C. | 3 |
| 8 | CH≡C— | H | H | H | H | Cl | 158° C. | |
| 9 | CH₃— | CH₃ | H | H | H | Cl | 110° C. | |
| 10 | ![morpholine-ethyl] | H | H | H | H | Cl | 130° C. | |
| 11 | (CH₃)₂NCH₂— | H | H | H | H | Cl | 131° C. | |
| 12 | CH₃— | H | H | H | OCH₃ | Cl | 124-125° C. | |
| 13 | CH≡C— | H | H | H | OCH₃ | Cl | 162-163° C. | |
| 14 | CH₃CH₂— | H | H | H | OCH₃ | Cl | 95-97° C. | |
| 15 | CH₃— | CH₃ | H | H | OCH₃ | Cl | 131-132° C. | |
| 16 | CH₃— | CH₃ | H | H | CH₃ | Cl | 110-112° C. | |

TABLE 1-continued

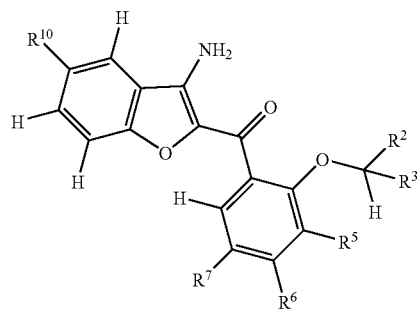

| Ex. | R² | R³ | R⁵ | R⁶ | R⁷ | R¹⁰ | m.p. | From Ex. |
|---|---|---|---|---|---|---|---|---|
| 17 | CH₃— | H | H | H | Cl | Cl | 140-142° C. | |
| 18 | CH₃— | H | H | H | F | Cl | 132-134° C. | |
| 19 | CH₃— | H | H | H | OCH₂CH₃ | Cl | oil | |
| 20 | CH₃— | H | H | H | COOCH₃ | Cl | 136-138° C. | |
| 21 | CH₃— | H | H | H | NHCOCH₃ | Cl | 110-112° C. | 7 |
| 22 | CH₃— | H | H | H | (N-pyrrolyl) | Cl | 104-106° C. | 7 |
| 23 | CH₃— | H | H | OMe | Br | Cl | 132-133° C. | |
| 24 | CH₃— | H | OMe | H | H | Cl | 121-124° C. | |
| 25 | CH₃— | H | Me | H | H | Cl | 54° C. | |
| 26 | CH₃— | H | H | H | CN | Cl | | |

The following compounds were prepared according to Example 3:

TABLE 2

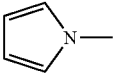

| Example | R² | R⁷ | m.p. |
|---|---|---|---|
| 27 | CH₃— | Cl | 174-176° C. |
| 28 | CH₃— | H | 156-158° C. |
| 29 | CH₃— | F | 152-156° C. |

TABLE 3

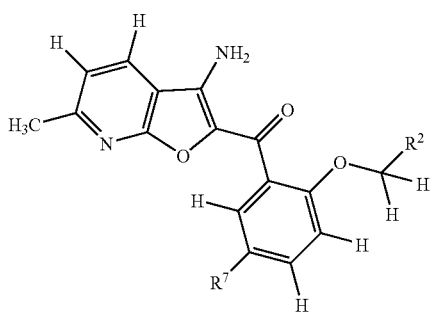

TABLE 3-continued

| Example | R² | R⁷ | m.p. |
|---|---|---|---|
| 30 | CH₃— | H | 168° C. |
| 31 | CH₃— | F | 162° C. |

Example 32

5-Chloro-2-(2-ethoxybenzoyl)-3-hydroxybenzofuran

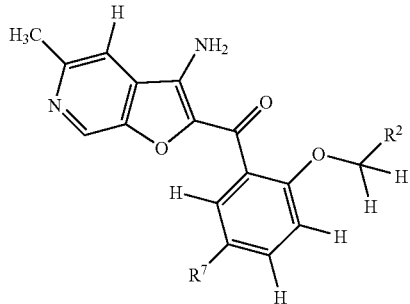

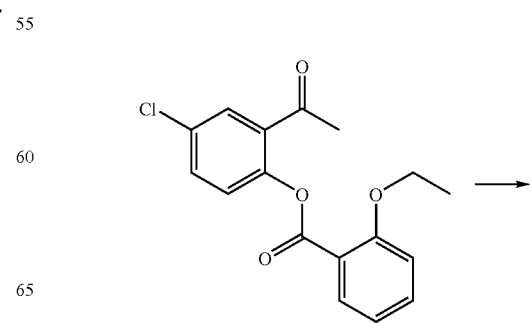

-continued

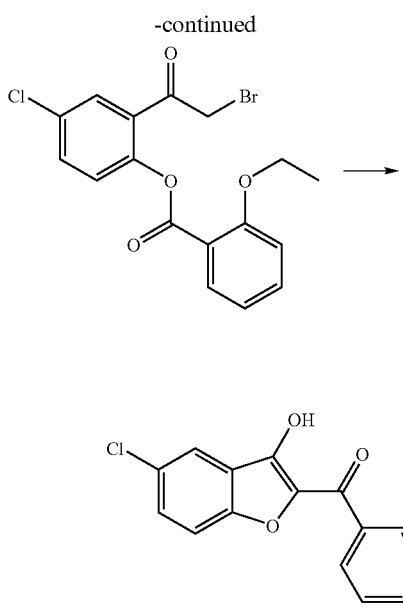

A suspension of 5-chloro-2-(2-ethoxybenzoyloxy)-ω-bromoacetophenone (1.4 g, 3.6 mmol) and potassium hydroxide (0.3 g, 5.46 mmol) is heated at reflux for 30 min. The reaction mixture is poured onto crushed ice and acidified using dilute sulfuric acid. The product is extracted with ethyl acetate and the resulting solution is dried over sodium sulfate. Concentration of the solution under reduced pressure and chromatography of the residue yields the title compound. $^1$H-NMR (CDCl$_3$, 400 MHz): 7.77 (s, 1H); 7.60 (m, 1H); 7.51-7.41 (m, 2H); 7.32 (d, 1H); 7.10-7.00 (m, 2H); 4.13 (q, 2H); 1.28 (t, 3H).

Example 32a

5-Chloro-2-(2-ethoxybenzoyloxy)-ω-bromoacetophenone

Bromine (0.6 g, 3.7 mmol) is added dropwise to a solution of 5-chloro-2-(2-ethoxybenzoyloxy)-acetophenone (1.19 g, 3.7 mmol) in dry diethyl ether (30 ml) at room temperature. The mixture is stirred for an additional hour. The reaction mixture is washed with brine and dried over sodium sulfate. The solvent is removed under reduced pressure to give the title compound in pure form.

Example 32b

5-Chloro-2-(2-ethoxybenzoyloxy)-acetophenone

To a solution of 5-chloro-2-hydroxyacetophenone (1.47 g, 8.66 mmol) in triethylamine (2.18 g, 21.66 mmol) and dry THF (30 ml) is added 2-ethoxybenzoyl chloride (1.6 g, 8.66 mmol). The mixture is heated at 55° C. overnight. The volatiles are removed at reduced pressure and the resulting residue is diluted with ethyl acetate and washed with brine. Drying of the resulting solution over sodium sulfate, evaporation of the solvent and chromatography on silicagel yields the title compound. $^1$H-NMR (CDCl$_3$, 400 MHz): 8.03 (d, 1H); 7.79 (s, 1H); 7.53-7.49 (m, 2H); 7.18 (d, 1H); 7.03-7.00 (m, 2H); 4.13 (q, 2H); 2.62 (s, 3H); 1.44 (s, 3H).

Reference Example A 2-(2,5-dimethoxybenzoyl)-3-hydroxybenzofuran

A solution of sodium methoxide (0.04 g, 0.67 mmol) in methanol was added to a solution of methyl 2-(2,5-dimethoxybenzoylmethoxy)-benzoate (0.20 g, 0.60 mmol) in dry methanol (20 ml) at 0° C. The reaction mixture was stirred at room temperature for 5 h. The reaction mixture was concentrated under reduced pressure and water was added, then extracted with ethyl acetate (three timer 30 ml). The organic layer was wahed with water, dried over sodium sulfate and evaporated under reduced pressure. The residue was purified by silica gel column chromatography eluting with a gradient from 12% to 20% ethyl acetate in hexane to get the title product, m.p. 158° C. $^1$H-NMR (CDCl$_3$, 400 MHz): 3.81 (s 3H), 3.83 (s, 3H), 6.99 (d, 1H), 7.07 (dd, 1H), 7.19 (d, 1H), 7.28 (d, 1H) 7.37 (d, 1H), 7.50 (t, 1H), 7.80 (d 1H).

Methyl 2-(2,5-dimethoxybenzoylmethoxy)-benzoate

A suspension of potassium carbonate (0.56 g, 4.0 mmol), ω-bromo-2,5-dimethoxy-acetophenone (0.51 g, 1.97 mmol) and methyl salicylate (0.3 g, 1.97 mmol) is stirred at room temperature over night. The reaction mixture is concentrated under reduced pressure and the residue is diluted with ethyl acetate. The resulting solution is washed with brine, dried over sodium sulfate, the volatiles are evaporated under reduced pressure and the residue purified on silicagel to give the title compound.

The following Reference Examples were prepared according to Example 3 or Reference example A, respectively:

TABLE 4

[Structure: benzofuran with R10, R1, R7 substituents and methoxy-phenyl ketone]

| Reference example | R¹ | R⁷ | R¹⁰ | m.p. | Method Ex. |
|---|---|---|---|---|---|
| Ref B | NH₂ | H | Cl | 163-164° C. | 3 |
| Ref C | OH | OCH₃ | Cl | 160° C. | Ref. A |

The following compounds were prepared according to Example 32 or by acylation of the corresponding compound wherein $R^{14}$ is hydrogen:

TABLE 5

[Structure: benzofuran with R10, R7, OR14 substituents]

| Example | R⁷ | R¹⁰ | R¹⁴ | m.p. |
|---|---|---|---|---|
| 33 | F | Cl | H | oil |
| 34 | F | Cl | —COCH₃ | 110 |
| 35 | F | Cl | —CONMe₂ | 118-120 |
| 36 | H | NH₂ | H | oil |

Example 37

3-Amino-5-chloro-2-(2-morpholino-3-pyridylcarbonyl)-benzofuran

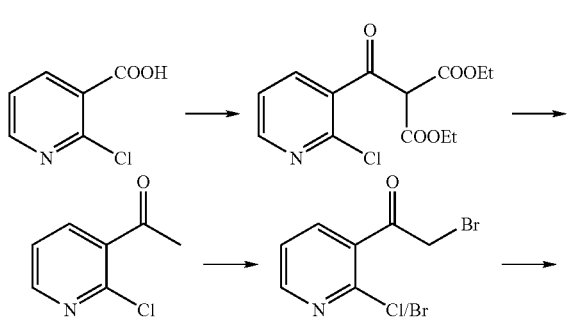

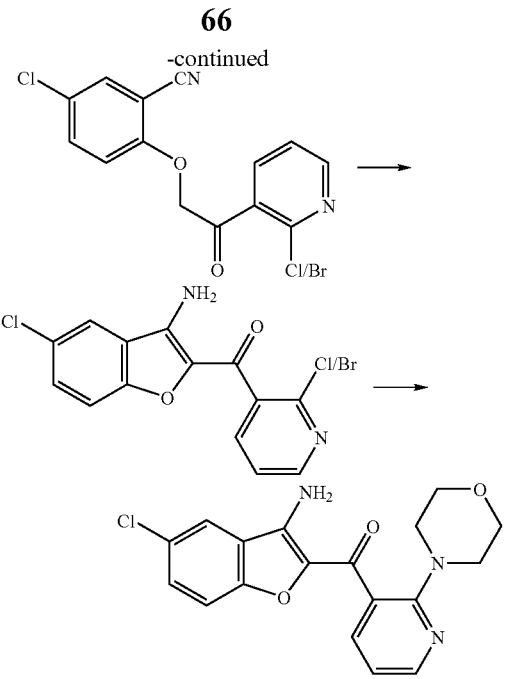

A mixture of 3-amino-5-chloro-2-(2-bromo/chloro-3-pyridylcarbonyl)-benzofuran (100 mg, 0.3 mmol) and morpholine (100 mg, 1.12 mmol) in THF is refluxed for 48 hours. The solvent is removed under reduced pressure and the residue is filtered over a pad of silicagel to give the title compound in pure form, m.p. 95-97° C.

Example 37a

3-Amino-5-chloro-2-(2-bromo/chloro-3-pyridylcarbonyl)-benzofuran

A mixture of 2-bromo/chloro-3-(bromoacetyl)-pyridine (1.64 g, 6.39 mmol), 5-chloro-2-hydroxybenzonitrile (1.03 g, 6.71 mmol) and potassium carbonate (1.33 g, 9.54 mmol) in acetone (70 ml) is stirred at room temperature for 24 hours. The salts are filtered and the filtrate evaporated under reduced pressure to give the crude title compound. Chromatography on silicagel gives the pure product in form of yellow crystals. ¹H-NMR (CDCl₃, 300 MHz): 8.53 (dd, 0.5H); 8.50 (dd, 0.5H); 7.88 (dd, 0.5H); 7.79 (dd, 0.5H); 7.62 (d, 0.5H); 7.48-7.36 (m, 1.5H); 7.28 (d, 1H); 5.94 (s, br, 2H).

Example 37b

2-Bromo/chloro-3-(bromoacetyl)-pyridine

Bromine (0.89 ml, 17.35 mmol) in acetic acid (10 ml) is added dropwise to 3-acetyl-2-chloro-pyridine (2.7 g, 17.35 mmol) in acetic acid (20 ml). After the addition of sulfuric acid (0.7 ml) the mixture is heated at 75° C. for 2 hours. The acetic acid is evaporated under reduced pressure. The residue is diluted with water and the pH adjusted by addition of 1M aqueous sodium hydroxide to pH 7. The product is extracted using chloroform, then purified by flash chromatography to give the title compound as a crystalline 1:1 mixture of 2-bromo-3-(bromoacetyl)-pyridine and 2-chloro-3-(bromoacetyl)-pyridine; ¹H-NMR (CDCl₃, 300 MHz): 8.55 (dd, 0.5H); 8.50 (dd, 0.5H); 7.94 (dd, 0.5H); 7.79 (dd, 0.5H); 7.43-7.37 (m, 1H); 4.56 (s, 1H); 4.53 (s, 1H).

Example 37c

3-Acetyl-2-chloropyridine

A mixture of 2-chloronicotinic acid (2-chloro-3-pyridyl-carboxylic acid, 4.0 g, 25.4 mmol), oxalyl chloride (2.28 ml, 26.65 mmol) and two drops of DMF are stirred in chloroform (60 ml) for 30 minutes and subsequently refluxed for 45 minutes. The volatiles are distilled under reduced pressure to give crude 2-chloronicotinoyl chloride. This crude product is added to a mixture of diethyl malonate (3.85 ml, 25.38 mmol), magnesium chloride (2.4 g, 25.38 mmol) and triethylamine (7 ml, 50.77 mmol) in acetonitrile (25 ml) with cooling, such that the temperature does not rise above 15° C. After stirring for 24 hours the reaction mixture is diluted with ether and washed repeatedly with 1 M hydrochloric acid and brine. Drying of the organic phase over magnesium sulfate, filtering and evaporation of the solvents gives crude diethyl 2-(2-chloronicotinoyl)-malonate. This crude product is dissolved in DMSO (40 ml) and water (3 ml), and is heated at 140-150° C. for four hours. The mixture is poured onto crushed ice and the product is extracted using ether. Filtering of the ether phase over a pad of silicagel gives 3-acetyl-2-chloropyridine as a yellow oil; $^1$H-NMR (CDCl$_3$, 300 MHz): 8.50 (dd, 1H); 7.91 (dd, 1H); 7.34 (ddd, 1H); 2.71 (s, 3H).

Example 38

2-(5-Fluoro-2-morpholinobenzoyl)-5-methoxybenzofuran

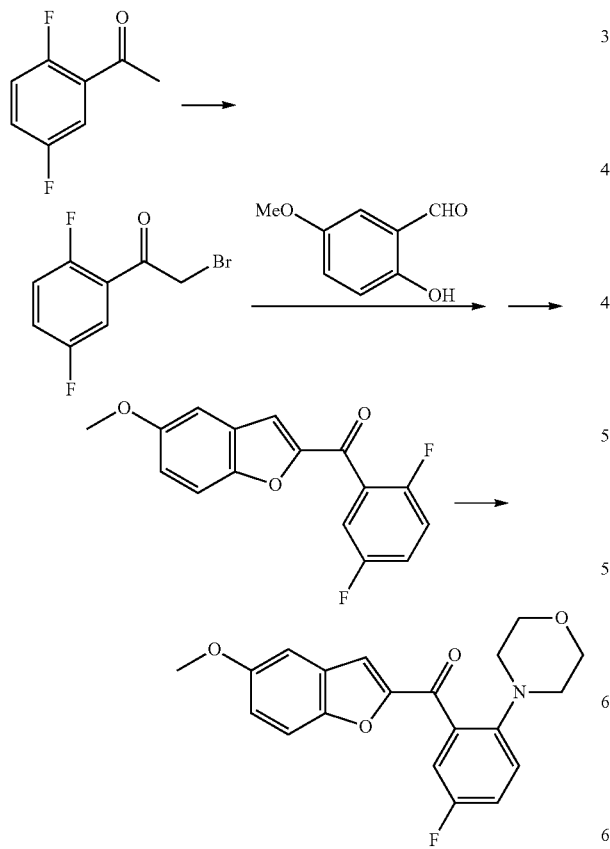

A mixture of 2-(2,5-difluorobenzoyl)-5-methoxybenzofuran (100 mg, 0.28 mmol) and morpholine (100 mg, 1.12 mmol) in toluene (10 ml) is heated at reflux for 24 hours. Evaporation and chromatography on silicagel gives the title compound, m.p. 85-88° C.

Example 38a

2-(2,5-Difluorobenzoyl)-5-methoxybenzofuran

A mixture of 2-hydroxy-5-methoxybenzaldehyde (0.5 g, 3.3 mmol), ω-bromo-2,5-difluoroacetophenone (0.85 g, 3.6 mmol) and potassium carbonate (1.13 g, 8.2 mmol) in acetonitrile (10 ml) is stirred in the presence of tetrabutylammonium iodide for 20 hours. The solvent is removed under reduced pressure and the residue is partitioned between water and ethyl acetate. The organic phase is separated, dried and concentrated. The residue is purified on silicagel, m.p. 75-78° C.

Example 38b

ω-Bromo-2,5-difluoroacetophenone

Bromine (0.8 ml, 15.5 mmol) is added dropwise to a solution of 2,5-difluoroacetophenone in ether (20 ml) at 0° C. The mixture is stirred for 3 hours, washed with brine, dried over magnesium sulfate, filtered and concentrated under reduced pressure to give ω-bromo-2,5-difluoroacetophenone in the form of a yellow oil, $^1$H-NMR (CDCl$_3$, 400 MHz): 7.63 (m, 1H); 7.27 (m, 1H); 7.16 (m, 1H); 4.49 (s, 2H).

Example 39

5-Methoxy-2-(2-morpholino-3-pyridylcarbonyl)-benzofuran

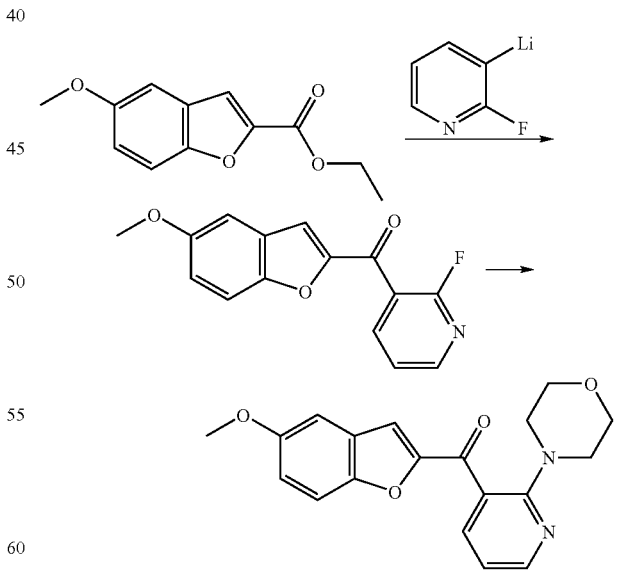

A mixture of 2-(2,5-difluorobenzoyl)-5-methoxybenzofuran (100 mg, 0.28 mmol) and morpholine (100 mg, 1.12 mmol) in toluene (10 ml) is heated at reflux for 24 hours. Evaporation and chromatography on silicagel gives the title compound, m.p. 85-88° C.

Example 39a

5-Methoxy-2-(2-fluoro-3-pyridylcarbonyl)-benzofuran

At 0° C. a solution of n-BuLi (0.73 ml, 1.17 mmol) is added to diisopropylamine (0.18 ml, 1.3 mmol). The mixture is stirred for 30 minutes at the same temperature before the resulting solution is added dropwise to a solution 2-fluoropyridine (0.1 ml, 1.17 mmol) in THF (3 ml) at −78° C. After stirring for one hour ethyl 5-methoxy-benzofuran-2-carboxylate (0.25 g, 1.17 mmol) in THF (4 ml) is added and stirring is continued for 2 hours at the same temperature. The reaction mixture is allowed to reach room temperature before quenching with saturated aqueous ammonium chloride solution. The product is extracted with ethyl acetate. Chromatography on silicagel gives the title compound, m.p. 130-134° C.

Example 40

5-Chloro-2-(2-morpholinobenzoyl)-benzofuran

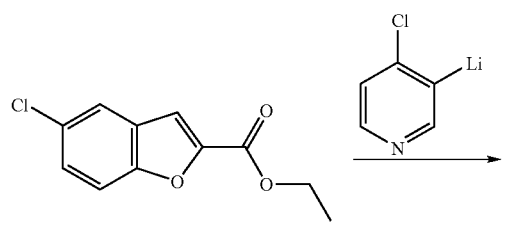

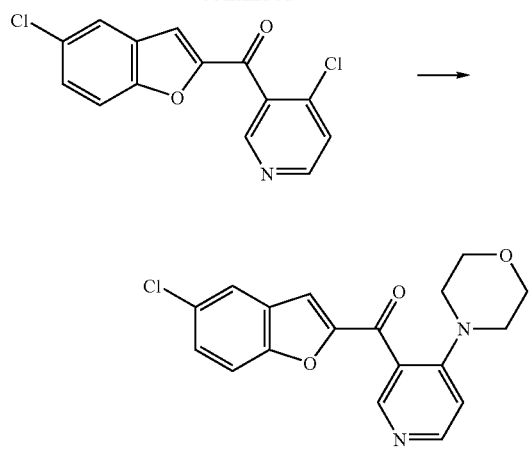

A solution of ethyl 5-chlorobenzofuran-2-carboxylate (350 mg, 1.56 mmol) in THF (10 ml) is added at −70° C. to a THF solution of lithiated 4-chloropyridine (1.8 mmol prepared according to G. Quéguiner et al., Synthesis 1986, 886-891). The mixture is allowed to reach room temperature within 16 hours before quenching with acetic acid. The product is extracted with chloroform. Drying and chromatography on silicagel gives the title compound.

The following compounds were prepared according to Example 37:

TABLE 6

| Ex. | $R^{10}$ | $R^1$ | $R^0$ | X | W | Salt | m.p. |
|---|---|---|---|---|---|---|---|
| 41 | Cl | $NH_2$ | OEt | CH | $COCONMe_2$ | | oil |
| 42 | Cl | $NH_2$ | O—iBu | CH | COMe | | 113-115° C. |
| 43 | I | $NH_2$ | OEt | CH | CH | | oil |
| 44 | Cl | $NH_2$ | OEt | CH | CCOOH | | 247-250° C. |
| 45 | F | $NH_2$ | OEt | CH | CH | | 127° C. |
| 46 | Cl | $NH_2$ | OEt | CH | $CSO_2NMe_2$ | | oil |
| 47 | OMe | $NH_2$ | OEt | CH | CH | | oil |
| 48 | OMe | $NH_2$ | OEt | CH | CF | | oil |
| 49 | OMe | NHCOOMe | OEt | CH | CF | | 143° C. |
| 50 | OMe | $NHSO_2NMe_2$ | OEt | CH | CF | | 130° C. |
| 51 | NHBoc | $NH_2$ | OEt | CH | CH | | oil |
| 52 | $NH_2$ | $NH_2$ | OEt | CH | CH | | oil |
| 53 | OMe | H | OEt | CH | CH | | 60° C. |
| 54 | OMe | $NHSO_2Me$ | OEt | CH | CF | | 125° C. |
| 55 | H | $NH_2$ | OEt | CH | CH | | oil |
| 56 | H | $NH_2$ | OEt | CH | CF | | oil |
| 57 | $CH_2OMe$ | H | OEt | CH | CF | | oil |
| 58 | OMe | $NHCOCH_2OMe$ | OEt | CH | CF | | oil |
| 59 | $NO_2$ | $NH_2$ | OEt | CH | CH | | 191-193° C. |
| 60 | OMe | $NH_2$ | $OCH_2CF_3$ | CH | CH | | 44° C. |
| 61 | Cl | $NH_2$ | $OCH_2CF_3$ | CH | CH | | 52° C. |
| 62 | Me | $NH_2$ | OEt | CH | CF | | 47° C. |
| 63 | OBenzyl | H | OEt | CH | CF | | 90-92° C. |
| 64 | OH | H | OEt | CH | CF | | 148-150° C. |

TABLE 6-continued

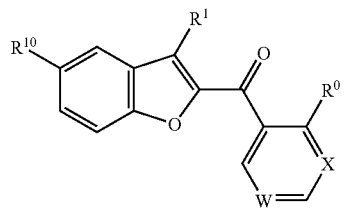

| Ex. | R10 | R1 | R0 | X | W | Salt | m.p. |
|---|---|---|---|---|---|---|---|
| 65 | OCOCH₃ | H | OEt | CH | CF | | solid |
| 66 | OEt | H | OEt | CH | CF | | solid |
| 67 | OAllyl | H | OEt | CH | CF | | 88° C. |
| 68 | O—iPr | H | OEt | CH | CF | | solid |
| 69 | OCH₂OMe | H | OEt | CH | CF | | 108° C. |
| 70 | OCH₂CH₂OMe | H | OEt | CH | CF | | solid |
| 71 | OCH₂CH₂NMe₂ | H | OEt | CH | CF | | solid |
| 72 | OCONMe₂ | H | OEt | CH | CF | | 86° C. |
| 73 | O-2-Pyridyl | H | OEt | CH | CF | | 92° C. |
| 74 | CH₂NEt₂ | H | OEt | CH | CF | | solid |
| 75 | OH | NH₂ | OEt | CH | CF | | 192° C. |
| 76 | Cl | NH₂ | NHEt | N | CH | | 188-189° C. |
| 77 | Cl | NH₂ | NMe₂ | N | CH | | oil |
| 78 | Cl | NH₂ | OEt | N | CH | | 186-187° C. |
| 79 | Cl | NH₂ | N-methylpyrrolidinyl | N | CH | | 194-195° C. |
| 80 | Cl | NH₂ | —N(Me)CH₂CH₂NMe | N | CH | | oil |
| 81 | Cl | NH₂ | —N(Me)CH₂CH₂Et | N | CH | | oil |
| 82 | Cl | NH₂ | N-methylpiperidinyl | N | CH | | 213-215° C. |
| 83 | Cl | NH₂ | 2,6-dimethyl-N-methylmorpholinyl | N | CH | | oil |
| 84 | Cl | NH₂ | N-methylhomopiperazinyl | N | CH | | oil |
| 85 | Cl | NH₂ | N,N'-dimethylpiperazinyl | N | CH | | 195-197° C. |
| 86 | Cl | NH₂ | 4-hydroxy-N-methylpiperidinyl | N | CH | | 204-205° C. |
| 87 | OMe | H | 3-methyl-N-methylpiperidinyl | N | CH | | solid |

TABLE 6-continued

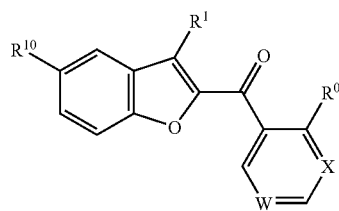

| Ex. | R¹⁰ | R¹ | R⁰ | X | W | Salt | m.p. |
|---|---|---|---|---|---|---|---|
| 88 | OMe | H | N-methyl-tetrahydropyridine | N | CH | | solid |
| 89 | OMe | H | N-methyl-2-methyl-tetrahydropyridine | N | CH | | solid |
| 90 | OMe | H | N-methylimidazole | N | CH | | solid |
| 91 | OMe | H | N-methylpiperidine | N | CH | | solid |
| 92 | OMe | H | N-methylpiperidine | N | CH | MeS | 77-78° C. |
| 93 | Cl | NH₂ | N-methylmorpholine | CH | CF | | oil |
| 94 | OMe | H | N,N'-dimethylpiperazine | CH | CF | | oil |
| 95 | OMe | H | N-methyl-tetrahydropyridine | CH | CF | | solid |
| 96 | OMe | H | N-methylpiperidine | CH | CF | MeS | solid |
| 97 | OMe | H | N-methyl-2-methylpiperidine | CH | CF | | solid |
| 98 | OMe | H | N-methyl-tetrahydropyridine | CH | CF | | solid |

TABLE 6-continued

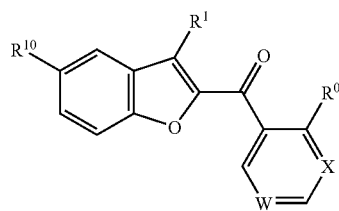

| Ex. | R¹⁰ | R¹ | R⁰ | X | W | Salt | m.p. |
|---|---|---|---|---|---|---|---|
| 99 | OMe | H | (1-methyl-3-methyl-tetrahydropyridinyl) | CH | CF | | solid |
| 100 | Cl | NH₂ | (1-methylpiperidinyl) | CH | CF | | 65-68° C. |
| 101 | Cl | NH₂ | (1-methylpiperidinyl) | CH | CF | MeS | 131-135° C. |
| 102 | Cl | NH₂ | (1,4-dimethylpiperazinyl) | CH | CF | | solid |
| 103 | Cl | NH₂ | (1-methyl-tetrahydropyridinyl) | CH | CF | | 52-55° C. |
| 104 | Cl | NH₂ | (1-methyl-3-methylpiperidinyl) | CH | CF | | 145-147° C. |
| 105 | OMe | H | (1-methylimidazolyl) | CH | CF | | 62° C. |
| 106 | OBenzyl | H | (4-methylmorpholinyl) | CH | CF | | 118-120° C. |
| 107 | OH | H | (4-methylmorpholinyl) | CH | CF | | solid |
| 108 | OEt | H | (4-methylmorpholinyl) | CH | CF | | solid |
| 109 | OBenzyl | H | (1-methyl-tetrahydropyridinyl) | CH | CF | | solid |
| 110 | OBenzyl | H | (1-methylpiperidinyl) | CH | CF | | solid |

TABLE 6-continued

[Structure: benzofuran with R10, R1, carbonyl linked to pyridine with R0, X, W]

| Ex. | R10 | R1 | R0 | X | W | Salt | m.p. |
|---|---|---|---|---|---|---|---|
| 111 | OEt | H | N-methyl-tetrahydropyridyl | CH | CF | | solid |
| 112 | OH | H | N-methyl-tetrahydropyridyl | CH | CF | | 62-65° C. |

Boc=tert-butoxycarbonyl, Mes=methanesulfonate

Example 113

3-Amino-2-(2'-ethoxy-5-fluorobenzoyl)-thieno[2,3-b]pyridine

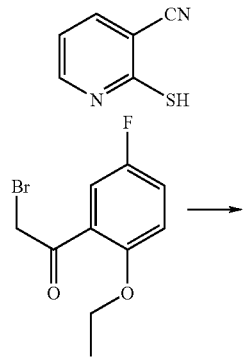

A suspension of potassium carbonate (0.189 g, 1.37 mmol), 2-ethoxy-5-fluorophenacyl bromide and 2-mercaptonicotine nitrile in dry DMF (8 ml) is stirred at room temperature for 16 h. The resulting mixture is diluted with ethyl acetate and washed with water. Drying over sodium sulfate, filtering, evaporating the solvent and purification of the residue by silicagel column chromatography yields the title compound, having a m.p. of 130° C.

The following compounds were prepared according to Example 113 or by reduction of the nitro group in position $R^{10}$:

TABLE 7

[Structure: thieno[2,3-b]pyridine with R10, NH2, carbonyl, ethoxyphenyl with R7]

| Example | $R^7$ | $R^{10}$ | m.p. |
|---|---|---|---|
| 114 | H | H | 138-142° C. |
| 115 | F | $NO_2$ | 205° C. |
| 116 | F | $NH_2$ | 80° C. |
| 117 | H | $NH_2$ | 116° C. |

Example 118

5,6-Dimethyl-3-amino-2-(2'-ethoxy-5'-fluorobenzoyl)-thieno[2,3-b]pyridine

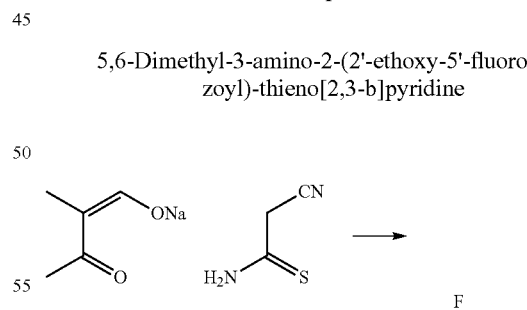

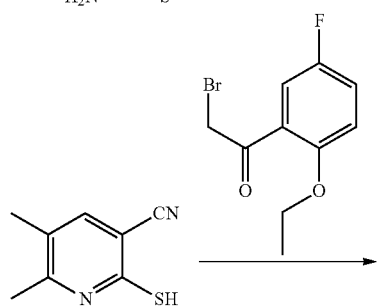

-continued

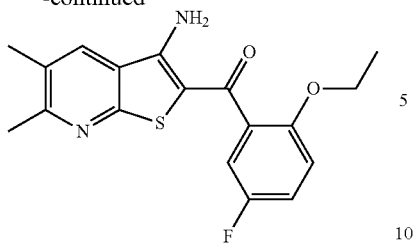

A suspension of potassium carbonate (0.189 g, 1.37 mmol), 2-ethoxy-5-fluorophenacyl bromide (1.02 g, 3.95 mmol) and 5,6-dimethyl-2-mercaptonicotine nitrile (0.50 g, 3.04 mmol) in dry DMF (10 ml) is stirred at room temperature for 16 h. The resulting mixture is diluted with ethyl acetate and washed with water. Drying over sodium sulfate, filtering, evaporating the solvent and purification of the residue by silicagel column chromatography yields the title compound, having a m.p. of 170° C.

Example 118a 5,6-Dimethyl-2-mercapto-nicotine nitrile

A mixture of cyanothioacetamide (2.0 g, 20 mmol), the sodium salt of ethyl-3-oxo-butenol (2.44 g, 20 mmol) and piperidine acetate (1.9 ml) in water (20 ml) is heated at reflux before adding acetic acid (3 ml). The resulting precipitate is filtered and washed with water. The crude product is dissolved by heating in methanol. Filtering and evaporation of the solvent under reduced pressure yields 5,6-dimethyl-2-mercapto-nicotine nitrile.

$^1$H-NMR (400 MHz, DMSO-$d_6$): 14.02 (s, 1H), 7.95 (s, 1H), 2.37 (s, 3H), 2.05 (s, 3H).

Example 119

5,6-Dimethyl-3-amino-2-(2'-N-morpholino-5'-fluorobenzoyl)-thieno[2,3-b]pyridin

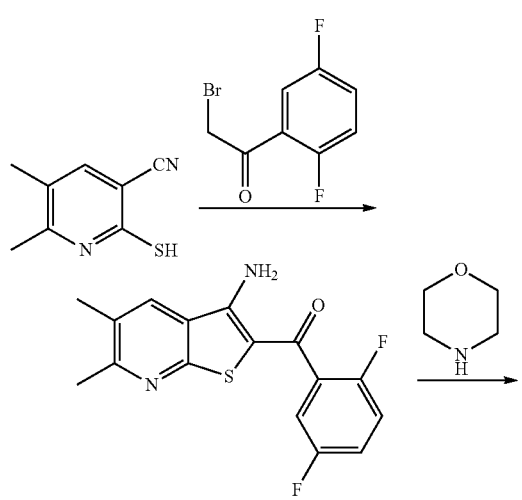

-continued

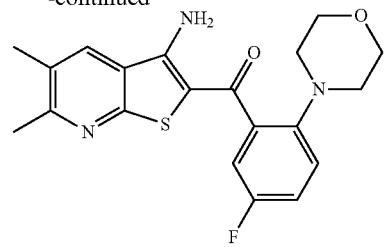

A mixture of 5,6-dimethyl-3-amino-2-(2',5'-difluorobenzoyl)-thieno[2,3-b]pyridine (0.25 g, 0.79 mmol) and morpholine (0.341 g, 3.93 mmol) in toluene (10 ml) is heated at reflux for 72 hours. The solution is washed with water and brine. After drying over $Na_2SO_4$ the drying agent is filtered off and the solution is evaporated under reduced pressure. Chromatography on silicagel yields the title compound showing a m.p. of 220° C.

Example 119a 5,6-Dimethyl-3-amino-2-(2',5'-difluorobenzoyl)-thieno[2,3-b]pyridine A suspension of potassium carbonate (0.399 g, 2.89 mmol), 2,5-difluorophenacyl bromide (0.408 g, 1.73 mmol) and 5,6-dimethyl-2-mercaptonicotine nitrile (0.19 g, 1.16 mmol) in dry DMF (4 ml) is stirred at room temperature for 16 h. The resulting mixture is diluted with ethyl acetate and washed with water. Drying over sodium sulfate, filtering, evaporating the solvent and purification of the residue by silicagel column chromatography yields the title compound with a m.p. of 188° C.

Example 120

5-Cyano-3-amino-2-(2'-ethoxy-5'-fluorobenzoyl)-thieno[2,3-b]pyridine

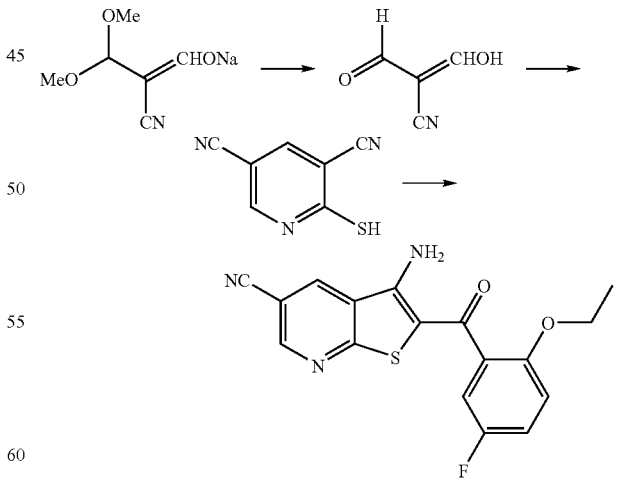

A suspension of potassium carbonate (1.18 g, 8.55 mmol), 2-ethoxy-5-fluorophenacyl bromide (1.34 g, 5.12 mmol) and 3,5-dicyano-2-mercaptopyridine (0.55 g, 3.42 mmol) in dry DMF (8 ml) is stirred at room temperature for 16 h. The resulting mixture is diluted with ethyl acetate and washed with water. Drying over sodium sulfate, filtering, evaporating the solvent and purification of the residue by silicagel column chromatography yields the title compound, having a m.p. of 196° C.

Example 120a

3,5-Dicyano-2-mercaptopyridine

A suspension of the sodium salt of 2-dimethoxymethyl-3-hydroxy-acrylonitrile (3.94 g, 23.86 mmol) in hydrochloric acid (20 ml, 0.5 M) is heated at 50° C. for 30 minutes. Excess hydrochloric acid is neturalized using triethylamine, before adding cyanoacetothioamide (2.39 g, 23.9 mmol) and a catalytic amound of benzyltrimethylammonium hydroxide. The mixture is stirred at room temperature for two hours, heated at 60° C. for 2 hours and then refluxed for 4 hours. Evaporation of the solvents leaves a solid that is purified on silicagel to yield 3,5-dicyano-2-marcaptopyridine.

$^1$H-NMR (400 MHz, DMSO-$d_6$): 14.03 (s, 3H); 8.42 (s, 1H); 8.33 (s, 1H).

TABLE 8

| Example | $R^0$ | $R^7$ | $R^{10}$ | $R^{11}$ | m.p. |
|---|---|---|---|---|---|
| 121 | piperidine | H | H | H | 160-162° C. |
| 122 | morpholine | H | H | H | 66-68° C. |
| 123 | tetrahydropyridine | H | H | H | 70-73° C. |
| 124 | piperidine | F | H | H | >200° C. |
| 125 | morpholine | F | H | H | 180-185° C. |

TABLE 8-continued

| Example | $R^0$ | $R^7$ | $R^{10}$ | $R^{11}$ | m.p. |
|---|---|---|---|---|---|
| 126 | tetrahydropyridine | F | H | H | 73-76° C. |
| 127 | O—nPr | F | $NO_2$ | H | >250° C. |
| 128 | O—nPr | F | $NH_2$ | H | 72-76° C. |
| 129 | morpholine | F | $NO_2$ | H | 225° C. |
| 130 | morpholine | F | $NH_2$ | H | 80° C. |
| 131 | morpholine | H | $NO_2$ | H | >250° C. |
| 132 | morpholine | H | $NH_2$ | H | 75-78° C. |
| 133 | O—n-Pr | H | Me | Me | 155° C. |
| 134 | morpholine | H | Me | Me | 242° C. |
| 135 | tetrahydropyridine | H | Me | Me | 175° C. |
| 136 | morpholine | F | CN | H | >250° C. |

TABLE 8-continued

[Structure: thieno[2,3-b]pyridine with NH2, R10, R11, and carbonyl to phenyl bearing R0 and R7]

| Example | R⁰ | R⁷ | R¹⁰ | R¹¹ | m.p. |
|---------|-----|-----|------|------|------|
| 137 | OEt | F | Cl | H | |
| 138 | OEt | F | Me | H | |
| 139 | OEt | F | OMe | H | |
| 140 | OEt | F | OH | H | |
| 141 | OEt | F | OAc | H | |
| 142 | OEt | F | OEt | H | |

Example 143

ω-(4-Chloro-2-cyanophenoxy)-2-ethoxy-5-fluoroacetophenone

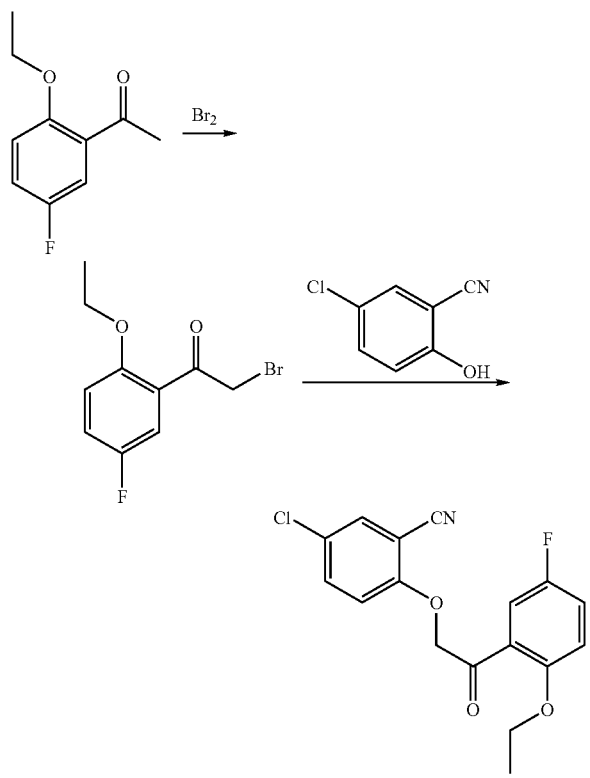

A suspension of potassium carbonate (0.66 g, 4.8 mmol), ω-bromo-2-ethoxy-5-fluoroacetophenone (0.85 g, 3.2 mmol) and 4-chloro-2-cyanophenol in dry DMF (10 ml) is stirred at room temperature for 5 h. The solid is filtered, the filtrate diluted with ethyl acetate and washed with brine. The resulting solution is dried, evaporated under reduced pressure and the residue is purified using chromatography. ¹H-NMR (CDCl₃, 400 MHz): 7.62-7.54 (m, 2H); 7.39 (d, 1H); 7.26-7.24 (m, 1H); 6.98-6.94 (m, 1H); 6.65 (d, 1H); 5.39 (s, 2H); 4.19 (q, 2H); 1.53 (t, 3H); m.p. 117-119° C.

Example 143a

ω-Bromo-2-ethoxy-5-fluoroacetophenone

Bromine (0.6 g, 3.8 mmol) is added dropwise to a stirred solution of 2-ethoxy-5-fluoroacetophenone (0.7 g, 3.8 mmol) in dry diethyl ether, the temperature being kept below 28° C. After one hour the mixture is diluted with ether and washed with water. The solution is dried and concentrated under reduced pressure to give the pure title compound. ¹H-NMR (CDCl₃, 400 MHz): 7.53 (d, 1H); 7.16-7.14 (m, 1H); 6.90 (d, 1H); 4.59 (s, 2H); 4.14 (q, 2H); 1.52 (t, 3H).

Using the procedure of Example 143, the compound Example 144 and the reference compounds (R²=H) Examples D and E are prepared:

TABLE 9

[Structure with R¹⁰, CN, R⁷, O-CH₂-R² groups]

| Example | R² | R⁷ | R¹⁰ | m.p. |
|---------|-----|-----|------|------|
| 144 | CH₃ | CH₃ | Cl | 144-146° C. |
| Ref D | H | OCH₃ | Cl | 128-130° C. |

TABLE 10

[Pyridine structure with H₃C, CN, R⁷, O-CH₂-R² groups]

| Example | R² | R⁷ | m.p. |
|---------|-----|-----|------|
| 145 | CH₃ | H | 156-158° C. |
| 146 | CH₃ | Cl | 138-140° C. |

Example 147

Cell Cultures and Cell Lines

Cell lines are cultured in RPMI-1640 tissue culture medium containing either 5% or 10% fetal calf serum, 0.05 mM 2-mercaptoethanol, 2 mM glutamine and penicillin/streptomycin 50 µg/ml (complete medium) (Sigma, Buchs, Switzerland). General growth conditions are 37° C. and 7.5% CO₂.

The following mouse cell lines (either EGFP transfected or not) are being used: A20.2J (ATCC: TIB-208), MC57G (ATCC: CRL-2295).

The following human cell lines (either EGFP transfected or not) are being used: HeLa (ATCC: CCL-2), KB (ATCC: CCL-17), MCF7 (ATCC: HTB-22), SK-BR-3 (ATCC: HTB-30), SK-Mel 1 (ATCC: HTB-67), SK-Mel 28 (ATCC: HTB-72), PC-3 (ATCC: CRL-1435), SW 480 (ATCC: CCL-228), NCI-H460 (ATCC: HTB-177), NCI-H1792 (ATCC: CRL-5895), HT1080 (ATCC: CCL-21), Jurkat (ATCC: TIB-152), Ramos (ATCC: CRL-1596), Raji (ATCC: CCL-86), Hg (ATCC: HTB-176), Hut78 (ATCC: TIB-161), Ks62 (ATCC: CCL 243), HL-60 (ATCC: CCL 240), U-87MG (ATCC: HTB-14), HepG2 (ATCC: HB-8065), U-2 OS (ATCC: HTB-96), Saos-2 (ATCC: HTB-85), U937 (ATCC: CRL 1593), Hs 578T (ATCC: HTB 126), HBL-100 (ATCC: HTB 124), Molt-4 (ATCC: CRL 1582).

As control cells primary human fibroblasts, primary human keratinocytes or freshly prepared human peripheral blood leucocytes (PBL) are being used.

Example 148

Primary Screening Setup

All the manipulations are performed under sterile conditions. The assays are being performed in commercially available 96 or 384 well flat bottom clear microtiter plates (Greiner, Germany) respectively, which are suitable for tissue culture techniques. A defined number of EGFP transfected adherent test cells (96 well plates: $10^4$-$10^5$, 384 well plates: 1500-2*$10^4$) are plated out 24 h before treatment either in 75 µl (96 well plates) or 60 µl (384 well plates) complete medium per well in order to ensure appropriate cell spreading. For this purpose a peristaltic pump (e.g. Multidrop by Thermo-Labsystems, Finland) or another suitable device is used. Cells in suspension are plated out according to the same procedure but 1 h prior to treatment. Between seeding out and treatment or addition of compounds the cells are incubated at 37° C. under 7.5% $CO_2$. Subsequently, the compounds under investigation are added at defined concentrations (40-80 µM in either 25 µl (96 well plates) or 20 µl (384 well plates) complete medium containing max 4% DMSO) with an appropriate device (e.g. liquid handling system, multi channel pipette etc.) resulting in a final concentration in the test well of 10-20 µM compound in max 1% DMSO.

Immediately after the addition of the compounds to the cells the zero fluorescence value (t=0 h) is determined by using a fluorescence microplate reader in order to be able to normalize the fluorescence activities. Afterwards, the test plates are further incubated for a total of 48 h at 37° C. under 7.5% $CO_2$ and are shortly removed only for the purpose of measurement at 8 h, 24 h and 48 h, respectively.

Example 149

Measurement and Quantification of the Primary Screening

Relative fluorescence activities of EGFP in compound treated test cells in relation to control cells and cells treated with standard drugs are measured by using a BMG Fluostar microplate fluorescence reader equipped with a filter pair for excitation/emission at 485 nm/520 nm. The optimum signal to noise ratio is detected by using the time-resolved mode of measurement with a delay of 20 µs and an integration time over 1 ms. The gain is adjusted in such a way that the control cells produce a fluorescence activity of 90% of the maximum. Kinetics is performed by measuring the relative fluorescence activities at t=0 h, 8 h, 24 h and 48 h. Crude fluorescence activities are individually normalized for different cell numbers and various optical activities of the test compounds/plate-wells by dividing each value from t=8 h, 24 h and 48 h by the value of t=0 h resulting in E(8), E(24) and E(48) values. Subsequently, the E(x) values are further processed by forming the inverse (Q-value) of the products E(8)*E(24)*E(48) which result in numbers>1 for apoptotic/necrotic activities of the compounds and numbers<1 for proliferative activities of the compounds. Controls (untreated) show values similar to 1. Compounds producing Q values>2 are being considered relevant in terms of apoptotic/necrotic activity and are subsequently tested in the secondary screening setup.

Example 150

Secondary Screening Setup

All the manipulations are performed under sterile conditions. The assays are being performed in case of adherent cells in commercially available 24 well flat bottom tissue culture plates (Greiner, Germany) and in case of suspension cells in polypropylene tubes (P-tubes) 1.4 ml (Matrix, UK), respectively.

Adherent test cells: 2*$10^4$-4*$10^4$ of EGFP transfected cells in 0.5 ml complete medium are plated out 24 h before treatment. At t=0 the medium is removed and 450 µl new complete medium is added. Subsequently, 50 µl complete medium containing the test compound in max. 5% DMSO is added resulting in final concentrations of 20 µM, 10 µM, 3 µM, 1 µM and 0.3 µM of the test compounds, respectively. After 48 h incubation the cells are harvested and analyzed with fluorescence activated cell scanning device (FACSCalibur™, BD Biosciences) according to standard procedures.

Suspension cells: $10^5$ test cells in 450 µl complete medium are pipetted into P-tubes. 50 µl complete medium containing the compounds (see adherent cells) is added immediately. After 48 h of incubation the test cells are analyzed directly on a FACSCalibur™.

Example 151

Quantification of the Secondary Screening

By monitoring the EGFP fluorescence activity in FL1 on a FACSCalibur™, it is possible to distinguish between proliferating cells, apoptotic cells and necrotic cells within the same cell population. The proliferating cells show a high GFP fluorescence activity, the apoptotic population shows an intermediate fluorescence activity whereas the necrotic cells demonstrate a residual fluorescence activity comparable to mock-transfected cells. Within the CellQuest Software (BD Biosciences) three regions are defined in the histogram: M1 comprising the proliferating cells, M2 comprising the apoptotic cell population and M3 comprising the necrotic cell population. As readout the relative abundance of the cells belonging either to M1, M2 or M3 are expressed. Compounds inducing M2 values>50% and M3 values<30% are being considered relevant and are further tested and characterized in the tertiary/advanced screening setup.

Example 152

Tertiary Screening Setup

A) Hoechst 33342 Nuclear Staining

This assay is performed in 96 well tissue culture plates. Appropriate number of cells (adherent cells: 3-5*10³, suspension cells: 8-10*10³) are being seeded out in 80 µl complete medium. Adherent cells are incubated for 24 h for proper spreading out before addition of test compounds while suspension cells are immediately treated with test compounds after seeding out. The test compounds are added in 20 µl complete medium containing max 5% DMSO. The final compound concentrations in the assays are in the range of 0.001 µM-10 µM. After 24 h or 48 h incubation at culture conditions, 10 µl medium containing Hoechst 33342 dye (Sigma B-2261) at 2-5 µg/ml are added to each well. The assay plates are then further incubated for 30 minutes and subsequently analyzed with a standard inverted fluorescence microscope.

The readout allows the determination of the fraction of apoptotic nuclei as well as other morphological criteria specific for apoptosis as a function of the treatment. Results are indicated in Table ii. The scores A, B, C and D are explained at the end of the Table.

TABLE 11

Hoechst 33342 nuclear staining (48 h read-out)

| Ex | Jurkat | Jily | PBL | HeLa | MRC5 |
|---|---|---|---|---|---|
| 1 | D | D | D | D | D |
| 2 | A | B | D | B | B |
| 3 | A | A | D | A | A |
| 4 | B | B | D | B | B |
| 5 | C | D | D | D | D |
| 6 | C | C | D | C | D |
| 7 | C | C | D | C | D |
| 8 | B | C | D | C | D |
| 9 | B | C | n.d. | C | C |
| 10 | D | D | D | D | D |
| 11 | D | D | D | D | D |
| 12 | A | A | n.d. | A | C |
| 13 | C | C | n.d. | C | C |
| 14 | B | B | n.d. | B | B |
| 15 | B | B | n.d. | C | C |
| 16 | B | B | D | B | B |
| 17 | B | B | D | B | B |
| 18 | A | A | D | A | A |
| 19 | C | C | D | C | C |
| 20 | B | B | D | C | D |
| 21 | D | D | D | D | D |
| 22 | C | C | D | C | C |
| 23 | C | C | D | D | D |
| 24 | D | D | D | D | D |
| 25 | C | C | D | D | D |
| 26 | n.d. | n.d. | n.d. | n.d. | n.d. |
| 27 | A | B | D | B | D |
| 28 | B | B | D | C | D |
| 29 | B | B | D | B | C |
| 30 | C | C | D | C | D |
| 31 | B | B | D | B | C |
| 32 | D | D | D | D | D |
| 33 | D | D | D | D | D |
| 34 | D | D | D | D | D |
| 35 | D | D | D | D | D |
| 36 | D | D | D | D | D |
| 37 | B | B | D | B | D |
| 38 | A | A | D | B | B |
| 39 | B | B | D | B | B |
| 40 | C | D | D | D | D |
| 41 | C | C | D | D | D |
| 42 | B | B | D | C | C |
| 43 | D | D | D | D | D |
| 44 | D | D | D | D | D |
| 45 | D | D | D | D | D |
| 46 | D | D | D | D | D |
| 47 | A | A | D | B | B |
| 48 | A | A | D | A | A |
| 49 | B | B | D | C | D |
| 50 | C | C | D | D | D |
| 51 | D | D | D | D | D |
| 52 | C | C | D | D | D |
| 53 | A | B | D | B | C |
| 54 | B | B | D | C | D |
| 55 | C | C | D | D | D |
| 56 | B | B | D | C | D |
| 57 | B | B | D | B | C |
| 58 | B | B | D | C | D |
| 59 | B | C | D | C | D |
| 60 | B | B | D | C | D |
| 61 | A | B | D | C | D |
| 62 | A | A | D | B | D |
| 63 | D | D | D | D | D |
| 64 | A | B | D | B | C |
| 65 | A | B | D | B | C |
| 66 | B | A | D | B | C |
| 67 | B | B | D | C | D |
| 68 | C | C | D | C | C |
| 69 | C | C | D | C | D |
| 70 | C | C | D | C | C |
| 71 | D | D | D | D | D |
| 72 | C | C | D | D | D |
| 73 | C | C | D | C | C |
| 74 | D | D | D | D | D |
| 75 | A | A | D | A | A |
| 76 | D | D | D | D | D |
| 77 | C | C | D | D | D |
| 78 | A | B | D | B | D |
| 79 | C | D | D | D | D |
| 80 | C | C | D | C | D |
| 81 | C | C | D | C | D |
| 82 | A | B | D | B | B |
| 83 | B | C | D | C | C |
| 84 | D | D | D | D | D |
| 85 | C | C | D | D | D |
| 86 | D | D | D | D | D |
| 87 | C | C | D | C | C |
| 88 | C | C | D | C | C |
| 89 | C | C | D | C | C |
| 90 | D | D | D | D | D |
| 91 | C | C | D | C | C |
| 92 | D | D | D | D | D |
| 93 | B | B | D | B | B |
| 94 | C | D | D | D | D |
| 95 | C | C | D | C | C |
| 96 | C | C | D | C | C |
| 97 | D | D | D | D | D |
| 98 | A | B | D | B | B |
| 99 | C | C | D | C | D |
| 100 | B | C | D | C | C |
| 101 | B | C | D | C | C |
| 102 | D | D | D | D | D |
| 103 | B | B | D | B | B |
| 104 | C | C | D | C | C |
| 105 | D | D | D | D | D |
| 106 | D | D | D | D | D |
| 107 | C | C | D | C | C |
| 108 | B | B | D | B | B |
| 109 | D | D | D | D | D |
| 110 | D | D | D | D | D |
| 111 | A | A | D | B | B |
| 112 | B | B | D | B | B |
| 113 | C | C | D | C | D |
| 114 | D | D | D | D | D |
| 115 | D | D | D | D | D |
| 116 | B | B | D | B | B |
| 117 | D | D | D | D | D |
| 118 | B | n.d. | n.d. | B | B |
| 119 | B | n.d. | n.d. | C | B |
| 120 | C | n.d. | n.d. | D | C |
| 121 | D | n.d. | n.d. | D | D |

TABLE 11-continued

Hoechst 33342 nuclear staining (48 h read-out)

| Ex | Jurkat | Jily | PBL | HeLa | MRC5 |
|---|---|---|---|---|---|
| 122 | D | n.d. | n.d. | D | D |
| 123 | D | n.d. | n.d. | D | D |
| 124 | D | n.d. | n.d. | D | D |
| 125 | D | n.d. | n.d. | D | D |
| 126 | D | n.d. | n.d. | D | D |
| 127 | D | n.d. | n.d. | D | D |
| 128 | C | n.d. | D | C | C |
| 129 | D | n.d. | n.d. | D | D |
| 130 | C | n.d. | n.d. | C | C |
| 131 | D | n.d. | n.d. | D | D |
| 132 | C | n.d. | n.d. | D | D |
| 133 | B | n.d. | n.d. | B | B |
| 134 | B | n.d. | n.d. | C | C |
| 135 | B | n.d. | n.d. | C | C |
| 136 | C | n.d. | n.d. | D | D |
| 137 | n.d. | n.d. | n.d. | n.d. | n.d. |
| 138 | n.d. | n.d. | n.d. | n.d. | n.d. |
| 139 | n.d. | n.d. | n.d. | n.d. | n.d. |
| 140 | n.d. | n.d. | n.d. | n.d. | n.d. |
| 141 | n.d. | n.d. | n.d. | n.d. | n.d. |
| 142 | n.d. | n.d. | n.d. | n.d. | n.d. |
| 143 | A | A | D | B | A |
| 144 | B | B | D | C | C |
| 145 | C | C | D | D | D |
| 146 | B | C | D | C | C |
| Ref A | D | D | D | D | D |
| Ref B | C | C | D | D | D |
| Ref C | D | D | D | D | D |
| Ref D | C | C | D | D | D |

A: $EC_{50} < 0.01$ μM;
B: $0.01$ μM $< EC_{50} < 0.1$ μM;
C: $0.1$ μM $< EC_{50} < 1$ μM;
D: $EC_{50} > 1$ μM
n.d.: not determined B) MTS Proliferation Assay The assay is performed in 96 well tissue culture plates. The cells (range: $1.5*10^3$-$10^4$) are seeded out in 80 μl complete medium 24 h prior to compound treatment. The test compounds are added in 20 μl complete medium containing max 5% DMSO. The final compound concentrations in the assays are in the range of 0.001 μM-10 μM. The assay plates are incubated for 72 h at culture conditions. The MTS reagent is prepared according to the manufacturer's protocol (Promega G1111). 20 μl MTS reagent are added to each well; the assay plates are quickly spun and incubated for another 3 h at culture conditions. Subsequently, the plates are shortly shaked and absorption measured with a microplate-reader at 492 nm. $IC_{50}$ values are determined by graphical analysis and are indicated in the Table 12. The scores A, B, C and D are explained at the end of the Table.

TABLE 12

MTS proliferation assay (72 h read-out)

| Ex | Jurkat | Jily | HeLa | MRC5 | HT1080 |
|---|---|---|---|---|---|
| 1 | n.d. | C | D | D | D |
| 2 | A | B | B | B | B |
| 3 | A | A | A | A | A |
| 5 | C | C | D | D | D |
| 6 | C | C | C | D | D |
| 7 | n.d. | C | C | D | C |
| 8 | B | B | C | C | C |
| 9 | B | B | C | C | B |
| 10 | D | D | D | D | D |
| 11 | D | D | D | D | D |
| 12 | A | A | B | A | A |
| 13 | B | B | C | C | C |
| 14 | A | A | B | B | B |
| 15 | B | B | C | B | B |
| 16 | A | A | B | B | B |
| 17 | A | A | B | A | A |
| 18 | A | A | A | A | A |
| 19 | n.d. | C | C | C | C |
| 20 | B | B | C | n.d. | B |
| 21 | D | D | D | D | D |
| 22 | C | C | C | C | C |
| 23 | C | C | D | D | D |
| 24 | D | D | D | D | D |
| 25 | C | C | D | D | D |
| 26 | n.d. | n.d. | n.d. | n.d. | n.d. |
| 27 | B | B | B | B | B |
| 28 | B | B | C | C | C |
| 29 | A | A | B | B | A |
| 30 | C | C | C | D | C |
| 31 | B | B | B | B | B |
| 32 | D | D | D | D | D |
| 33 | D | D | D | D | D |
| 34 | D | D | D | D | D |
| 35 | D | D | D | D | D |
| 36 | D | D | D | D | D |
| 37 | A | B | B | B | B |
| 38 | B | B | B | B | B |
| 39 | B | B | B | B | B |
| 41 | C | C | D | D | D |
| 42 | C | B | C | n.d. | B |
| 43 | D | D | D | D | D |
| 44 | D | D | D | D | D |
| 45 | D | D | D | D | D |
| 46 | D | D | D | D | D |
| 47 | A | A | B | B | A |
| 48 | A | A | A | A | A |
| 49 | B | B | C | B | B |
| 50 | C | C | D | D | D |
| 51 | n.d. | D | D | D | D |
| 52 | n.d. | C | D | D | D |
| 53 | n.d. | A | A | A | A |
| 54 | n.d. | B | B | B | B |
| 55 | B | B | C | C | C |
| 56 | A | A | B | B | B |
| 57 | A | A | B | B | B |
| 58 | A | B | B | B | B |
| 59 | B | B | C | C | B |
| 60 | B | B | C | C | B |
| 61 | A | A | B | B | B |
| 62 | A | A | B | A | A |
| 63 | D | D | D | D | D |
| 64 | A | A | B | B | B |
| 65 | A | A | B | A | A |
| 66 | n.d. | A | A | A | A |
| 67 | n.d. | A | B | B | C |
| 68 | n.d. | B | B | B | B |
| 69 | n.d. | C | C | C | C |
| 70 | n.d. | C | C | C | C |
| 71 | n.d. | D | D | D | D |
| 72 | n.d. | C | C | C | C |
| 73 | n.d. | C | C | C | C |
| 74 | n.d. | D | D | D | D |
| 75 | A | A | B | A | A |
| 76 | n.d. | D | D | D | D |
| 77 | n.d. | C | D | D | D |
| 78 | A | A | B | A | A |
| 79 | C | C | C | D | C |
| 80 | B | B | C | C | C |
| 81 | B | C | C | C | B |
| 82 | A | A | A | A | A |
| 83 | B | B | C | B | B |
| 84 | D | D | D | D | D |
| 85 | C | C | D | D | D |
| 86 | C | C | D | D | D |
| 87 | A | B | B | B | B |
| 88 | A | A | B | A | A |
| 89 | B | B | C | C | C |
| 90 | D | D | D | D | D |

TABLE 12-continued

MTS proliferation assay (72 h read-out)

| Ex | Jurkat | Jily | HeLa | MRC5 | HT1080 |
|---|---|---|---|---|---|
| 91 | A | A | B | A | A |
| 92 | D | D | D | D | D |
| 93 | C | B | B | B | B |
| 94 | C | C | C | C | C |
| 95 | B | B | B | B | B |
| 96 | B | B | B | B | B |
| 97 | C | C | D | C | C |
| 98 | A | B | B | A | B |
| 99 | B | B | C | B | C |
| 100 | B | B | C | B | B |
| 101 | B | C | C | C | B |
| 102 | C | D | D | D | D |
| 103 | B | B | B | B | B |
| 104 | C | C | C | C | C |
| 105 | D | D | D | D | D |
| 106 | D | D | D | D | D |
| 107 | B | B | B | B | B |
| 108 | B | B | B | B | B |
| 109 | D | D | D | D | D |
| 110 | D | D | D | D | D |
| 111 | n.d. | n.d. | n.d. | n.d. | n.d. |
| 112 | n.d. | n.d. | n.d. | n.d. | n.d. |
| 113 | C | C | C | D | D |
| 114 | D | D | D | D | D |
| 115 | D | D | D | D | D |
| 116 | B | B | C | C | C |
| 117 | D | D | D | D | D |
| 118 | B | B | B | n.d. | B |
| 119 | B | B | C | n.d. | B |
| 120 | C | C | C | n.d. | C |
| 121 | D | D | D | n.d. | D |
| 122 | D | D | D | n.d. | D |
| 123 | D | D | D | n.d. | D |
| 124 | D | D | D | n.d. | D |
| 125 | C | C | D | n.d. | D |
| 126 | C | C | D | n.d. | C |
| 127 | D | D | D | n.d. | D |
| 128 | C | C | D | n.d. | C |
| 129 | D | D | D | n.d. | D |
| 130 | B | B | C | n.d. | C |
| 131 | D | D | D | n.d. | D |
| 132 | C | C | D | n.d. | D |
| 133 | B | B | B | n.d. | B |
| 134 | B | B | C | n.d. | B |
| 135 | B | B | C | n.d. | B |
| 136 | C | C | C | n.d. | C |
| 137 | n.d. | n.d. | n.d. | n.d. | n.d. |
| 138 | n.d. | n.d. | n.d. | n.d. | n.d. |
| 139 | n.d. | n.d. | n.d. | n.d. | n.d. |
| 140 | n.d. | n.d. | n.d. | n.d. | n.d. |
| 141 | n.d. | n.d. | n.d. | n.d. | n.d. |
| 142 | n.d. | n.d. | n.d. | n.d. | n.d. |
| 143 | B | B | B | B | B |
| 144 | B | B | C | C | C |
| 145 | n.d. | n.d. | n.d. | n.d. | n.d. |
| 146 | n.d. | n.d. | n.d. | n.d. | n.d. |
| Ref A | D | D | D | D | D |
| Ref B | C | C | C | C | C |
| Ref C | D | D | D | D | D |
| Ref D | C | C | C | D | C |

A: $IC_{50} < 0.01\ \mu M$;
B: $0.01\ \mu M < IC_{50} < 0.1\ \mu M$;
C: $0.1\ \mu M < IC_{50} < 1\ \mu M$;
D: $IC_{50} > 1\ \mu M$
n.d.: not determined C) PI Staining for Cell Cycle Distribution $1\text{-}2*10^5$ cells are seeded into 24 well tissue culture plates and incubated for 24 h prior to compound addition. Compounds are added for 24 h in a final concentration of 3 μM or 10 μM. Adherent cells are harvested by trypsinization. The cell suspensions are fixed by adding 2 parts ice cold ethanol 100% while vortexing. Then the samples are stored for >2 h at −20° C. Subsequently the cells are washed with PBS once and resuspended in 250 μl PBS containing 50 μg/ml PI (Calbiochem #537059), then the samples are incubated at 37° C. for 30 minutes and subsequently analyzed on a FACSCalibur™ monitoring linear PI fluorescence activity on FL2. The read-out allows the detection of a possible direct or indirect influence of the tested compounds on the cell cycle. All active compounds of formula (I) and formula (II) arrest cell population in G2M phase. In this assay compounds have shown activity at concentrations as low as 20 nM.

D) Mitochondrial Membrane Potential

This assay is performed in 96 well tissue culture plates. Appropriate number of cells (adherent cells: $3\text{-}5*10^3$, suspension cells: $8\text{-}10*10^3$) are being seeded out in 80 μl complete medium. Adherent cells are incubated for 24 h for proper spreading out before addition of test compounds while suspension cells are immediately treated with test compounds after seeding out. The test compounds are added in 20 μl complete medium containing max 5% DMSO. The final compound concentrations in the assays are in the range of 0.001 μM-10 μM dependent on the potency of the compounds under investigation. After 24 h or 48 h incubation at culture conditions, 10 μl medium containing JC-1 (Molecular Probes, T-3168) at 2-5 μg/ml are added to each well. The assay plates are then further incubated for 30 minutes and subsequently analyzed with a standard inverted fluorescence microscope by using the FITC and TRITC filters. Cells with an intact mitochondrial membrane potential (mmp) show an orange staining (visualized with the TRITC filter) while cells with a perturbed or missing mmp demonstrate a green staining (visualized with the FITC filter).

The readout allows the determination of the fraction of cells which show a dissipation of the mitochondrial membrane potential strongly indicating an apoptotic cell death as a function of the treatment. Results are indicated in Table 13. The scores A, B, C and D are explained at the end of the Table.

TABLE 13

Mitochondrial membrane potential (read-out 48 h)

| Ex | Jurkat | Jily | PBL | HeLa | MCF7 |
|---|---|---|---|---|---|
| 1 | C | D | D | D | D |
| 2 | A | B | D | B | C |
| 3 | A | A | D | A | B |
| 4 | B | B | D | B | B |
| 5 | C | D | D | D | D |
| 6 | C | C | D | C | C |
| 7 | C | C | D | C | D |
| 8 | C | C | D | C | C |
| 9 | B | C | D | C | C |
| 10 | D | D | D | D | D |
| 11 | D | D | D | D | D |
| 12 | A | A | D | B | B |
| 13 | C | C | D | C | C |
| 14 | B | B | D | B | B |
| 15 | B | C | D | C | C |
| 16 | B | B | D | B | B |
| 17 | B | B | D | B | B |
| 18 | A | A | D | A | A |
| 19 | C | C | D | C | C |
| 20 | B | B | D | C | C |
| 21 | D | D | D | D | D |
| 22 | C | C | D | C | D |
| 23 | C | D | D | D | D |
| 24 | D | D | D | D | D |
| 25 | C | C | D | D | D |
| 26 | n.d. | n.d. | n.d. | n.d. | n.d. |
| 27 | B | B | D | B | C |
| 28 | B | C | D | C | D |
| 29 | B | B | D | B | B |
| 30 | C | C | D | C | D |
| 31 | B | B | D | C | D |

TABLE 13-continued

Mitochondrial membrane potential (read-out 48 h)

| Ex | Jurkat | Jily | PBL | HeLa | MCF7 |
|---|---|---|---|---|---|
| 32 | D | D | D | D | D |
| 33 | D | D | D | D | D |
| 34 | D | D | D | D | D |
| 35 | D | D | D | D | D |
| 36 | D | D | D | D | D |
| 37 | B | B | D | C | D |
| 38 | B | B | D | B | B |
| 39 | B | B | D | B | C |
| 40 | C | D | D | D | D |
| 41 | C | D | D | D | D |
| 42 | B | B | D | C | C |
| 43 | D | D | D | D | D |
| 44 | D | D | D | D | D |
| 45 | D | D | D | D | D |
| 46 | D | D | D | D | D |
| 47 | B | B | D | B | D |
| 48 | A | A | C | B | B |
| 49 | B | B | D | C | D |
| 50 | C | D | D | D | D |
| 51 | D | D | D | D | D |
| 52 | C | C | D | D | D |
| 53 | B | B | D | B | B |
| 54 | B | C | D | C | B |
| 55 | C | B | D | D | C |
| 56 | B | C | D | C | C |
| 57 | B | B | D | C | C |
| 58 | B | B | D | C | C |
| 59 | B | C | D | D | D |
| 60 | B | B | D | C | D |
| 61 | B | B | D | C | D |
| 62 | A | A | D | B | D |
| 63 | D | D | D | D | D |
| 64 | A | B | D | B | D |
| 65 | A | B | D | B | D |
| 66 | B | B | D | C | C |
| 67 | B | B | D | C | D |
| 68 | C | C | D | D | D |
| 69 | C | C | D | D | D |
| 70 | C | C | D | D | D |
| 71 | D | D | D | D | D |
| 72 | C | C | D | D | D |
| 73 | C | C | D | C | D |
| 74 | D | D | D | D | D |
| 75 | A | A | D | A | B |
| 76 | D | D | D | D | D |
| 77 | C | C | D | D | D |
| 78 | A | B | D | B | C |
| 79 | C | C | D | D | D |
| 80 | B | C | D | C | D |
| 81 | B | C | D | D | D |
| 82 | A | A | D | B | B |
| 83 | B | C | D | C | C |
| 84 | D | D | D | D | D |
| 85 | C | C | D | D | D |
| 86 | D | D | D | D | D |
| 87 | C | C | D | C | C |
| 88 | B | B | D | B | B |
| 89 | C | C | D | C | C |
| 90 | D | D | D | D | D |
| 91 | B | B | D | B | B |
| 92 | B | B | D | B | B |
| 93 | B | C | D | B | C |
| 94 | C | C | D | D | D |
| 95 | B | B | D | B | B |
| 96 | B | B | D | B | B |
| 97 | D | D | D | D | D |
| 98 | A | A | D | A | A |
| 99 | C | C | D | C | C |
| 100 | B | B | D | C | C |
| 101 | B | B | D | C | C |
| 102 | D | D | D | D | D |
| 103 | B | B | D | B | B |
| 104 | C | C | D | C | C |
| 105 | D | D | D | D | D |
| 106 | D | D | D | D | D |
| 107 | B | B | D | C | C |
| 108 | B | B | D | C | C |
| 109 | D | D | D | D | D |
| 110 | D | D | D | D | D |
| 111 | A | A | D | B | B |
| 112 | B | B | D | B | B |
| 113 | C | C | D | D | D |
| 114 | D | D | D | D | D |
| 115 | D | D | D | D | D |
| 116 | B | B | D | C | D |
| 117 | D | D | D | D | D |
| 118 | B | B | n.d. | C | D |
| 119 | C | C | n.d. | D | D |
| 120 | C | C | n.d. | D | D |
| 121 | D | D | n.d. | D | D |
| 122 | D | D | n.d. | D | D |
| 123 | D | D | n.d. | D | D |
| 124 | D | D | n.d. | D | D |
| 125 | C | C | n.d. | D | D |
| 126 | C | C | n.d. | D | D |
| 127 | D | D | n.d. | D | D |
| 128 | C | D | n.d. | D | D |
| 129 | D | D | n.d. | D | D |
| 130 | C | C | n.d. | C | D |
| 131 | D | D | n.d. | D | D |
| 132 | D | D | n.d. | D | D |
| 133 | B | B | n.d. | B | D |
| 134 | B | B | n.d. | B | D |
| 135 | B | B | n.d. | D | D |
| 136 | C | C | n.d. | D | D |
| 137 | n.d. | n.d. | n.d. | n.d. | n.d. |
| 138 | n.d. | n.d. | n.d. | n.d. | n.d. |
| 139 | n.d. | n.d. | n.d. | n.d. | n.d. |
| 140 | n.d. | n.d. | n.d. | n.d. | n.d. |
| 141 | n.d. | n.d. | n.d. | n.d. | n.d. |
| 142 | n.d. | n.d. | n.d. | n.d. | n.d. |
| 143 | A | n.d. | D | B | B |
| 144 | B | n.d. | D | C | C |
| 145 | C | n.d. | D | D | C |
| 146 | B | n.d. | D | C | C |
| Ref A | D | D | D | D | D |
| Ref B | C | C | C | D | D |
| Ref C | D | D | D | D | D |
| Ref D | C | n.d. | D | D | D |

A: $EC_{50} < 0.01\ \mu M$;
B: $0.01\ \mu M < EC_{50} < 0.1\ \mu M$;
C: $0.1\ \mu M < EC_{50} < 1\ \mu M$
D: $EC_{50} > 1\ \mu M$
n.d.: not determined E) Colony Forming Units Appropriate numbers of cells (100-150 cells, dependent on the cell type) are being seeded out in 1 ml complete medium into 6-well plates and allowed to attach for 48 h. The compounds are added after 48 h in 500 µl solution. The concentrations are in the range of 0.001 µM-3 µM. Control plates receive the same volume of medium containing the appropriate amount of DMSO. The plates are incubated for 5-7 days at cell culture conditions and subsequently scored for growth of colonies (containing more than 30 cells) by using a microscope. Scores based on IC50 values are indicated in Table 14.

TABLE 14

Colony Forming Units (read-out 6 days)

| Example | HeLa | H460 |
|---|---|---|
| 2 | B | B |
| 3 | A | A |
| 4 | B | B |
| 6 | C | C |
| 8 | C | C |

TABLE 14-continued

| Colony Forming Units (read-out 6 days) | | |
|---|---|---|
| Example | HeLa | H460 |
| 9 | B | B |
| 12 | B | A |
| 13 | C | C |
| 14 | B | B |
| 15 | B | B |
| 18 | A | A |
| 29 | B | B |
| 37 | B | B |
| 38 | A | A |
| 48 | B | A |
| 53 | B | B |
| 58 | B | B |
| 61 | B | B |
| 64 | B | B |
| 66 | A | A |
| 75 | B | B |
| 78 | B | B |
| 80 | C | C |
| 82 | B | B |
| 96 | B | B |
| 98 | B | B |

A: IC50 < 0.01 μM;
B: 0.01 μM < IC50 < 0.1 μM;
C: 0.1 μM < IC50 < 1 μM
D: IC50 > 1 μM
n.d.: not determined

What is claimed:

1. A compound of formula (I)

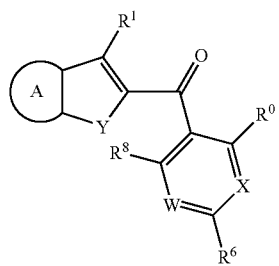

(I)

wherein ring A is selected from rings of formula ($A^1$), ($A^4$) and ($A^5$)

($A^1$)

($A^4$)

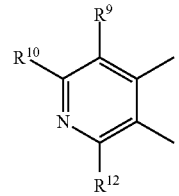

($A^5$)

W represents $CR^7$, N, or N→O;

X represents $CR^5$, N, or N→O;

Y represents O or S;

$R^0$ is $NR^{16}R^{17}$, lower alkoxymethyl, optionally substituted cyclohexyl, optionally substituted cyclohexenyl, lower alkyl or lower alkoxy substituted phenyl, optionally substituted pyridyl, optionally substituted dihydropyridyl, optionally substituted tetrahydropyridinyl, optionally substituted pyrimidinyl, optionally substituted tetrahydropyranyl, or optionally substituted dihydropyranyl, and wherein the optional substituents are lower alkyl or lower alkoxy;

$R^1$ is hydrogen or $NHR^{15}$;

$R^5$ represents hydrogen, lower alkyl, halo-lower alkyl or fluoro;

$R^6$ is hydrogen;

$R^7$ represents hydrogen, lower alkyl, hydroxy, lower alkoxy, lower alkenyloxy, lower alkinyloxy, cyano, halogen, or nitro;

$R^8$ represents hydrogen or fluoro;

$R^9$ represents hydrogen, lower alkyl or halogen;

$R^{10}$ represents hydrogen, lower alkyl, halo-lower alkyl, hydroxy-lower alkyl, lower alkoxy-lower alkyl, cycloalkyl, hydroxy, lower alkoxy, halo-lower alkoxy, lower alkoxy-lower alkoxy, cycloalkyloxy, alkenyloxy, alkinyloxy, alkylmercapto, alkylsulfinyl, halo-lower alkylsulfinyl, alkylsulfonyl; amino optionally substituted by one or two substitutents selected from lower alkyl, cycloalkyl, cycloalkyl-lower alkyl, hydroxy-lower alkyl, lower alkoxy-lower alkyl, di-lower alkylamino-lower alkyl, alkylcarbonyl, alkoxycarbonyl or aminocarbonyl, and wherein alkyl or lower alkyl in each case may be substituted by halogen, lower alkoxy, aryl, heteroaryl or optionally substituted amino, or wherein the two substituents on nitrogen form together with the nitrogen heterocyclyl; lower alkylcarbonyl, halo-lower alkylcarbonyl, optionally substituted phenylcarbonyl, carboxy, lower alkoxycarbonyl, lower alkoxy-lower alkoxycarbonyl; cyano, halogen, or nitro;

$R^{11}$ represents hydrogen, lower alkyl, lower alkoxy, lower alkylamino, or halogen;

$R^{12}$ represents hydrogen, lower alkyl, halo-lower alkyl or fluoro;

$R^{15}$ represents hydrogen, lower alkylcarbonyl or lower alkylsulfonyl wherein lower alkyl may be substituted by hydroxy, lower alkoxy or halogen; or lower alkoxycarbonyl;

$R^{16}$ and $R^{17}$, independently of each other, represent lower alkyl, lower alkenyl or halo-lower alkyl, or $R^{16}$ and $R^{17}$ together with the nitrogen atom they are bound to form heterocyclyl;

or pharmaceutically acceptable salts thereof.

2. A compound of formula (I)

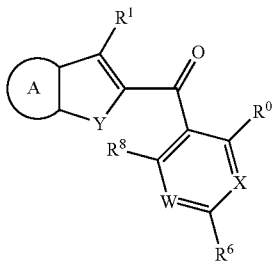

wherein ring A is

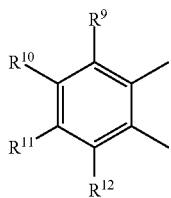

W represents $CR^7$;
X represents $CR^5$;
Y represents O;
$R^0$ is $OCR^2R^3R^4$;
$R^1$ is $NHR^{15}$;
$R^2$ is lower alkyl, vinyl or trifluoromethyl;
$R^3$ is hydrogen or methyl;
$R^4$, $R^5$ and $R^6$ represent hydrogen;
$R^7$ represents hydrogen, lower alkyl, lower alkoxy, fluoro, chloro, or nitro;
$R^8$ and $R^9$ represent hydrogen;
$R^{10}$ represents hydrogen, lower alkyl, hydroxy, lower alkoxy or halogen;
$R^{11}$ and $R^{12}$ represents hydrogen; and
$R^{15}$ represents hydrogen, methanesulfonyl or methoxyacetyl;
or pharmacetuically acceptable salts thereof.

3. The compound of the formula

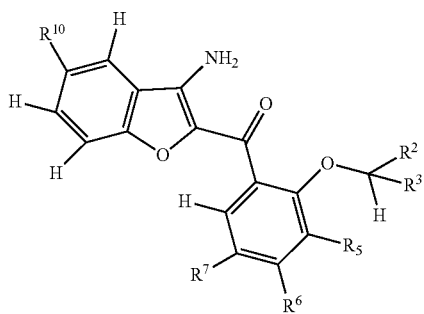

wherein
$R^2$ is lower alkyl, lower alkoxy-lower alkyl, heterocyclyl-lower alkyl, di(lower alkyl)amino-lower alkyl or lower alkinyl;
$R^3$ is hydrogen or lower alkyl;
$R^5$ and $R^6$ independently of each other, are hydrogen, lower alkyl or lower alkoxy;
$R^7$ is hydrogen, lower alkyl, lower alkoxy, pyrrol-1-yl, amino optionally substituted by alkylcarbonyl; lower alkoxycarbonyl, cyano, halogen, or nitro; and
$R^{10}$ is lower alkyl, hydrogen, hydroxy, lower alkoxy or halogen;
or pharmaceutically acceptable salts thereof.

4. The compounds of claim 3 wherein $R^{10}$ is halogen.
5. The compounds of claim 4 wherein $R^{10}$ is chloro.
6. The compounds of claim 5 wherein $R^5$ is hydrogen.
7. The compounds of claim 6 wherein $R^6$ is hydrogen.
8. The compounds of claim 7 wherein $R^3$ is hydrogen or lower alkyl and $R^2$ is methyl.
9. The compounds of claim 8 wherein $R^7$ is hydrogen, methoxy, nitro, fluoro, chloro or bromo.
10. The compound of claim 9 wherein $R^7$ is fluoro and $R^3$ is hydrogen.
11. The compound of claim 10 wherein said compound is a pharmaceutically acceptable salt.
12. The compound of claim 9 wherein $R^7$ is nitro, and $R^3$ is hydrogen.
13. The compound of claim 9 wherein $R^3$ is hydrogen.
14. The compound of claim 13 wherein $R^7$ is hydrogen.
15. The compound of claim 8 wherein $R^3$ and $R^7$ are methyl.
16. The compound of claim 13 wherein $R^7$ is chloro.
17. The compound of claim 7 wherein $R^7$ is lower alkoxy.
18. The compound of claim 17 wherein $R^7$ is methoxy and $R^3$ is hydrogen.
19. The compound of claim 3 wherein $R^{10}$ is hydroxy or lower alkoxy.
20. The compound of claim 19 wherein $R^{10}$ is methoxy, $R^2$ is methyl, $R^3$, $R^5$, $R^6$ and $R^7$ are hydrogen.
21. The compound of claim 19 wherein $R^{10}$ is methoxy, $R^2$ is methyl, $R^3$, $R^5$ and $R^6$ are hydrogen and $R^7$ is fluoro.
22. The compound of claim 19 wherein $R^{10}$ is hydroxy, $R^2$ is methyl, $R^3$, $R^5$ and $R^6$ are hydrogen and $R^7$ is fluoro.
23. The compound of claim 1 wherein ring A is ($A^1$), $R^1$ is hydrogen, W is $CR^7$, X is $CR^5$, Y is —O— and
$R^0$ is $NR^{16}R^{17}$ and $R^{16}$ and $R^{17}$ taken together with the nitrogen atom they are bound to form heterocyclyl.
24. The compound of claim 23 wherein $R^{10}$ is lower alkoxy and $R^{16}$ and $R^{17}$ taken together with their attached nitrogen atom form morpholino.
25. The compound of claim 24 wherein $R^{10}$ is methoxy, $R^5$ is hydrogen, $R^7$ is fluoro and $R^8$, $R^9$, $R^{11}$ and $R^{12}$ are hydrogen.
26. The compound of claim 18 wherein $R^2$ is methyl.
27. The compound of claim 18 wherein R2 is ethyl.

* * * * *